US007807778B2

(12) United States Patent
Backer et al.

(10) Patent No.: US 7,807,778 B2
(45) Date of Patent: *Oct. 5, 2010

(54) CYSTEINE-CONTAINING PEPTIDE TAG FOR SITE-SPECIFIC CONJUGATION OF PROTEINS

(75) Inventors: Marina V. Backer, Simsbury, CT (US); Joseph M. Backer, Simsbury, CT (US)

(73) Assignee: SibTech, Inc., Brookfield, CT (US)

( * ) Notice: Subject to any disclaimer, the term of this patent is extended or adjusted under 35 U.S.C. 154(b) by 230 days.

This patent is subject to a terminal disclaimer.

(21) Appl. No.: 12/075,811

(22) Filed: Mar. 14, 2008

(65) Prior Publication Data

US 2008/0312410 A1 Dec. 18, 2008

Related U.S. Application Data

(60) Division of application No. 11/083,508, filed on Mar. 18, 2005, now Pat. No. 7,355,019, which is a continuation-in-part of application No. 09/872,712, filed on Jun. 1, 2001, now abandoned.

(60) Provisional application No. 60/209,660, filed on Jun. 6, 2000.

(51) Int. Cl.
*A61K 38/10* (2006.01)
*A61K 38/18* (2006.01)
*C07K 7/08* (2006.01)
*C07K 14/475* (2006.01)

(52) U.S. Cl. ............ 530/300; 530/326; 530/399; 530/402

(58) Field of Classification Search ............ None
See application file for complete search history.

(56) References Cited

U.S. PATENT DOCUMENTS

| | | | |
|---|---|---|---|
| 4,885,172 A | 12/1989 | Bally et al. | 424/417 |
| 5,194,596 A | 3/1993 | Tischer | 530/399 |
| 5,492,840 A | 2/1996 | Malmqvist et al. | 436/518 |
| 5,506,121 A | 4/1996 | Skerra | 435/69.7 |
| 5,661,025 A | 8/1997 | Szoka, Jr. et al. | 435/172.3 |
| 5,712,136 A | 1/1998 | Wickham et al. | 435/172.3 |
| 5,766,899 A | 6/1998 | Kuo et al. | 435/172.3 |
| 5,792,645 A | 8/1998 | Beug et al. | 435/240.2 |
| 5,837,533 A | 11/1998 | Boutin | 435/320.1 |
| 5,853,744 A | 12/1998 | Mooradian et al. | 424/422 |
| 5,858,743 A | 1/1999 | Russell et al. | 435/172.3 |
| 5,859,228 A | 1/1999 | Janjic | |
| 5,874,297 A | 2/1999 | Wu et al. | 435/320.1 |
| 5,972,707 A | 10/1999 | Krishnendu | |
| 5,972,901 A | 10/1999 | Ferkol, Jr. et al. | 514/44 |
| 5,998,192 A | 12/1999 | Russell et al. | 435/235.1 |
| 6,015,897 A | 1/2000 | Theodore | |
| 6,033,719 A | 3/2000 | Keough | 427/2.12 |
| 6,037,329 A | 3/2000 | Baird et al. | 514/44 |
| 6,056,973 A | 5/2000 | Allen | |
| 6,057,428 A | 5/2000 | Keyt et al. | 530/399 |
| 6,075,010 A | 6/2000 | Theodore | 514/23 |
| 6,251,599 B1 | 6/2001 | Chen et al. | 435/6 |
| 6,284,742 B1 | 9/2001 | Curiel et al. | 514/44 |
| 6,342,219 B1 | 1/2002 | Thorpe et al. | 424/145.1 |
| 6,342,221 B1 | 1/2002 | Thorpe et al. | 424/178.1 |
| 6,395,707 B1 | 5/2002 | Zioncheck et al. | 514/12 |
| 6,416,758 B1 | 7/2002 | Thorpe et al. | 424/145.1 |
| 6,485,942 B1 | 11/2002 | Zioncheck et al. | 435/69.4 |
| 6,503,886 B1 | 1/2003 | Baird et al. | 514/44 |
| 6,524,583 B1 | 2/2003 | Thorpe et al. | 424/145.1 |
| 6,541,008 B1 | 4/2003 | Wise et al. | 424/198.1 |
| 6,559,126 B2 | 5/2003 | Tournaire et al. | 514/16 |
| 6,660,843 B1 | 12/2003 | Feige et al. | 530/391.7 |
| 6,676,941 B2 | 1/2004 | Thorpe et al. | 424/178.1 |
| 6,703,020 B1 | 3/2004 | Thorpe et al. | 424/178.1 |
| 6,750,044 B1 | 6/2004 | Keyt et al. | 435/69.4 |
| 2001/0038851 A1 | 11/2001 | Allen | 424/450 |

FOREIGN PATENT DOCUMENTS

| | | |
|---|---|---|
| WO | WO 95/26412 | 10/1995 |
| WO | WO 97/05266 | 2/1997 |

OTHER PUBLICATIONS

Backer, Marina V. et al.: "Assembly of targeting complexes driven by a single-chain antibody", Journal of Immunological Methods, vol. 289, No. 1-2, pp. 37-45 (Jun. 1, 2004).
Backer, Marina V. et al.: "Adapter Protein for Site-Specific Conjugation of Payloads for Targeted Drug Delivery", Bioconjugate Chemistry, vol. 15, No. 5, pp. 1021-1029, Continued: (Sep. 2004).
Backer, Marina V. et al.: "Humanized docking system for assembly of targeting drug delivery complexes", Journal of Controlled Release, vol. 89, No. 3, pp. 499-511, Continued: (May 20, 2003).

(Continued)

*Primary Examiner*—Maryam Monshipouri
*Assistant Examiner*—Marsha M Tsay
(74) *Attorney, Agent, or Firm*—Todd E. Garabedian; Wiggin and Dana LLP

(57) ABSTRACT

The present invention is directed to a biological conjugate, comprising: (a) a targeting moiety comprising a polypeptide having an amino acid sequence comprising the polypeptide sequence of SEQ ID NO:2 and the polypeptide sequence of a selected targeting protein; and (b) a binding moiety bound to the targeting moiety; the biological conjugate having a covalent bond between the thiol group of SEQ ID NO:2 and a functional group in the binding moiety. The present invention is directed to a biological conjugate, comprising: (a) a targeting moiety comprising a polypeptide having an amino acid sequence comprising the polypeptide sequence of SEQ ID NO:2 and the polypeptide sequence of a selected targeting protein; and (b) a binding moiety that comprises an adapter protein, the adapter protein having a thiol group; the biological conjugate having a disulfide bond between the thiol group of SEQ ID NO:2 and the thiol group of the adapter protein. The present invention is also directed to biological sequences employed in the above biological conjugates, as well as pharmaceutical preparations and methods using the above biological conjugates.

13 Claims, 24 Drawing Sheets

OTHER PUBLICATIONS

Futami, Junichiro, et al.: J. Biochemistry, "*Stabilization of Human RNase 1 by Introduction of a Disulfide Bond between Residues 4 and 118[1]*", vol. 128, pp. 245-250 (2000) via website: http://jb.bcasj.or.jp/128-2/2eyajltx.htm.

Raines, Ronald T: Chemical Reviews, vol. 98, No. 3, pp. 1045-1065 (1998).

Sigma Aldrich Co: Material Safety Data Sheet for Ribonuclease A (From www.easternct.edu/depts/env_saf/Ribonuclease_A.html) (2001).

Kim, Jin-Soo and Raines, Ronald T: Protein Science, 2, pp. 348-356 (1993).

Dasilva, et al.: Leukemia, vol. 8, No. 5, pp. 885-889 (1994).

Kumagai, et al.: J. Biochem, vol. 81, No. 2, pp. 381-388 (1997).

Melbye, et al.: J. Invest. Dermatol., vol. 68, No. 5, pp. 285-292 (1997).

Rushizky, et al.: Biochem, vol. 128, pp. 787-793 (1963).

Deonarain, M.P.: Exp. Opin. Ther. Patents, vol. 8, No. 1, pp. 53-69 (1998).

Tillman, B. W., et al.: 1999 The Journal of Immunology. pp. 6378-6383.

Romano, G., et al.: Stem Cells, vol. 18, pp. 19-39 (2000).

Somia, N., et al.: Nature Reviews Genetics, vol. 1, pp. 91-99 (Nov. 2000).

Crystal, R. G., et al.: Science, vol. 270, pp. 404-410 (Oct. 20, 1995).

Anderson, W. F.: Nature, vol. 392, pp. 25-30 (Apr. 1998).

Verma, I. M.: Nature, vol. 389, pp. 239-242 (Sep. 1997).

Miller, N., et al.: The FASEB Journal, vol. 9, pp. 190-199 (Feb. 1995).

BH–RNase(C88, C118) deprotection

↓ 1mM DTT, 0.5 NDSB, 16 hrs at 4°C

Subtilisin digestion of deprotected BH–RNase(C88, C118)

↓ Subtilisin to BH–RNase(C88, C118) w/w ratio 1:10
15 min at 4°C

Fractionation on cation–exchange SP column

↓ Subtulisin is separated from digested protein

Conjugation with C4–VEGF

↓ C4–VEGF to HuS(C88, C118) molar ratio 1:3
16 hrs at 4°C

Modification with Cy5.5

↓ Cy5.5–maleimide to HuS(C88, C118) molar ratio 4:1
1 hr at room temperature

Purification of Cy5.5–HuS–C4–VEGF

↓ desalting to remove unreacted Cy5.5
RP HPLC purification of Cy5.5–HuS–C4–VEGF on C4 column
Buffer exchange on cation–exchange SP column HPLC analysis of purified Cy5.5–HuS–C4–VEGF

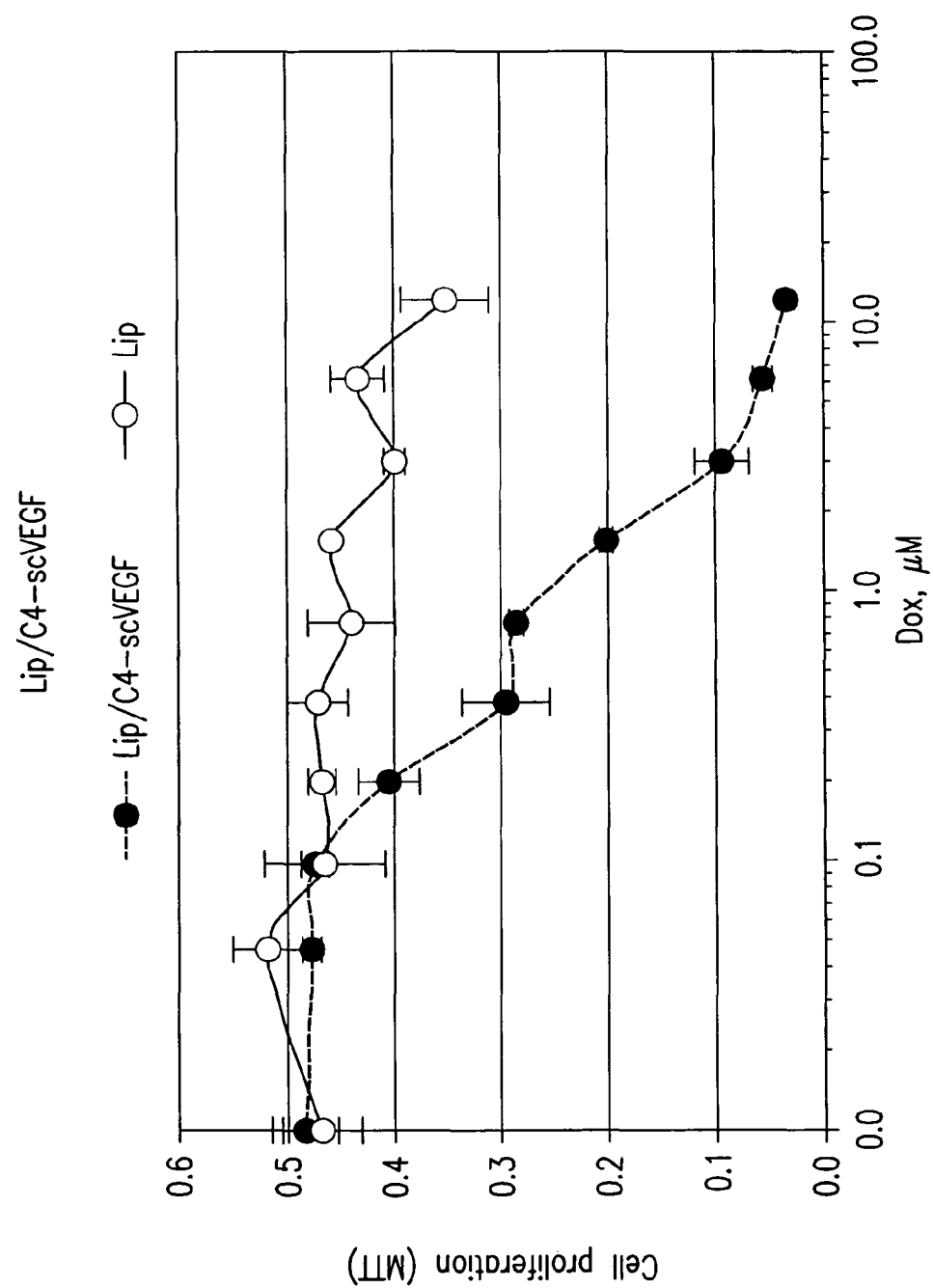

SEQUENCE LISTING

<160> NUMBER OF SEQ ID NOS: 46

<210> SEQ ID NO 1
<211> LENGTH: 45
<212> TYPE: DNA
<213> ORGANISM: Artificial Sequence
<220> FEATURE:
<223> OTHER INFORMATION: Mutant DNA fragment of human RNase I

<400> SEQUENCE: 1

```
aaagaatctt gcgctaaaaa atttcaacgt caacacatgg actct            45
```

<210> SEQ ID NO 2
<211> LENGTH: 15
<212> TYPE: PRT
<213> ORGANISM: Artificial Sequence
<220> FEATURE:
<223> OTHER INFORMATION: Mutant N-terminal 15 amino acid long fragment
      of human RNase I

<400> SEQUENCE: 2

```
Lys Glu Ser Cys Ala Lys Lys Phe Gln Arg Gln His Met Asp Ser
1               5                   10                  15
```

<210> SEQ ID NO 3
<211> LENGTH: 666
<212> TYPE: DNA
<213> ORGANISM: Artificial Sequence
<220> FEATURE:
<223> OTHER INFORMATION: Single Chain Vascular Endothelial Growth Factor
      (scVEGF) DNA
<220> FEATURE:
<221> NAME/KEY: CDS
<222> LOCATION: (1)...(666)

<400> SEQUENCE: 3

```
atg gca gaa gga gga ggg cag aat cat cac gaa gtg gtg aag ttc atg       48
Met Ala Glu Gly Gly Gly Gln Asn His His Glu Val Val Lys Phe Met
1               5                   10                  15 gat gtc tat cag cgc agc tac tgc cat cca atc gag acc ctg gtg gac       96
Asp Val Tyr Gln Arg Ser Tyr Cys His Pro Ile Glu Thr Leu Val Asp
                20                  25                  30 atc ttc cag gag tac cct gat gag atc gag tac atc ttc aag cca tcc      144
Ile Phe Gln Glu Tyr Pro Asp Glu Ile Glu Tyr Ile Phe Lys Pro Ser
            35                  40                  45 tgt gtg ccc ctg atg cga tgc ggg ggc tgc tgc aat gac gag ggc ctg      192
Cys Val Pro Leu Met Arg Cys Gly Gly Cys Cys Asn Asp Glu Gly Leu
        50                  55                  60 gag tgt gtg ccc act gag gag tcc aac atc acc atg cag att atg cgg      240
Glu Cys Val Pro Thr Glu Glu Ser Asn Ile Thr Met Gln Ile Met Arg
65                  70                  75                  80 atc aaa cct cac caa ggc cag cac ata gga gag atg agc ttc cta cag      288
Ile Lys Pro His Gln Gly Gln His Ile Gly Glu Met Ser Phe Leu Gln
                85                  90                  95 cac aac aaa tgt gaa tgc aga cca aag aaa gat aga gca aga gcc atg      336
His Asn Lys Cys Glu Cys Arg Pro Lys Lys Asp Arg Ala Arg Ala Met
                100                 105                 110 gca gaa gga gga ggg cag aat cat cac gaa gtg gtg aag ttc atg gat      384
Ala Glu Gly Gly Gly Gln Asn His His Glu Val Val Lys Phe Met Asp
            115                 120                 125 gtc tat cag cgc agc tac tgc cat cca atc gag acc ctg gtg gac atc      432
Val Tyr Gln Arg Ser Tyr Cys His Pro Ile Glu Thr Leu Val Asp Ile
        130                 135                 140
```

```
                                                               -continued ttc cag gag tac cct gat gag atc gag tac atc ttc aag cca tcc tgt       480
Phe Gln Glu Tyr Pro Asp Glu Ile Glu Tyr Ile Phe Lys Pro Ser Cys
145                 150                 155                 160 gtg ccc ctg atg cga tgc ggg ggc tgc tgc aat gac gag ggc ctg gag       528
Val Pro Leu Met Arg Cys Gly Gly Cys Cys Asn Asp Glu Gly Leu Glu
                165                 170                 175 tgt gtg ccc act gag gag tcc aac atc acc atg cag att atg cgg atc       576
Cys Val Pro Thr Glu Glu Ser Asn Ile Thr Met Gln Ile Met Arg Ile
            180                 185                 190 aaa cct cac caa ggc cag cac ata gga gag atg agc ttc cta cag cac       624
Lys Pro His Gln Gly Gln His Ile Gly Glu Met Ser Phe Leu Gln His
        195                 200                 205 aac aaa tgt gaa tgc aga cca aag aaa gat aga gca aga tga               666
Asn Lys Cys Glu Cys Arg Pro Lys Lys Asp Arg Ala Arg *
    210                 215                 220

<210> SEQ ID NO 4
<211> LENGTH: 221
<212> TYPE: PRT
<213> ORGANISM: Artificial Sequence
<220> FEATURE:
<223> OTHER INFORMATION: Single Chain Vascular Endothelial Growth Factor
      (scVEGF) protein

<400> SEQUENCE: 4

Met Ala Glu Gly Gly Gly Gln Asn His His Glu Val Val Lys Phe Met
1               5                   10                  15

Asp Val Tyr Gln Arg Ser Tyr Cys His Pro Ile Glu Thr Leu Val Asp
            20                  25                  30

Ile Phe Gln Glu Tyr Pro Asp Glu Ile Glu Tyr Ile Phe Lys Pro Ser
        35                  40                  45

Cys Val Pro Leu Met Arg Cys Gly Gly Cys Cys Asn Asp Glu Gly Leu
    50                  55                  60

Glu Cys Val Pro Thr Glu Glu Ser Asn Ile Thr Met Gln Ile Met Arg
65                  70                  75                  80

Ile Lys Pro His Gln Gly Gln His Ile Gly Glu Met Ser Phe Leu Gln
                85                  90                  95

His Asn Lys Cys Glu Cys Arg Pro Lys Lys Asp Arg Ala Arg Ala Met
            100                 105                 110

Ala Glu Gly Gly Gly Gln Asn His His Glu Val Val Lys Phe Met Asp
        115                 120                 125

Val Tyr Gln Arg Ser Tyr Cys His Pro Ile Glu Thr Leu Val Asp Ile
    130                 135                 140

Phe Gln Glu Tyr Pro Asp Glu Ile Glu Tyr Ile Phe Lys Pro Ser Cys
145                 150                 155                 160

Val Pro Leu Met Arg Cys Gly Gly Cys Cys Asn Asp Glu Gly Leu Glu
                165                 170                 175

Cys Val Pro Thr Glu Glu Ser Asn Ile Thr Met Gln Ile Met Arg Ile
            180                 185                 190

Lys Pro His Gln Gly Gln His Ile Gly Glu Met Ser Phe Leu Gln His
        195                 200                 205

Asn Lys Cys Glu Cys Arg Pro Lys Lys Asp Arg Ala Arg
    210                 215                 220

<210> SEQ ID NO 5
<211> LENGTH: 423
<212> TYPE: DNA
<213> ORGANISM: Artificial Sequence
```

<220> FEATURE:
<223> OTHER INFORMATION: C4-VEGF121 construct
<220> FEATURE:
<221> NAME/KEY: CDS
<222> LOCATION: (1)...(423)

<400> SEQUENCE: 5

| | | | | | | | | | | | | | | | | |
|---|---|---|---|---|---|---|---|---|---|---|---|---|---|---|---|---|
| atg | aaa | gaa | tct | tgc | gct | aaa | aaa | ttt | caa | cgt | caa | cac | atg | gac | tct | 48 |
| Met | Lys | Glu | Ser | Cys | Ala | Lys | Lys | Phe | Gln | Arg | Gln | His | Met | Asp | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggt | ggc | ggc | ggt | tcc | atg | gca | gaa | gga | gga | ggg | cag | aat | cat | cac | gaa | 96 |
| Gly | Gly | Gly | Gly | Ser | Met | Ala | Glu | Gly | Gly | Gly | Gln | Asn | His | His | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| gtg | gtg | aag | ttc | atg | gat | gtc | tat | cag | cgc | agc | tac | tgc | cat | cca | atc | 144 |
| Val | Val | Lys | Phe | Met | Asp | Val | Tyr | Gln | Arg | Ser | Tyr | Cys | His | Pro | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| gag | acc | ctg | gtg | gac | atc | ttc | cag | gag | tac | cct | gat | gag | atc | gag | tac | 192 |
| Glu | Thr | Leu | Val | Asp | Ile | Phe | Gln | Glu | Tyr | Pro | Asp | Glu | Ile | Glu | Tyr | |
| | 50 | | | | | 55 | | | | | 60 | | | | | |

| | | | | | | | | | | | | | | | | |
|---|---|---|---|---|---|---|---|---|---|---|---|---|---|---|---|---|
| atc | ttc | aag | cca | tcc | tgt | gtg | ccc | ctg | atg | cga | tgc | ggg | ggc | tgc | tgc | 240 |
| Ile | Phe | Lys | Pro | Ser | Cys | Val | Pro | Leu | Met | Arg | Cys | Gly | Gly | Cys | Cys | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aat | gac | gag | ggc | ctg | gag | tgt | gtg | ccc | act | gag | gag | tcc | aac | atc | acc | 288 |
| Asn | Asp | Glu | Gly | Leu | Glu | Cys | Val | Pro | Thr | Glu | Glu | Ser | Asn | Ile | Thr | |
| | | | 85 | | | | | 90 | | | | | 95 | | | |

| | | | | | | | | | | | | | | | | |
|---|---|---|---|---|---|---|---|---|---|---|---|---|---|---|---|---|
| atg | cag | att | atg | cgg | atc | aaa | cct | cac | caa | ggc | cag | cac | ata | gga | gag | 336 |
| Met | Gln | Ile | Met | Arg | Ile | Lys | Pro | His | Gln | Gly | Gln | His | Ile | Gly | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| atg | agc | ttc | cta | cag | cac | aac | aaa | tgt | gaa | tgc | aga | cca | aag | aaa | gat | 384 |
| Met | Ser | Phe | Leu | Gln | His | Asn | Lys | Cys | Glu | Cys | Arg | Pro | Lys | Lys | Asp | |
| | | 115 | | | | | 120 | | | | | 125 | | | | |

| | | | | | | | | | | | | | |
|---|---|---|---|---|---|---|---|---|---|---|---|---|---|
| aga | gca | aga | caa | gaa | aaa | tgt | gac | aag | ccg | agg | cgg | tga | 423 |
| Arg | Ala | Arg | Gln | Glu | Lys | Cys | Asp | Lys | Pro | Arg | Arg | * | |
| | 130 | | | | | 135 | | | | | 140 | | |

<210> SEQ ID NO 6
<211> LENGTH: 140
<212> TYPE: PRT
<213> ORGANISM: Artificial Sequence
<220> FEATURE:
<223> OTHER INFORMATION: C4-VEGF121 construct

<400> SEQUENCE: 6

Met Lys Glu Ser Cys Ala Lys Lys Phe Gln Arg Gln His Met Asp Ser
1               5                   10                  15

Gly Gly Gly Gly Ser Met Ala Glu Gly Gly Gly Gln Asn His His Glu
            20                  25                  30

Val Val Lys Phe Met Asp Val Tyr Gln Arg Ser Tyr Cys His Pro Ile
        35                  40                  45

Glu Thr Leu Val Asp Ile Phe Gln Glu Tyr Pro Asp Glu Ile Glu Tyr
    50                  55                  60

Ile Phe Lys Pro Ser Cys Val Pro Leu Met Arg Cys Gly Gly Cys Cys
65                  70                  75                  80

Asn Asp Glu Gly Leu Glu Cys Val Pro Thr Glu Glu Ser Asn Ile Thr
                85                  90                  95

Met Gln Ile Met Arg Ile Lys Pro His Gln Gly Gln His Ile Gly Glu
            100                 105                 110

```
Met Ser Phe Leu Gln His Asn Lys Cys Glu Cys Arg Pro Lys Lys Asp
        115                 120                 125

Arg Ala Arg Gln Glu Lys Cys Asp Lys Pro Arg Arg
    130                 135                 140

<210> SEQ ID NO 7
<211> LENGTH: 396
<212> TYPE: DNA
<213> ORGANISM: Artificial Sequence
<220> FEATURE:
<223> OTHER INFORMATION: C4-VEGF110 construct
<220> FEATURE:
<221> NAME/KEY: CDS
<222> LOCATION: (1)...(396)

<400> SEQUENCE: 7 atg aaa gaa tct tgc gct aaa aaa ttt caa cgt caa cac atg gac tct    48
Met Lys Glu Ser Cys Ala Lys Lys Phe Gln Arg Gln His Met Asp Ser
1               5                   10                  15 ggt ggc ggc ggt tcc atg gca gaa gga gga ggg cag aat cat cac gaa    96
Gly Gly Gly Gly Ser Met Ala Glu Gly Gly Gly Gln Asn His His Glu
            20                  25                  30 gtg gtg aag ttc atg gat gtc tat cag cgc agc tac tgc cat cca atc    144
Val Val Lys Phe Met Asp Val Tyr Gln Arg Ser Tyr Cys His Pro Ile
        35                  40                  45 gag acc ctg gtg gac atc ttc cag gag tac cct gat gag atc gag tac    192
Glu Thr Leu Val Asp Ile Phe Gln Glu Tyr Pro Asp Glu Ile Glu Tyr
    50                  55                  60 atc ttc aag cca tcc tgt gtg ccc ctg atg cga tgc ggg ggc tgc tgc    240
Ile Phe Lys Pro Ser Cys Val Pro Leu Met Arg Cys Gly Gly Cys Cys
65                  70                  75                  80 aat gac gag ggc ctg gag tgt gtg ccc act gag gag tcc aac atc acc    288
Asn Asp Glu Gly Leu Glu Cys Val Pro Thr Glu Glu Ser Asn Ile Thr
                85                  90                  95 atg cag att atg cgg atc aaa cct cac caa ggc cag cac ata gga gag    336
Met Gln Ile Met Arg Ile Lys Pro His Gln Gly Gln His Ile Gly Glu
            100                 105                 110 atg agc ttc cta cag cac aac aaa tgt gaa tgc aga cca aag aaa gat    384
Met Ser Phe Leu Gln His Asn Lys Cys Glu Cys Arg Pro Lys Lys Asp
        115                 120                 125 aga gca aga tga                                                    396
Arg Ala Arg *
    130

<210> SEQ ID NO 8
<211> LENGTH: 131
<212> TYPE: PRT
<213> ORGANISM: Human
<220> FEATURE:
<223> OTHER INFORMATION: C4-VEGF110 construct

<400> SEQUENCE: 8

Met Lys Glu Ser Cys Ala Lys Lys Phe Gln Arg Gln His Met Asp Ser
1               5                   10                  15

Gly Gly Gly Gly Ser Met Ala Glu Gly Gly Gly Gln Asn His His Glu
            20                  25                  30

Val Val Lys Phe Met Asp Val Tyr Gln Arg Ser Tyr Cys His Pro Ile
        35                  40                  45

Glu Thr Leu Val Asp Ile Phe Gln Glu Tyr Pro Asp Glu Ile Glu Tyr
    50                  55                  60

Ile Phe Lys Pro Ser Cys Val Pro Leu Met Arg Cys Gly Gly Cys Cys
65                  70                  75                  80
```

```
Asn Asp Glu Gly Leu Glu Cys Val Pro Thr Glu Glu Ser Asn Ile Thr
            85                  90                  95
Met Gln Ile Met Arg Ile Lys Pro His Gln Gly Gln His Ile Gly Glu
            100                 105                 110
Met Ser Phe Leu Gln His Asn Lys Cys Glu Cys Arg Pro Lys Lys Asp
            115                 120                 125
Arg Ala Arg
        130

<210> SEQ ID NO 9
<211> LENGTH: 1056
<212> TYPE: DNA
<213> ORGANISM: Artificial Sequence
<220> FEATURE:
<223> OTHER INFORMATION: C4(G4S)3-Annexin V construct
<220> FEATURE:
<221> NAME/KEY: CDS
<222> LOCATION: (1)...(1056)

<400> SEQUENCE: 9
```

| | | | | | | | | | | | | | | | | |
|---|---|---|---|---|---|---|---|---|---|---|---|---|---|---|---|---|
| atg | aaa | gaa | tct | tgc | gct | aaa | aaa | ttt | caa | cgt | caa | cac | atg | gac | tct | 48 |
| Met | Lys | Glu | Ser | Cys | Ala | Lys | Lys | Phe | Gln | Arg | Gln | His | Met | Asp | Ser | |
| 1 | | | 5 | | | | | 10 | | | | | 15 | | | |
| ggt | ggc | ggc | ggt | agt | ggt | ggt | ggc | ggt | tca | ggc | gga | ggt | ggc | tcc | atg | 96 |
| Gly | Gly | Gly | Gly | Ser | Gly | Gly | Gly | Gly | Ser | Gly | Gly | Gly | Gly | Ser | Met | |
| | | | 20 | | | | | 25 | | | | | 30 | | | |
| gca | cag | gtt | ctc | aga | ggc | act | gtg | act | gac | ttc | cct | gga | ttt | gat | gag | 144 |
| Ala | Gln | Val | Leu | Arg | Gly | Thr | Val | Thr | Asp | Phe | Pro | Gly | Phe | Asp | Glu | |
| | | 35 | | | | | 40 | | | | | 45 | | | | |
| cgg | gct | gat | gca | gaa | act | ctt | cgg | aag | gct | atg | aaa | ggc | ttg | ggc | aca | 192 |
| Arg | Ala | Asp | Ala | Glu | Thr | Leu | Arg | Lys | Ala | Met | Lys | Gly | Leu | Gly | Thr | |
| | 50 | | | | | 55 | | | | | 60 | | | | | |
| gat | gag | gag | agc | atc | ctg | act | ctg | ttg | aca | tcc | cga | agt | aat | gct | cag | 240 |
| Asp | Glu | Glu | Ser | Ile | Leu | Thr | Leu | Leu | Thr | Ser | Arg | Ser | Asn | Ala | Gln | |
| 65 | | | | | 70 | | | | | 75 | | | | | 80 | |
| cgc | cag | gaa | atc | tct | gca | gct | ttt | aag | act | ctg | ttt | ggc | agg | gat | ctt | 288 |
| Arg | Gln | Glu | Ile | Ser | Ala | Ala | Phe | Lys | Thr | Leu | Phe | Gly | Arg | Asp | Leu | |
| | | | | 85 | | | | | 90 | | | | | 95 | | |
| ctg | gat | gac | ctg | aaa | tca | gaa | cta | act | gga | aaa | ttt | gaa | aaa | tta | att | 336 |
| Leu | Asp | Asp | Leu | Lys | Ser | Glu | Leu | Thr | Gly | Lys | Phe | Glu | Lys | Leu | Ile | |
| | | | 100 | | | | | 105 | | | | | 110 | | | |
| gtg | gct | ctg | atg | aaa | ccc | tct | cgg | ctt | tat | gat | gct | tat | gaa | ctg | aaa | 384 |
| Val | Ala | Leu | Met | Lys | Pro | Ser | Arg | Leu | Tyr | Asp | Ala | Tyr | Glu | Leu | Lys | |
| | | 115 | | | | | 120 | | | | | 125 | | | | |
| cat | gcc | ttg | aag | gga | gct | gga | aca | aat | gaa | aaa | gta | ctg | aca | gaa | att | 432 |
| His | Ala | Leu | Lys | Gly | Ala | Gly | Thr | Asn | Glu | Lys | Val | Leu | Thr | Glu | Ile | |
| | 130 | | | | | 135 | | | | | 140 | | | | | |
| att | gct | tca | agg | aca | cct | gaa | gaa | ctg | aga | gcc | atc | aaa | caa | gtt | tat | 480 |
| Ile | Ala | Ser | Arg | Thr | Pro | Glu | Glu | Leu | Arg | Ala | Ile | Lys | Gln | Val | Tyr | |
| 145 | | | | | 150 | | | | | 155 | | | | | 160 | |
| gaa | gaa | gaa | tat | ggc | tca | agc | ctg | gaa | gat | gac | gtg | gtg | ggg | gac | act | 528 |
| Glu | Glu | Glu | Tyr | Gly | Ser | Ser | Leu | Glu | Asp | Asp | Val | Val | Gly | Asp | Thr | |
| | | | | 165 | | | | | 170 | | | | | 175 | | |
| tca | ggg | tac | tac | cag | cgg | atg | ttg | gtg | gtt | ctc | ctt | cag | gct | aac | aga | 576 |
| Ser | Gly | Tyr | Tyr | Gln | Arg | Met | Leu | Val | Val | Leu | Leu | Gln | Ala | Asn | Arg | |
| | | | 180 | | | | | 185 | | | | | 190 | | | |
| gac | cct | gat | gct | gga | att | gat | gaa | gct | caa | gtt | gaa | caa | gat | gct | cag | 624 |
| Asp | Pro | Asp | Ala | Gly | Ile | Asp | Glu | Ala | Gln | Val | Glu | Gln | Asp | Ala | Gln | |
| | | 195 | | | | | 200 | | | | | 205 | | | | |

```
gct tta ttt cag gct gga gaa ctt aaa tgg ggg aca gat gaa gaa aag      672
Ala Leu Phe Gln Ala Gly Glu Leu Lys Trp Gly Thr Asp Glu Glu Lys
    210                 215                 220 ttt atc acc atc ttt gga aca cga agt gtg tct cat ttg aga aag gtg      720
Phe Ile Thr Ile Phe Gly Thr Arg Ser Val Ser His Leu Arg Lys Val
225                 230                 235                 240 ttt gac aag tac atg act ata tca gga ttt caa att gag gaa acc att      768
Phe Asp Lys Tyr Met Thr Ile Ser Gly Phe Gln Ile Glu Glu Thr Ile
                245                 250                 255 gac cgc gag act tct ggc aat tta gag caa cta ctc ctt gct gtt gtg      816
Asp Arg Glu Thr Ser Gly Asn Leu Glu Gln Leu Leu Leu Ala Val Val
            260                 265                 270 aaa tct att cga agt ata cct gcc tac ctt gca gag acc ctc tat tat      864
Lys Ser Ile Arg Ser Ile Pro Ala Tyr Leu Ala Glu Thr Leu Tyr Tyr
        275                 280                 285 gct atg aag gga gct ggg aca gat gat cat acc ctc atc aga gtc atg      912
Ala Met Lys Gly Ala Gly Thr Asp Asp His Thr Leu Ile Arg Val Met
    290                 295                 300 gtt tcc agg agt gag att gat ctg ttt aac atc agg aag gag ttt agg      960
Val Ser Arg Ser Glu Ile Asp Leu Phe Asn Ile Arg Lys Glu Phe Arg
305                 310                 315                 320 aag aat ttt gcc acc tct ctt tat tcc atg att aag gga gat aca tct     1008
Lys Asn Phe Ala Thr Ser Leu Tyr Ser Met Ile Lys Gly Asp Thr Ser
                325                 330                 335 ggg gac tat aag aaa gct ctt ctg ctg ctc tgt gga gaa gat gac taa     1056
Gly Asp Tyr Lys Lys Ala Leu Leu Leu Leu Cys Gly Glu Asp Asp  *
            340                 345                 350

<210> SEQ ID NO 10
<211> LENGTH: 351
<212> TYPE: PRT
<213> ORGANISM: Artificial Sequence
<220> FEATURE:
<223> OTHER INFORMATION: C4(G4S)3-Annexin V construct

<400> SEQUENCE: 10

Met Lys Glu Ser Cys Ala Lys Lys Phe Gln Arg Gln His Met Asp Ser
1               5                   10                  15

Gly Gly Gly Gly Ser Gly Gly Gly Gly Ser Gly Gly Gly Gly Ser Met
                20                  25                  30

Ala Gln Val Leu Arg Gly Thr Val Thr Asp Phe Pro Gly Phe Asp Glu
            35                  40                  45

Arg Ala Asp Ala Glu Thr Leu Arg Lys Ala Met Lys Gly Leu Gly Thr
        50                  55                  60

Asp Glu Glu Ser Ile Leu Thr Leu Leu Thr Ser Arg Ser Asn Ala Gln
65                  70                  75                  80

Arg Gln Glu Ile Ser Ala Ala Phe Lys Thr Leu Phe Gly Arg Asp Leu
                85                  90                  95

Leu Asp Asp Leu Lys Ser Glu Leu Thr Gly Lys Phe Glu Lys Leu Ile
            100                 105                 110

Val Ala Leu Met Lys Pro Ser Arg Leu Tyr Asp Ala Tyr Glu Leu Lys
        115                 120                 125

His Ala Leu Lys Gly Ala Gly Thr Asn Glu Lys Val Leu Thr Glu Ile
    130                 135                 140

Ile Ala Ser Arg Thr Pro Glu Glu Leu Arg Ala Ile Lys Gln Val Tyr
145                 150                 155                 160

Glu Glu Glu Tyr Gly Ser Ser Leu Glu Asp Asp Val Val Gly Asp Thr
                165                 170                 175
```

-continued

```
Ser Gly Tyr Tyr Gln Arg Met Leu Val Val Leu Leu Gln Ala Asn Arg
            180                 185                 190

Asp Pro Asp Ala Gly Ile Asp Glu Ala Gln Val Glu Gln Asp Ala Gln
            195                 200                 205

Ala Leu Phe Gln Ala Gly Glu Leu Lys Trp Gly Thr Asp Glu Glu Lys
            210                 215                 220

Phe Ile Thr Ile Phe Gly Thr Arg Ser Val Ser His Leu Arg Lys Val
225                 230                 235                 240

Phe Asp Lys Tyr Met Thr Ile Ser Gly Phe Gln Ile Glu Glu Thr Ile
                245                 250                 255

Asp Arg Glu Thr Ser Gly Asn Leu Glu Gln Leu Leu Leu Ala Val Val
            260                 265                 270

Lys Ser Ile Arg Ser Ile Pro Ala Tyr Leu Ala Glu Thr Leu Tyr Tyr
            275                 280                 285

Ala Met Lys Gly Ala Gly Thr Asp Asp His Thr Leu Ile Arg Val Met
            290                 295                 300

Val Ser Arg Ser Glu Ile Asp Leu Phe Asn Ile Arg Lys Glu Phe Arg
305                 310                 315                 320

Lys Asn Phe Ala Thr Ser Leu Tyr Ser Met Ile Lys Gly Asp Thr Ser
                325                 330                 335

Gly Asp Tyr Lys Lys Ala Leu Leu Leu Leu Cys Gly Glu Asp
            340                 345                 350

<210> SEQ ID NO 11
<211> LENGTH: 864
<212> TYPE: DNA
<213> ORGANISM: Artificial Sequence
<220> FEATURE:
<223> OTHER INFORMATION: C4(G4S)3-LFn construct
<220> FEATURE:
<221> NAME/KEY: CDS
<222> LOCATION: (1)...(864)

<400> SEQUENCE: 11 atg aaa gaa tct tgc gct aaa aaa ttt caa cgt caa cac atg gac tct      48
Met Lys Glu Ser Cys Ala Lys Lys Phe Gln Arg Gln His Met Asp Ser
1               5                   10                  15 ggt ggc ggc ggt agt ggt ggt ggc ggt tca ggc gga ggt ggc tcc atg      96
Gly Gly Gly Gly Ser Gly Gly Gly Gly Ser Gly Gly Gly Gly Ser Met
                20                  25                  30 gga gcg ggc ggt cat ggt gat gta ggt atg cac gta aaa gag aaa gag     144
Gly Ala Gly Gly His Gly Asp Val Gly Met His Val Lys Glu Lys Glu
            35                  40                  45 aaa aat aaa gat gag aat aag aga aaa gat gaa gaa cga aat aaa aca     192
Lys Asn Lys Asp Glu Asn Lys Arg Lys Asp Glu Glu Arg Asn Lys Thr
        50                  55                  60 cag gaa gag cat tta aag gaa atc atg aaa cac att gta aaa ata gaa     240
Gln Glu Glu His Leu Lys Glu Ile Met Lys His Ile Val Lys Ile Glu
65                  70                  75                  80 gta aaa ggg gag gaa gct gtt aaa aaa gag gca gca gaa aag cta ctt     288
Val Lys Gly Glu Glu Ala Val Lys Lys Glu Ala Ala Glu Lys Leu Leu
                85                  90                  95 gag aaa gta cca tct gat gtt tta gag atg tat aaa gca att gga gga     336
Glu Lys Val Pro Ser Asp Val Leu Glu Met Tyr Lys Ala Ile Gly Gly
            100                 105                 110 aag ata tat att gtg gat ggt gat att aca aaa cat ata tct tta gaa     384
Lys Ile Tyr Ile Val Asp Gly Asp Ile Thr Lys His Ile Ser Leu Glu
        115                 120                 125
```

```
gca tta tct gaa gat aag aaa aaa ata aaa gac att tat ggg aaa gat      432
Ala Leu Ser Glu Asp Lys Lys Lys Ile Lys Asp Ile Tyr Gly Lys Asp
    130                 135                 140 gct tta tta cat gaa cat tat gta tat gca aaa gaa gga tat gaa ccc      480
Ala Leu Leu His Glu His Tyr Val Tyr Ala Lys Glu Gly Tyr Glu Pro
145                 150                 155                 160 gta ctt gta atc caa tct tcg gaa gat tat gta gaa aat act gaa aag      528
Val Leu Val Ile Gln Ser Ser Glu Asp Tyr Val Glu Asn Thr Glu Lys
                165                 170                 175 gca ctg aac gtt tat tat gaa ata ggt aag ata tta tca agg gat att      576
Ala Leu Asn Val Tyr Tyr Glu Ile Gly Lys Ile Leu Ser Arg Asp Ile
            180                 185                 190 tta agt aaa att aat caa cca tat cag aaa ttt tta gat gta tta aat      624
Leu Ser Lys Ile Asn Gln Pro Tyr Gln Lys Phe Leu Asp Val Leu Asn
        195                 200                 205 acc att aaa aat gca tct gat tca gat gga caa gat ctt tta ttt act      672
Thr Ile Lys Asn Ala Ser Asp Ser Asp Gly Gln Asp Leu Leu Phe Thr
    210                 215                 220 aat cag ctt aag gaa cat ccc aca gac ttt tct gta gaa ttc ttg gaa      720
Asn Gln Leu Lys Glu His Pro Thr Asp Phe Ser Val Glu Phe Leu Glu
225                 230                 235                 240 caa aat agc aat gag gta caa gaa gta ttt gcg aaa gct ttt gca tat      768
Gln Asn Ser Asn Glu Val Gln Glu Val Phe Ala Lys Ala Phe Ala Tyr
                245                 250                 255 tat atc gag cca cag cat cgt gat gtt tta cag ctt tat gca ccg gaa      816
Tyr Ile Glu Pro Gln His Arg Asp Val Leu Gln Leu Tyr Ala Pro Glu
            260                 265                 270 gct ttt aat tac atg gat aaa ttt aac gaa caa gaa ata aat cta tag      864
Ala Phe Asn Tyr Met Asp Lys Phe Asn Glu Gln Glu Ile Asn Leu *
        275                 280                 285

<210> SEQ ID NO 12
<211> LENGTH: 287
<212> TYPE: PRT
<213> ORGANISM: Artificial Sequence
<220> FEATURE:
<223> OTHER INFORMATION: C4(G4S)3-LFn construct

<400> SEQUENCE: 12

Met Lys Glu Ser Cys Ala Lys Lys Phe Gln Arg Gln His Met Asp

```
Val Leu Val Ile Gln Ser Ser Glu Asp Tyr Val Glu Asn Thr Glu Lys
            165                 170                 175

Ala Leu Asn Val Tyr Tyr Glu Ile Gly Lys Ile Leu Ser Arg Asp Ile
        180                 185                 190

Leu Ser Lys Ile Asn Gln Pro Tyr Gln Lys Phe Leu Asp Val Leu Asn
    195                 200                 205

Thr Ile Lys Asn Ala Ser Asp Ser Asp Gly Gln Asp Leu Leu Phe Thr
210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu
        275                 280                 285

<210> SEQ ID NO 13
<211> LENGTH: 729
<212> TYPE: DNA
<213> ORGANISM: Artificial Sequence
<220> FEATURE:
<223> OTHER INFORMATION: C4(G4S)3-scVEGF construct
<220> FEATURE:
<221> NAME/KEY: CDS
<222> LOCATION: (1)...(729)

<400> SEQUENCE: 13 atg aaa gaa tct tgc gct aaa aaa ttt caa cgt caa cac atg gac tct      48
Met Lys Glu Ser Cys Ala Lys Lys Phe Gln Arg Gln His Met Asp Ser
1               5                   10                  15 ggt ggc ggc ggt tcc atg gca gaa gga gga ggg cag aat cat cac gaa      96
Gly Gly Gly Gly Ser Met Ala Glu Gly Gly Gly Gln Asn His His Glu
            20                  25                  30 gtg gtg aag ttc atg gat gtc tat cag cgc agc tac tgc cat cca atc     144
Val Val Lys Phe Met Asp Val Tyr Gln Arg Ser Tyr Cys His Pro Ile
        35                  40                  45 gag acc ctg gtg gac atc ttc cag gag tac cct gat gag atc gag tac     192
Glu Thr Leu Val Asp Ile Phe Gln Glu Tyr Pro Asp Glu Ile Glu Tyr
    50                  55                  60 atc ttc aag cca tcc tgt gtg ccc ctg atg cga tgc ggg ggc tgc tgc     240
Ile Phe Lys Pro Ser Cys Val Pro Leu Met Arg Cys Gly Gly Cys Cys
65                  70                  75                  80 aat gac gag ggc ctg gag tgt gtg ccc act gag gag tcc aac atc acc     288
Asn Asp Glu Gly Leu Glu Cys Val Pro Thr Glu Glu Ser Asn Ile Thr
                85                  90                  95 atg cag att atg cgg atc aaa cct cac caa ggc cag cac ata gga gag     336
Met Gln Ile Met Arg Ile Lys Pro His Gln Gly Gln His Ile Gly Glu
            100                 105                 110 atg agc ttc cta cag cac aac aaa tgt gaa tgc aga cca aag aaa gat     384
Met Ser Phe Leu Gln His Asn Lys Cys Glu Cys Arg Pro Lys Lys Asp
        115                 120                 125 aga gca aga gcc atg gca gaa gga gga ggg cag aat cat cac gaa gtg     432
Arg Ala Arg Ala Met Ala Glu Gly Gly Gly Gln Asn His His Glu Val
    130                 135                 140 gtg aag ttc atg gat gtc tat cag cgc agc tac tgc cat cca atc gag     480
Val Lys Phe Met Asp Val Tyr Gln Arg Ser Tyr Cys His Pro Ile Glu
145                 150                 155                 160
```

```
acc ctg gtg gac atc ttc cag gag tac cct gat gag atc gag tac atc    528
Thr Leu Val Asp Ile Phe Gln Glu Tyr Pro Asp Glu Ile Glu Tyr Ile
            165                 170                 175 ttc aag cca tcc tgt gtg ccc ctg atg cga tgc ggg ggc tgc tgc aat    576
Phe Lys Pro Ser Cys Val Pro Leu Met Arg Cys Gly Gly Cys Cys Asn
            180                 185                 190 gac gag ggc ctg gag tgt gtg ccc act gag gag tcc aac atc acc atg    624
Asp Glu Gly Leu Glu Cys Val Pro Thr Glu Glu Ser Asn Ile Thr Met
            195                 200                 205 cag att atg cgg atc aaa cct cac caa ggc cag cac ata gga gag atg    672
Gln Ile Met Arg Ile Lys Pro His Gln Gly Gln His Ile Gly Glu Met
    210                 215                 220 agc ttc cta cag cac aac aaa tgt gaa tgc aga cca aag aaa gat aga    720
Ser Phe Leu Gln His Asn Lys Cys Glu Cys Arg Pro Lys Lys Asp Arg
225                 230                 235                 240 gca aga tga                                                        729
Ala Arg  *

<210> SEQ ID NO 14
<211> LENGTH: 242
<212> TYPE: PRT
<213> ORGANISM: Artificial Sequence
<220> FEATURE:
<223> OTHER INFORMATION: C4(G4S)3-scVEGF construct

<400> SEQUENCE: 14

Met Lys Glu Ser Cys Ala Lys Lys Phe Gln Arg Gln His Met Asp Ser
1               5                   10                  15

Gly Gly Gly Gly Ser Met Ala Glu Gly Gly Gln Asn His His Glu
            20                  25                  30

Val Val Lys Phe Met Asp Val Tyr Gln Arg Ser Tyr Cys His Pro Ile
            35                  40                  45

Glu Thr Leu Val Asp Ile Phe Gln Glu Tyr Pro Asp Glu Ile Glu Tyr
    50                  55                  60

Ile Phe Lys Pro Ser Cys Val Pro Leu Met Arg Cys Gly Gly Cys Cys
65                  70                  75                  80

Asn Asp Glu Gly Leu Glu Cys Val Pro Thr Glu Glu Ser Asn Ile Thr
                85                  90                  95

Met Gln Ile Met Arg Ile Lys Pro His Gln Gly Gln His Ile Gly Glu
            100                 105                 110

Met Ser Phe Leu Gln His Asn Lys Cys Glu Cys Arg Pro Lys Lys Asp
        115                 120                 125

Arg Ala Arg Ala Met Ala Glu Gly Gly Gln Asn His His Glu Val
    130                 135                 140

Val Lys Phe Met Asp Val Tyr Gln Arg Ser Tyr Cys His Pro Ile Glu
145                 150                 155                 160

Thr Leu Val Asp Ile Phe Gln Glu Tyr Pro Asp Glu Ile Glu Tyr Ile
                165                 170                 175

Phe Lys Pro Ser Cys Val Pro Leu Met Arg Cys Gly Gly Cys Cys Asn
            180                 185                 190

Asp Glu Gly Leu Glu Cys Val Pro Thr Glu Glu Ser Asn Ile Thr Met
        195                 200                 205

Gln Ile Met Arg Ile Lys Pro His Gln Gly Gln His Ile Gly Glu Met
    210                 215                 220
```

Ser Phe Leu Gln His Asn Lys Cys Glu Cys Arg Pro Lys Lys Asp Arg
225                 230                 235                 240

Ala Arg

<210> SEQ ID NO 15
<211> LENGTH: 324
<212> TYPE: DNA
<213> ORGANISM: Artificial Sequence
<220> FEATURE:
<223> OTHER INFORMATION: HuS (C118)
<220> FEATURE:
<221> NAME/KEY: CDS
<222> LOCATION: (1)...(324)

<400> SEQUENCE: 15

```
agc agc tcc aac tac tgc aac cag atg atg cgt cgt cgt aac atg acc      48
Ser Ser Ser Asn Tyr Cys Asn Gln Met Met Arg Arg Arg Asn Met Thr
1               5                   10                  15 caa ggt cgt tgc aaa ccg gtg aac act ttc gtt cat gaa ccg ctt gta      96
Gln Gly Arg Cys Lys Pro Val Asn Thr Phe Val His Glu Pro Leu Val
                20                  25                  30 gac gtt cag aac gtt tgc ttc caa gag aag gtt acc tgc aaa aat ggc     144
Asp Val Gln Asn Val Cys Phe Gln Glu Lys Val Thr Cys Lys Asn Gly
            35                  40                  45 cag ggt aac tgc tac aaa tct aac tct tct atg cat atc act gac tgc     192
Gln Gly Asn Cys Tyr Lys Ser Asn Ser Ser Met His Ile Thr Asp Cys
        50                  55                  60 cgt ctt act aac gga tcc cgt tac ccc aac tgc gct tac cgt act tct     240
Arg Leu Thr Asn Gly Ser Arg Tyr Pro Asn Cys Ala Tyr Arg Thr Ser
65                  70                  75                  80 cct aag gaa cgt cat atc atc gtt gca tgc gaa ggc tct ccg tac gtt     288
Pro Lys Glu Arg His Ile Ile Val Ala Cys Glu Gly Ser Pro Tyr Val
                85                  90                  95 ccg tgt cat ttc gac gcg tct gtt gaa gac tct tga                     324
Pro Cys His Phe Asp Ala Ser Val Glu Asp Ser *
                100                 105
```

<210> SEQ ID NO 16
<211> LENGTH: 107
<212> TYPE: PRT
<213> ORGANISM: Artificial Sequence
<220> FEATURE:
<223> OTHER INFORMATION: HuS (C118)

<400> SEQUENCE: 16

Ser Ser Ser Asn Tyr Cys Asn Gln Met Met Arg Arg Arg Asn Met Thr
1               5                   10                  15

Gln Gly Arg Cys Lys Pro Val Asn Thr Phe Val His Glu Pro Leu Val
                20                  25                  30

Asp Val Gln Asn Val Cys Phe Gln Glu Lys Val Thr Cys Lys Asn Gly
            35                  40                  45

Gln Gly Asn Cys Tyr Lys Ser Asn Ser Ser Met His Ile Thr Asp Cys
        50                  55                  60

Arg Leu Thr Asn Gly Ser Arg Tyr Pro Asn Cys Ala Tyr Arg Thr Ser
65                  70                  75                  80

Pro Lys Glu Arg His Ile Ile Val Ala Cys Glu Gly Ser Pro Tyr Val
                85                  90                  95

Pro Cys His Phe Asp Ala Ser Val Glu Asp Ser
                100                 105

-continued

```
<210> SEQ ID NO 17
<211> LENGTH: 324
<212> TYPE: DNA
<213> ORGANISM: Artificial Sequence
<220> FEATURE:
<223> OTHER INFORMATION: HuS (C88, C118)
<220> FEATURE:
<221> NAME/KEY: CDS
<222> LOCATION: (1)...(324)

<400> SEQUENCE: 17 agc agc tcc aac tac tgc aac cag atg atg cgt cgt cgt aac atg acc      48
Ser Ser Ser Asn Tyr Cys Asn Gln Met Met Arg Arg Arg Asn Met Thr
1               5                   10                  15 caa ggt cgt tgc aaa ccg gtg aac act ttc gtt cat gaa ccg ctt gta      96
Gln Gly Arg Cys Lys Pro Val Asn Thr Phe Val His Glu Pro Leu Val
            20                  25                  30 gac gtt cag aac gtt tgc ttc caa gag aag gtt acc tgc aaa aat ggc     144
Asp Val Gln Asn Val Cys Phe Gln Glu Lys Val Thr Cys Lys Asn Gly
        35                  40                  45 cag ggt aac tgc tac aaa tct aac tct tct atg cat atc act gac tgc     192
Gln Gly Asn Cys Tyr Lys Ser Asn Ser Ser Met His Ile Thr Asp Cys
    50                  55                  60 cgt ctt act tgc gga tcc cgt tac ccc aac tgc gct tac cgt act tct     240
Arg Leu Thr Cys Gly Ser Arg Tyr Pro Asn Cys Ala Tyr Arg Thr Ser
65                  70                  75                  80 cct aag gaa cgt cat atc atc gtt gca tgc gaa ggc tct ccg tac gtt     288
Pro Lys Glu Arg His Ile Ile Val Ala Cys Glu Gly Ser Pro Tyr Val
                85                  90                  95 ccg tgt cat ttc gac gcg tct gtt gaa gac tct tga                     324
Pro Cys His Phe Asp Ala Ser Val Glu Asp Ser  *
                100                 105

<210> SEQ ID NO 18
<211> LENGTH: 107
<212> TYPE: PRT
<213> ORGANISM: Artificial Sequence
<220> FEATURE:
<223> OTHER INFORMATION: HuS (C88, C118)

<400> SEQUENCE: 18

Ser Ser Ser Asn Tyr Cys Asn Gln Met Met Arg Arg Arg Asn Met Thr
1               5                   10                  15

Gln Gly Arg Cys Lys Pro Val Asn Thr Phe Val His Glu Pro Leu Val
            20                  25                  30

Asp Val Gln Asn Val Cys Phe Gln Glu Lys Val Thr Cys Lys Asn Gly
        35                  40                  45

Gln Gly Asn Cys Tyr Lys Ser Asn Ser Ser Met His Ile Thr Asp Cys
    50                  55                  60

Arg Leu Thr Cys Gly Ser Arg Tyr Pro Asn Cys Ala Tyr Arg Thr Ser
65                  70                  75                  80

Pro Lys Glu Arg His Ile Ile Val Ala Cys Glu Gly Ser Pro Tyr Val
                85                  90                  95

Pro Cys His Phe Asp Ala Ser Val Glu Asp Ser
                100                 105

<210> SEQ ID NO 19
<211> LENGTH: 387
<212> TYPE: DNA
<213> ORGANISM: Artificial Sequence
<220> FEATURE:
<223> OTHER INFORMATION: BHR (A8, P11, C118)
```

```
<220> FEATURE:
<221> NAME/KEY: CDS
<222> LOCATION: (1)...(387)

<400> SEQUENCE: 19 atg aag gaa act gca gca gcc aag gct gag cgg ccg cac atg gac tcc         48
Met Lys Glu Thr Ala Ala Ala Lys Ala Glu Arg Pro His Met Asp Ser
1               5                   10                  15 agc act tcc gct gcc agc agc tcc aac tac tgc aac cag atg atg cgt         96
Ser Thr Ser Ala Ala Ser Ser Ser Asn Tyr Cys Asn Gln Met Met Arg
                20                  25                  30 cgt cgt aac atg acc caa ggt cgt tgc aaa ccg gtg aac act ttc gtt        144
Arg Arg Asn Met Thr Gln Gly Arg Cys Lys Pro Val Asn Thr Phe Val
            35                  40                  45 cat gaa ccg ctt gta gac gtt cag aac gtt tgc ttc caa gag aag gtt        192
His Glu Pro Leu Val Asp Val Gln Asn Val Cys Phe Gln Glu Lys Val
        50                  55                  60 acc tgc aaa aat ggc cag ggt aac tgc tac aaa tct aac tct tct atg        240
Thr Cys Lys Asn Gly Gln Gly Asn Cys Tyr Lys Ser Asn Ser Ser Met
65                  70                  75                  80 cat atc act gac tgc cgt ctt act aac gga tcc cgt tac ccc aac tgc        288
His Ile Thr Asp Cys Arg Leu Thr Asn Gly Ser Arg Tyr Pro Asn Cys
                85                  90                  95 gct tac cgt act tct cct aag gaa cgt cat atc atc gtt gca tgc gaa        336
Ala Tyr Arg Thr Ser Pro Lys Glu Arg His Ile Ile Val Ala Cys Glu
            100                 105                 110 ggc tct ccg tac gtt ccg tgt cat ttc gac gcg tct gtt gaa gac tct        384
Gly Ser Pro Tyr Val Pro Cys His Phe Asp Ala Ser Val Glu Asp Ser
        115                 120                 125 tga                                                                     387
*

<210> SEQ ID NO 20
<211> LENGTH: 128
<212> TYPE: PRT
<213> ORGANISM: Artificial Sequence
<220> FEATURE:
<223> OTHER INFORMATION: BHR (A8, P11, C118)

<400> SEQUENCE: 20

Met Lys Glu Thr Ala Ala Ala Lys Ala Glu Arg Pro His Met Asp Ser
1               5                   10                  15

Ser Thr Ser Ala Ala Ser Ser Ser Asn Tyr Cys Asn Gln Met Met Arg
                20                  25                  30

Arg Arg Asn Met Thr Gln Gly Arg Cys Lys Pro Val Asn Thr Phe Val
            35                  40                  45

His Glu Pro Leu Val Asp Val Gln Asn Val Cys Phe Gln Glu Lys Val
        50                  55                  60

Thr Cys Lys Asn Gly Gln Gly Asn Cys Tyr Lys Ser Asn Ser Ser Met
65                  70                  75                  80

His Ile Thr Asp Cys Arg Leu Thr Asn Gly Ser Arg Tyr Pro Asn Cys
                85                  90                  95

Ala Tyr Arg Thr Ser Pro Lys Glu Arg His Ile Ile Val Ala Cys Glu
            100                 105                 110

Gly Ser Pro Tyr Val Pro Cys His Phe Asp Ala Ser Val Glu Asp Ser
        115                 120                 125
```

<210> SEQ ID NO 21
<211> LENGTH: 387
<212> TYPE: DNA
<213> ORGANISM: Artificial Sequence
<220> FEATURE:
<223> OTHER INFORMATION: BHR (A8, P11, C88, C118)
<220> FEATURE:
<221> NAME/KEY: CDS
<222> LOCATION: (1)...(387)

<400> SEQUENCE: 21

| atg aag gaa act gca gca gcc aag gct gag cgg ccg cac atg gac tcc | 48 |
| Met Lys Glu Thr Ala Ala Ala Lys Ala Glu Arg Pro His Met Asp Ser | |
| 1               5                   10                  15     | |

| agc act tcc gct gcc agc agc tcc aac tac tgc aac cag atg atg cgt | 96 |
| Ser Thr Ser Ala Ala Ser Ser Ser Asn Tyr Cys Asn Gln Met Met Arg | |
|             20                  25                  30         | |

| cgt cgt aac atg acc caa ggt cgt tgc aaa ccg gtg aac act ttc gtt | 144 |
| Arg Arg Asn Met Thr Gln Gly Arg Cys Lys Pro Val Asn Thr Phe Val | |
|         35                  40                  45             | |

| cat gaa ccg ctt gta gac gtt cag aac gtt tgc ttc caa gag aag gtt | 192 |
| His Glu Pro Leu Val Asp Val Gln Asn Val Cys Phe Gln Glu Lys Val | |
|     50                  55                  60                 | |

| acc tgc aaa aat ggc cag ggt aac tgc tac aaa tct aac tct tct atg | 240 |
| Thr Cys Lys Asn Gly Gln Gly Asn Cys Tyr Lys Ser Asn Ser Ser Met | |
| 65                  70                  75                  80 | |

| cat atc act gac tgc cgt ctt act tgc gga tcc cgt tac ccc aac tgc | 288 |
| His Ile Thr Asp Cys Arg Leu Thr Cys Gly Ser Arg Tyr Pro Asn Cys | |
|                 85                  90                  95     | |

| gct tac cgt act tct cct aag gaa cgt cat atc atc gtt gca tgc gaa | 336 |
| Ala Tyr Arg Thr Ser Pro Lys Glu Arg His Ile Ile Val Ala Cys Glu | |
|             100                 105                 110        | |

| ggc tct ccg tac gtt ccg tgt cat ttc gac gcg tct gtt gaa gac tct | 384 |
| Gly Ser Pro Tyr Val Pro Cys His Phe Asp Ala Ser Val Glu Asp Ser | |
|         115                 120                 125            | |

| tga | 387 |
| *   |     |

<210> SEQ ID NO 22
<211> LENGTH: 128
<212> TYPE: PRT
<213> ORGANISM: Artificial Sequence
<220> FEATURE:
<223> OTHER INFORMATION: BHR (A8, P11, C88, C118)

<400> SEQUENCE: 22

Met Lys Glu Thr Ala Ala Ala Lys Ala Glu Arg Pro His Met Asp Ser
1               5                   10                  15

Ser Thr Ser Ala Ala Ser Ser Ser Asn Tyr Cys Asn Gln Met Met Arg
            20                  25                  30

Arg Arg Asn Met Thr Gln Gly Arg Cys Lys Pro Val Asn Thr Phe Val
        35                  40                  45

His Glu Pro Leu Val Asp Val Gln Asn Val Cys Phe Gln Glu Lys Val
    50                  55                  60

Thr Cys Lys Asn Gly Gln Gly Asn Cys Tyr Lys Ser Asn Ser Ser Met
65                  70                  75                  80

His Ile Thr Asp Cys Arg Leu Thr Cys Gly Ser Arg Tyr Pro Asn Cys
                85                  90                  95

-continued

```
Ala Tyr Arg Thr Ser Pro Lys Glu Arg His Ile Ile Val Ala Cys Glu
            100                 105                 110

Gly Ser Pro Tyr Val Pro Cys His Phe Asp Ala Ser Val Glu Asp Ser
        115                 120                 125

<210> SEQ ID NO 23
<211> LENGTH: 36
<212> TYPE: DNA
<213> ORGANISM: Artificial Sequence
<220> FEATURE:
<223> OTHER INFORMATION: Primer Sequence

<400> SEQUENCE: 23
atatacatat gaaagaatct tgcgctaaaa aatttc                             36

<210> SEQ ID NO 24
<211> LENGTH: 35
<212> TYPE: DNA
<213> ORGANISM: Artificial Sequence
<220> FEATURE:
<223> OTHER INFORMATION: Primer Sequence

<400> SEQUENCE: 24
agattctttc atatgtatat ctccttctta aagtt                              35

<210> SEQ ID NO 25
<211> LENGTH: 37
<212> TYPE: DNA
<213> ORGANISM: Artificial Sequence
<220> FEATURE:
<223> OTHER INFORMATION: Primer Sequence

<400> SEQUENCE: 25
ggataacaat tcccctctag aaataatttt gtttaac                            37

<210> SEQ ID NO 26
<211> LENGTH: 34
<212> TYPE: DNA
<213> ORGANISM: Artificial Sequence
<220> FEATURE:
<223> OTHER INFORMATION: Primer Sequence

<400> SEQUENCE: 26
actacccatg gaaccgccgc caccagagtc catg                               34

<210> SEQ ID NO 27
<211> LENGTH: 32
<212> TYPE: DNA
<213> ORGANISM: Artificial Sequence
<220> FEATURE:
<223> OTHER INFORMATION: Primer Sequence

<400> SEQUENCE: 27
cacaagccat ggcacccatg gcagaaggag ga                                 32

<210> SEQ ID NO 28
<211> LENGTH: 31
<212> TYPE: DNA
<213> ORGANISM: Artificial Sequence
<220> FEATURE:
<223> OTHER INFORMATION: Primer Sequence

<400> SEQUENCE: 28
actacccatg gtcaccgcct cggcttgtca c                                  31
```

<210> SEQ ID NO 29
<211> LENGTH: 32
<212> TYPE: DNA
<213> ORGANISM: Artificial Sequence
<220> FEATURE:
<223> OTHER INFORMATION: Primer Sequence

<400> SEQUENCE: 29
ctgctccatg ggagcgggcg gtcatggtga tg                          32

<210> SEQ ID NO 30
<211> LENGTH: 44
<212> TYPE: DNA
<213> ORGANISM: Artificial Sequence
<220> FEATURE:
<223> OTHER INFORMATION: Primer Sequence

<400> SEQUENCE: 30
actacccatg gctatagatt tatttcttgt tcgttaaatt tatc              44

<210> SEQ ID NO 31
<211> LENGTH: 27
<212> TYPE: DNA
<213> ORGANISM: Artificial Sequence
<220> FEATURE:
<223> OTHER INFORMATION: Primer Sequence

<400> SEQUENCE: 31
cacaagccat ggcacaggtt ctcagag                                27

<210> SEQ ID NO 32
<211> LENGTH: 33
<212> TYPE: DNA
<213> ORGANISM: Artificial Sequence
<220> FEATURE:
<223> OTHER INFORMATION: Primer Sequence

<400> SEQUENCE: 32
actacccatg gttagtcatc ttctccacag agc                         33

<210> SEQ ID NO 33
<211> LENGTH: 27
<212> TYPE: DNA
<213> ORGANISM: Artificial Sequence
<220> FEATURE:
<223> OTHER INFORMATION: Primer Sequence

<400> SEQUENCE: 33
cacggatccg gtggcggcgg tagtggt                                27

<210> SEQ ID NO 34
<211> LENGTH: 38
<212> TYPE: DNA
<213> ORGANISM: Artificial Sequence
<220> FEATURE:
<223> OTHER INFORMATION: Primer Sequence

<400> SEQUENCE: 34
cacggatcct catcttgctc tatctttctt tggtctgc                    38

<210> SEQ ID NO 35
<211> LENGTH: 32
<212> TYPE: DNA
<213> ORGANISM: Artificial Sequence
<220> FEATURE:
<223> OTHER INFORMATION: Primer Sequence

```
<400> SEQUENCE: 35
cacaagccat ggcacccatg gcagaaggag ga                                    32

<210> SEQ ID NO 36
<211> LENGTH: 38
<212> TYPE: DNA
<213> ORGANISM: Artificial Sequence
<220> FEATURE:
<223> OTHER INFORMATION: Primer Sequence

<400> SEQUENCE: 36
actacccatg gctcttgctc tatctttctt tggtctgc                              38

<210> SEQ ID NO 37
<211> LENGTH: 35
<212> TYPE: DNA
<213> ORGANISM: Artificial Sequence
<220> FEATURE:
<223> OTHER INFORMATION: Primer Sequence

<400> SEQUENCE: 37
aaggctctcc gtacgttccg tgtcatttcg acgcg                                 35

<210> SEQ ID NO 38
<211> LENGTH: 30
<212> TYPE: DNA
<213> ORGANISM: Artificial Sequence
<220> FEATURE:
<223> OTHER INFORMATION: Primer Sequence

<400> SEQUENCE: 38
cggaacgtac ggagagcctt cgcatgcaac                                       30

<210> SEQ ID NO 39
<211> LENGTH: 33
<212> TYPE: DNA
<213> ORGANISM: Artificial Sequence
<220> FEATURE:
<223> OTHER INFORMATION: Primer Sequence

<400> SEQUENCE: 39
tcactgactg ccgtcttact tgcggatccc gtt                                   33

<210> SEQ ID NO 40
<211> LENGTH: 31
<212> TYPE: DNA
<213> ORGANISM: Artificial Sequence
<220> FEATURE:
<223> OTHER INFORMATION: Primer Sequence

<400> SEQUENCE: 40
agtaagacgg cagtcagtga tatgcataga a                                     31

<210> SEQ ID NO 41
<211> LENGTH: 32
<212> TYPE: DNA
<213> ORGANISM: Artificial Sequence
<220> FEATURE:
<223> OTHER INFORMATION: Primer Sequence

<400> SEQUENCE: 41
gcagccaagt ttgagcggcc gcacatggac tc                                    32
```

-continued

```
<210> SEQ ID NO 42
<211> LENGTH: 31
<212> TYPE: DNA
<213> ORGANISM: Artificial Sequence
<220> FEATURE:
<223> OTHER INFORMATION: Primer Sequence

<400> SEQUENCE: 42
gccgctcaaa cttggctgct gcagtttcct t                              31

<210> SEQ ID NO 43
<211> LENGTH: 32
<212> TYPE: DNA
<213> ORGANISM: Artificial Sequence
<220> FEATURE:
<223> OTHER INFORMATION: Primer Sequence

<400> SEQUENCE: 43
ggaaactgca gcagccaagg ctgagcggcc gc                             32

<210> SEQ ID NO 44
<211> LENGTH: 32
<212> TYPE: DNA
<213> ORGANISM: Artificial Sequence
<220> FEATURE:
<223> OTHER INFORMATION: Primer Sequence

<400> SEQUENCE: 44
cttggctgct gcagtttcct tcatatgtat at                             32

<210> SEQ ID NO 45
<211> LENGTH: 35
<212> TYPE: DNA
<213> ORGANISM: Artificial Sequence
<220> FEATURE:
<223> OTHER INFORMATION: Primer Sequence

<400> SEQUENCE: 45
aaaaacatat gaaggaattt accttagact tctcg                          35

<210> SEQ ID NO 46
<211> LENGTH: 28
<212> TYPE: DNA
<213> ORGANISM: Artificial Sequence
<220> FEATURE:
<223> OTHER INFORMATION: Primer Sequence

<400> SEQUENCE: 46
tactcgagtc accgcctcgg cttgtcac                                  28
```

CYSTEINE-CONTAINING PEPTIDE TAG FOR SITE-SPECIFIC CONJUGATION OF PROTEINS

CROSS-REFERENCE TO RELATED APPLICATIONS

This application is a Divisional of U.S. patent application Ser. No. 11/083,508 filed Mar. 18, 2005, now U.S. Pat. No. 7,355,019, which is a Continuation-in-Part Application of U.S. Ser. No. 09/872,712 filed Jun. 1, 2001 now abandoned, which claims the benefit of U.S. Provisional Application 60/209,660 filed Jun. 6, 2000. All the aforementioned U.S. Applications are incorporated by reference herein in their entireties.

STATEMENT OF GOVERNMENT SUPPORT

This invention was made in part with government support under grant numbers 1R43 HL61143-01; 1-R43-CA113080-01; R43AI054060-01; and 1R43 GM072170-01 from the National Institutes of Health, and grant number DE-FG-02-02ER83520 from the Department of Energy. The government has certain rights in this invention.

BACKGROUND OF THE INVENTION

1. Field of the Invention

The present invention is directed to nucleic acid and protein sequences that encode a cysteine-containing tag and a targeting protein. The present invention is also directed to a biological conjugate comprising proteins having the above protein sequences and a binding moiety covalently bound to the cysteine-containing tag in the protein. The present invention is also directed to pharmaceutical compositions containing the biological conjugates in combination with selected therapeutic, diagnostic, or research entities, and methods of administering the pharmaceutical compositions to a patient to achieve targeted delivery of the therapeutic, diagnostic, or research entities in the patient.

2. Description of the Related Art

Conjugation of recombinant proteins to various entities is used in several areas. One area is targeted delivery of therapeutic, diagnostic, and research agents to targeted cells in the patient in order to improve their efficacy and to minimize potentially adverse side effects. In this area either therapeutic, diagnostic, and research agents, or their carriers are chemically conjugated to recombinant targeting proteins that can selectively bind to targeted cells (reviewed by Dubowchik & Walker, 1999). The resulting conjugates are structurally and functionally heterogeneous because they are formed randomly via chemical reactions with few of several available chemical groups, usually ε-amino groups of lysine residues, in the targeting protein. Since random conjugation does not discriminate between functionally important and dispensable amino acid residues in the targeting protein, the procedure should be custom-developed and optimized on a case-by-case basis in order to increase the proportion of functionally active proteins.

Another area is derivatizing artificial surfaces and/or bulk compositions of biomedical devices or tissue scaffolds with proteins that target certain components of intra-organism environment in order to improve surface compatibility with the environment and to modulate the desired features, such as affinity or rejection of certain intra-organism components. In this area recombinant proteins are covalently grafted on the material through random chemical conjugation, usually via ε-amino groups of lysine residues, that involves both functionally important and dispensable amino acid residues in the proteins, resulting in heterogeneous products with unknown fraction of functionally active proteins.

Yet another area with similar problems is construction of various biosensors or other functional devices with protein-derivatized surfaces that convert the results of interactions between the "working" protein and the targeted components of the environment into a detectable output, including but not limited to a detectable signal or the products of enzymatic activity of immobilized proteins. In this area recombinant proteins are also chemically conjugated to artificial surfaces of these devices usually via ε-amino groups of lysine residues, yielding heterogeneous surfaces with unknown fraction of functionally active proteins.

Several methods for chemical conjugation of proteins to artificial surfaces have been developed (see, for example U.S. Pat. Nos. 5,492,840 to Malmqvuist; 5,853,744 to Mooradian et al.; 6,033,719 to Keogh, Mann et al. (2001); Kuhl & Griffith-Cima, (1996); Bentz et al. (1998). These methods were developed on a case-by-case basis in order to minimize damage to the protein and to increase the homogeneity of the surface.

These problems are well recognized, and over the years several approaches have been developed for introduction into recombinant proteins of unique cysteine residues for site-specific conjugation of various entities. This strategy is based on observation that intrinsic cysteine residues in proteins are usually involved in intramolecular or inter-subunit disulfide bonds and are not readily available for chemical conjugation. In theory, introduction of a unique cysteine residue that does not affect formation of intrinsic disulfide bonds and does not affect functional activity of the recombinant protein can provide a thiol group available for site-specific conjugation via chemistries known in art. For example, several groups reported introduction of cysteines into recombinant single-chain Fv antibody fragments (scFv), usually at or near C-termini, in order to use these cysteine residues for formation of diabodies and/or for site-specific conjugation to various entities (Adams et al., 1993; Kipriyanov et al., 1994; Wang et al., 1997; Marti et al., 2001; Gupta et al., 2001; Xu et al., 2002; Li et al., 2002; Renard et al., 2002; Albrecht et al., 2004). However, even for scFv, the presence of unpaired cysteine at or near the C-terminus significantly affects protein yield, solubility and functional activity (Schmiedl et al., 2000). Futami et al. (2000) introduced cysteine residues near the N- and C-termini of into human RNase I which resulted in a stabilized RNase I. However, yield and enzymatic activity of the product were significantly reduced. Moreover, this mutant RNase I or its fragments were not used in other products.

Another method for site directed modification of proteins is intein-mediated ligation of various entities to the C-terminus of the protein (see, for example Evans et al., 1999; Tolbert and Wong 2000; Macmillan et al., 2000; Mukhopadhyay et al., 2001; Hofinann, and Muir, 2002; Lovrinovic et al., 2003; Wood et al., 2004). However application of this method require proper folding of the protein fused to a large intein domain and the ability to withstand fairly harsh reducing conditions during intein-mediated ligation. Furthermore, in both approaches discussed above, conjugation to available cysteine residue is limited to entities that do not interfere with activities of the protein despite their close proximity to the body of the protein.

Thus, in the area of protein-based targeted delivery of therapeutic, diagnostic, and research compounds, as well as in the area of construction of various devices and scaffolds with protein-derivatized surfaces, what is needed in the art are compositions and general methods that (1) allow for site-specific conjugation of recombinant proteins to various entities in order to produce more homogeneous products in ways that minimize interference with functional activities of said proteins; (2) readily convert various recombinant proteins of interest into a format suitable for site-specific conjugation; (3) can be utilized with a wide variety of entities to which a recombinant protein of interest need to be conjugated; and (4) do not result in immunogenic or toxicity problems when introduced into humans. The present invention is believed to be an answer to these objectives.

SUMMARY OF THE INVENTION

In one aspect, the present invention is directed to an isolated polypeptide, consisting of the sequence of SEQ ID NO:2.

In another aspect, the present invention is directed to an isolated nucleic acid consisting of a nucleic acid sequence that encodes the polypeptide sequence of SEQ ID NO:2.

In another aspect, the present invention is directed to an isolated polypeptide, comprising the sequence of SEQ ID NO:4.

In another aspect, the present invention is directed to an isolated nucleic acid comprising a sequence that encodes the polypeptide sequence of SEQ ID NO:4.

In another aspect, the present invention is directed to an isolated polypeptide having an amino acid sequence comprising the polypeptide sequence of SEQ ID NO:2 and the polypeptide sequence of a selected targeting protein.

In another aspect, the present invention is directed to an isolated nucleic acid encoding the polypeptide sequence of SEQ ID NO:6, 8, 10, 12, or 14.

In another aspect, the present invention is directed to a biological conjugate, comprising: (a) a targeting moiety comprising a polypeptide having an amino acid sequence comprising the polypeptide sequence of SEQ ID NO:2 and the polypeptide sequence of a selected targeting protein; and (b) a binding moiety; the biological conjugate having a covalent bond between the thiol group of SEQ ID NO:2 and a functional group in the binding moiety.

In another aspect, the present invention is directed to a biological conjugate, comprising: (a) a targeting moiety comprising a polypeptide having an amino acid sequence comprising the polypeptide sequence of SEQ ID NO:2 and the polypeptide sequence of a selected targeting protein; and (b) a binding moiety that comprises an adapter protein bound covalently to the targeting moiety, the adapter protein having a thiol group; the biological conjugate having a disulfide bond between the thiol group of SEQ ID NO:2 and the thiol group of the adapter protein.

In another aspect, the present invention is directed to a pharmaceutical composition for selectively delivering selected entities to a target in a patient, comprising a pharmaceutically acceptable carrier; and one or another of the above biological conjugates.

In another aspect, the present invention is directed to a method of selectively delivering entities to a target in a patient, comprising the steps of: (a) administering to a patient the above pharmaceutical composition; and (b) permitting the biological conjugate to contact the target to deliver the entity to the target in the patient.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1A:
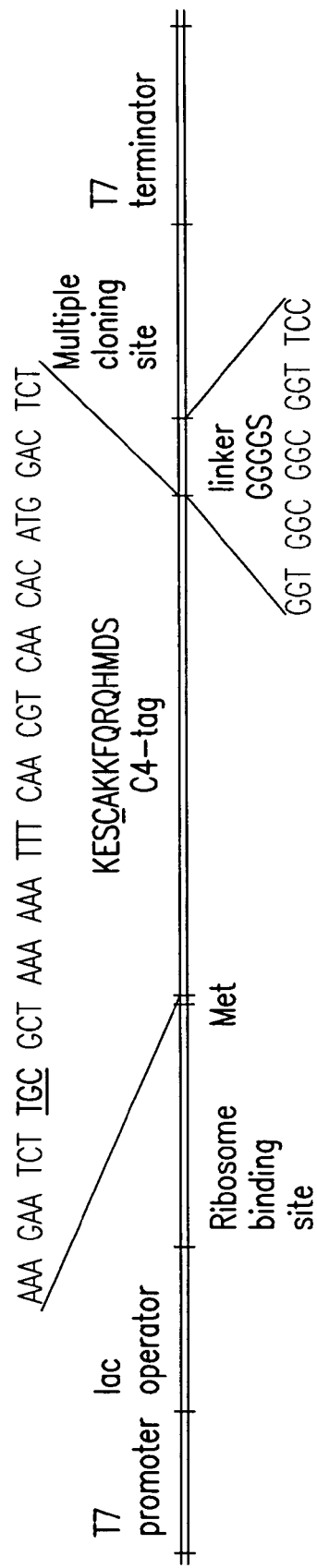
FIG. 1 is a representation of amino acid and nucleic acid sequences of C4-tag genetically fused to multiple cloning site region via a G4S linker (Panel A), and a schematic representation of a plasmid for bacterial expression of fusion recombinant proteins fused to C4-tag via a G4S linker (Panel B)

As indicated above, the present invention comprises compositions and methods useful for site-specific conjugation of recombinant fusion proteins to various entities via a single cysteine residue present in a peptide tag engineered into the protein. Current conjugation methods known in the art rely mostly on random cross-linking of various entities to amino acid residues, such as, for example, lysine or tyrosine, that are abundant in the protein. Less abundant cysteine residues are usually involved in intramolecular disulfide bonds essential for the functional activity of the protein and therefore not available for conjugation. As a result, even when conjugation involves only one amino acid residue per protein, the final product contains a mixture of proteins modified at different positions and therefore heterogeneous in their activity, pharmacokinetics, pharmacodynamic, and tissue distribution characteristics. Furthermore, conjugation to amino acid residues in the protein is always limited by the harm it may inflict upon the functional activity of the proteins. As a result, conjugation procedures have to be custom-developed on a case-by-case basis. However, customized conjugation does not allow a standardized approach to rapid adaptation of different proteins for similar purposes, for example for a targeted delivery of the same imaging reagent, or surface derivatization of the same device.

To overcome these and other obstacles, the present invention discloses compositions and methods useful for site-specific conjugation of recombinant proteins to various entities. The method is based on conversion of a protein of interest into a fusion protein that comprises a cysteine-containing peptide tag, named C4, fused via a linker peptide to an N-terminus or a C-terminus of the protein of interest. By definition, in order to be useful, such fusion proteins should retain its functional activities, and a cysteine residue in the peptide tag should be available for site-specific conjugation with various entities, including complimentary adapter proteins, capable of forming a covalent disulfide bond with tag's cysteine. Various chemistries for conjugation to a cysteine thiol group are well-known in art. For example, entities derivatized with maleimide groups, or vinylsulfone groups, or with chemically activated thiol groups can be conjugated to a thiol group in C4-tag. On the other hand, thiol group in the C4-tag can be modified with formation of an activated disulfide bond that might react with available thiol groups on various entities, or it can be modified with bifunctional reagents for conjugation to entities that can react with the second functional group.

Thus, it has now been discovered that a cysteine-containing peptide fusion C4-tag can confer upon a protein fused to the tag the ability to be chemically conjugated to various chemical components. The cysteine residue of the C4 tag is used to form a covalent bond to the chemical components, thus providing a strong, stable linkage. Through the cysteine residue of C4, stable bonds may be formed between the C4 tagged protein and a wide variety of entities, including drugs, drug carriers, contrast agents, carriers for contrast agents, radionuclides, carriers for radionuclides, various nano- and microparticles, including liposomes, quantum dots, small and ultra-small paramagnetic particles, other proteins or protein fragments, nucleic acids, various protein-modifying molecules, including but not limited to polyethyleneglycol of various molecular weights, as well as surfaces of various devices, such as biomedical devices, biosensors, or artificial tissue scaffolds. In one embodiment, a complimentary adapter protein is covalently bonded to the C4 tagged protein through a disulfide bond. The adapter protein can be used a platform for conjugation to various entities described above. The present invention discloses that C4-tagged proteins retain protein functional activity and can be site-specifically conjugated to various entities without loss of functional activity either in vitro or in vivo.

The formation of a covalent bond offers several advantages for the present invention. First, the entity covalently bound to C4-tag is removed from the functional parts of the protein. Furthermore, a complimentary adapter protein allows further distancing of bound entities from the functional parts of the protein. Second, the covalent bond is strong such that the materials bound to the C4 tagged protein do not easily dissociate in biological fluids or in solutions. Third, the chemistry and conditions to form the covalent bond known and can be easily reproduced. Fourth, under certain conditions known to those of skill in the art, it is possible to destroy the covalent linkage and permit the components to dissociate. For example, if a disulfide bond is formed, appropriate conditions can be selected to reduce this bond and permit the C4-tagged protein to dissociate. This feature of the invention offers advantages in that, for example, that derivatized surfaces can be regenerated after a predetermined length of time.

Unless defined otherwise, all technical and scientific terms used herein have the same meaning as is commonly understood by one of skill in art to which the subject matter herein belongs.

As used herein, "C4", refers to a mutant N-terminal 15 amino acid long fragment of human RNase I with the following nucleic acid and amino acid sequences:

```
                                        (SEQ ID NO: 1)
AAAGAATCTTGCGCTAAAAAATTTCAACGTCAACACATGGACTCT (SEQ ID NO: 2)
Lys-Glu-Ser-Cys-Ala-Lys-Lys-Phe-Gln-Arg-Gln-His-
Met-Asp-Ser
```

Although minimally altered human peptides are not expected to be immunogenic in humans and therefore are preferred embodiments of cysteine-containing tags, it is understood that in some applications immunogenicity is not an issue, and therefore these peptides may be used as modified by amino acid substitutions, amino acid deletions, amino acid insertions, and amino acid additions, including placing of cysteine residue in different positions in these peptides or using corresponding fragments from non-human ribonucleases.

As used herein, "targeting protein" refers to a protein that can selectively interact with cellular receptors or other cell surface proteins, or can selectively interact with certain components of the environment, either free or bound to a surface.

As used herein, the term "linker sequence" refers to an innocuous length of nucleic acid or protein that joins two other sections of nucleic acid or protein.

The terms "mutant" and "mutated" refer to nucleic acid or protein sequences which are not found in nature. The term "truncated" refers to nucleic acid or protein sequences that are shorter than those found in nature.

As defined herein, "biological conjugate" refers to a complex between a targeting moiety and a binding moiety and stabilized by a covalent bond. "Targeting moiety" refers to a protein having a polypeptide comprising C4 and a targeting protein. "Binding moiety" refers to any substance or surface that can be covalently bound to the targeting moiety. The term "functional group" refers to natural or non-natural chemical groups that interact chemically with a thiol group. A natural functional group refers to a chemical group that is found naturally in the binding moiety that can interact chemically with a thiol group. A non-natural functional group refers to a group that is artificially added to the binding moiety (e.g., addition of a maleimide group or vinylsulfone group to polyethylene glycol) such that the artificial group is chemically reactive with the thiol group of the binding moiety.

"Adapter protein" refers to a protein that is complimentary (e.g., part of a binding pair) and can interact with the targeting moiety to form a specific disulfide bond between it and the targeting moiety. "Fusion protein" refers to a recombinant protein that contains two or more polypeptide fragments that are encoded by DNA sequences that have been combined with the methods of recombinant DNA technology in a form that allows expression of the fusion protein in suitable hosts.

As used herein, "carrier" refers to natural or synthetic molecules or aggregates thereof which can be associated covalently or non-covalently with therapeutic, diagnostic, or research compounds. Such carriers include, but are not limited to chelators, natural or synthetic polymers including dendrimers, co-polymers, derivatized polymers, liposomes, various viral and bacteriophage particles, various natural and manufactured nano- and microparticles, and beads.

As used herein, "scVEGF" refers to a single chain vascular endothelial growth factor that comprises two 3 to 112 amino acid residue fragments of the $VEGF_{121}$ isoform connected head-to-tail into a single-chain protein via alanine residue and has the following protein and nucleic acid sequences:

```
                                          (SEQ ID NO: 4)
NH2-Met Ala Glu Gly Gly Gly Gln Asn His His Glu

Val Val Lys Phe Met Asp Val Tyr Gln Arg Ser Tyr

Cys His Pro Ile Glu Thr Leu Val Asp Ile Phe Gln

Glu Tyr Pro Asp Glu Ile Glu Tyr Ile Phe Lys Pro

Ser Cys Val Pro Leu Met Arg Cys Gly Gly Cys Cys

Asn Asp Glu Gly Leu Glu Cys Val Pro Thr Glu Glu

Ser Asn Ile Thr Met Gln Ile Met Arg Ile Lys Pro

His Gln Gly Gln His Ile Gly Glu Met Ser Phe Leu

Gln His Asn Lys Cys Glu Cys Arg Pro Lys Lys Asp

Arg Ala Arg Ala Met Ala Glu Gly Gly Gly Gln Asn

His His Glu Val Val Lys Phe Met Asp Val Tyr Gln

Arg Ser Tyr Cys His Pro Ile Glu Thr Leu Val Asp

Ile Phe Gln Glu Tyr Pro Asp Glu Ile Glu Tyr Ile

Phe Lys Pro Ser Cys Val Pro Leu Met Arg Cys Gly

Gly Cys Cys Asn Asp Glu Gly Leu Glu Cys Val Pro

Thr Glu Glu Ser Asn Ile Thr Met Gln Ile Met Arg

Ile Lys Pro His Gln Gly Gln His Ile Gly Glu Met

Ser Phe Leu Gln His Asn Lys Cys Glu Cys Arg Pro

Lys Lys Asp Arg Ala Arg-COOH (SEQ ID NO: 3)
ATGGCAGAAGGAGGAGGGCAGAATCATCACGAAGTGGTGAAGTTCATGGA

TGTCTATCAGCGCAGCTACTGCCATCCAATCGAGACCCTGGTGGACATCT

TCCAGGAGTACCCTGATGAGATCGAGTACATCTFFCAAGCCATCCTGTGT

GCCCCTGATGCGATGCGGGGCTGCTGCAATGACGAGGGCCTGGAGTGTG

TGCCCACTGAGGAGTCCAACATCACCATGCAGATTATGCGGATCAAACCT

CACCAAGGCCAGCACATAGGAGAGATGAGCTTCCTACAGCACAACAAATG

TGAATGCAGACCAAAGAAAGATAGAGCAAGAGCCATGGCAGAAGGAGGAG

GGCAGAATCATCACGAAGTGGTGAAGTTCATGGATGTCTATCAGCGCAGC

TACTGCCATCCAATCGAGACCCTGGTGGACATCTTCCAGGAGTACCCTGA

TGAGATCGAGTACATCTTCAAGCCATCCTGTGTGCCCCTGATGCGATGCG

GGGGCTGCTGCAATGACGAGGGCCTGGAGTGTGTGCCCACTGAGGAGTCC

AACATCACCATGCAGATTATGCGGATCAAACCTCACCAAGGCCAGCACAT

AGGAGAGATGAGCTTCCTACAGCACAACAAATGTGAATGCAGACCAAAGA

AAGATAGAGCAAGA TGA
```

Due to the redundancy of the genetic code, however, any nucleic acids that code for SEQ ID NO:4 is embraced by the nucleic acids of the present invention.

In yet another embodiment, the targeting moiety has the polypeptide sequence shown in SEQ ID NO:14. This polypeptide sequence, which is a genetic fusion of C4 and a single chain VEGF (scVEGF) having the polypeptide sequence shown in SEQ ID NO:4, is encoded by the nucleic acid sequence shown in SEQ ID NO:13. Due to the redundancy of the genetic code, however, any nucleic acids that code for SEQ ID NO:14 is embraced by the nucleic acids of the present invention. Although scVEGF contains 16 cysteine residues per single-chain molecule, C4-tagged molecules are refolded into functionally active conformation, whereby the cysteine residue in C4-tag can be conjugated to various entities yielding conjugates with functional activities comparable to that of unmodified VEGF.

As indicated above, in one embodiment, the present invention is directed to a biological conjugate, comprising: (a) a targeting moiety comprising a polypeptide having an amino acid sequence comprising the polypeptide sequence of SEQ ID NO:2 and the polypeptide sequence of a selected targeting protein; and (b) a binding moiety; wherein the biological conjugate has a covalent bond between the thiol group of SEQ ID NO:2 and a functional group in the binding moiety. The present invention is also directed to a biological conjugate, comprising: (a) a targeting moiety comprising a polypeptide having an amino acid sequence comprising the polypeptide sequence of SEQ ID NO:2 and the polypeptide sequence of a selected targeting protein; and (b) a binding moiety that comprises an adapter protein bound covalently to the targeting moiety, the adapter protein having a thiol group; wherein the biological conjugate has a disulfide bond between the thiol group of SEQ ID NO:2 and the thiol group of the adapter protein. Each of these components are discussed in more detail below.

The targeting moiety is preferably a protein having a polypeptide comprising the C4 peptide and a targeting protein. As indicated above, the C4 peptide portion of the targeting moiety is a mutant N-terminal 15 amino acid long fragment of human RNase I wherein arginine at position 4 has been substituted with cysteine. This particular peptide offers several advantages in the present invention. The human origin decreases the likelihood of inducing a strong immune response in a human host. Furthermore, an N-terminal fragment of human RNase I is capable of forming an α-helix that may protect it from forming disulfide bonds with other cysteine residues in the fusion protein during refolding and purification of the protein. Finally, enzymatically inactive wild type N-terminal and C-terminal fragments of human RNase I spontaneously form enzymatically active non-covalent complexes, a phenomenon that is exploited in the present invention for developing of complimentary adapter proteins, capable of forming disulfide bond with C4 residue in C4-tag. The mutant N-terminal 15 amino acid long fragment of human RNase I has the following nucleic acid and amino acid sequences:

```
                                       (SEQ ID NO: 1)
AAAGAATCTTGCGCTAAAAAATTTCAACGTCAACACATGGACTCT (SEQ ID NO: 2)
Lys-Glu-Ser-Cys-Ala-Lys-Lys-Phe-Gln-Arg-Gln-His-

Met-Asp-Ser
```

The targeting protein portion of the targeting moiety is any protein that can selectively bind to cellular receptors or other cell surface proteins or selectively interact with certain components of the environment, and is genetically fused to the C4 peptide. In preferred embodiments, the targeting protein may be human vascular endothelial growth factor (VEGF), or a mutated or truncated form thereof such as $VEGF_{110}$, human annexin V, or a mutated or truncated form thereof, a catalytically inactive fragment of anthrax lethal vector, or a mutated or truncated form thereof, or a single chain VEGF derivative, or a mutated or truncated form thereof.

In one embodiment, the targeting moiety has the polypeptide sequences shown in SEQ ID NOS: 6 or 8. These polypeptide sequences, which are genetic fusions of C4 and $VEGF_{121}$ or $VEGF_{110}$, respectively, are coded by the nucleic acid sequences shown in SEQ ID NOS:5 and 7, respectively. Due to the redundancy of the genetic code, however, any nucleic acids that code for SEQ ID NOS:6 or 8 are embraced by the nucleic acids of the present invention. In addition, although selected isoforms of VEGF ($VEGF_{121}$) contains 18 cysteine residues per dimeric molecule, tagged molecules are refolded into functionally active conformation, whereby cysteine residue in C4-tag can be conjugated to various entities yielding conjugates with functional activities comparable to that of unmodified VEGF.

Vascular endothelial growth factor (VEGF) controls growth of endothelial cells via interaction with several receptors, among which KDR/flk-1 (VEGFR-2) receptor expression is limited mostly to endothelial cells. In adult organisms the growth of endothelial cells (angiogenesis) occurs, with the exception of corpus luteum development, only in various pathological conditions. Thus, KDR/flk-1 (VEGFR-2) receptor-mediated delivery of therapeutic, diagnostic, contrast, and research entities site-specifically linked to VEGF or scVEGF, or linked to VEGF or scVEGF via a complimentary adapter protein, may be useful in therapies for various pathologies. On the other hand, long-circulating, or slow-releasable from a suitable matrix, site-specifically PEGylated VEGF or scVEGF, as well as VEGF or scVEGF conjugated to the surfaces of biomedical devices, such as stents, or tissue scaffolds, might be useful for promotion of angiogenesis in ischemic situations.

In another embodiment, the targeting moiety has the polypeptide sequence shown in SEQ ID NO:10. This polypeptide sequence, which is a genetic fusion of C4 and annexin V, is encoded by the nucleic acid sequence shown in SEQ ID NO:9. Due to the redundancy of the genetic code, however, any nucleic acids that code for SEQ ID NO:10 is embraced by the nucleic acids of the present invention. Although annexin V contains a single cysteine residue, tagged molecules are refolded into functionally active conformation, whereby the cysteine residue in C4-tag can be conjugated to various entities yielding conjugates with functional activities comparable to that of unmodified annexin V. Annexin V interacts with phosphatidylserine exposed on the surface of apoptotic cells, and is used as an early marker of apoptotic process. Thus, phosphatidylserine-mediated delivery of therapeutic, diagnostic, or research entities site-specifically linked to annexin V might be useful for inhibition or promotion of apoptosis.

In another embodiment, the targeting moiety has the polypeptide sequence shown in SEQ ID NO:12. This polypeptide sequence, which is a genetic fusion of C4 and a catalytically inactive fragment of anthrax lethal factor, known as LFn, is encoded by the nucleic acid sequence shown in SEQ ID NO:11. Due to the redundancy of the genetic code, however, any nucleic acids that code for SEQ ID NO:12 is embraced by the nucleic acids of the present invention. Although LFn contains no cysteine residues, tagged molecules are refolded into functionally active conformation, whereby the cysteine residue in C4-tag can be conjugated to various entities yielding conjugates with functional activities comparable to that of unmodified LFn. Catalytically inactive fragment of anthrax lethal factor, LFn, pairs with another anthrax protein, named protective antigen (PA) that interacts with the same cellular receptors as the combination of catalytically active lethal factor/protective antigen (LF/PA). Thus, PA-mediated delivery of therapeutic, diagnostic, or research entities site-specifically linked to LFn might be useful for mapping sites with receptors for PA, or delivery to cells compounds that might interfere with cytotoxic activity of lethal factor.

In yet another embodiment, the targeting moiety has the polypeptide sequence shown in SEQ ID NO:14. This polypeptide sequence, which is a genetic fusion of C4 and a single chain VEGF (scVEGF) having the polypeptide sequence shown in SEQ ID NO:4, is encoded by the nucleic acid sequence shown in SEQ ID NO:13. Due to the redundancy of the genetic code, however, any nucleic acids that code for SEQ ID NO:14 is embraced by the nucleic acids of the present invention. As indicated above, scVEGF comprises two 3 to 112 amino acid residue fragments of the $VEGF_{121}$ isoform connected head-to-tail into a single-chain protein via alanine residue. Although scVEGF contains 16 cysteine residues per single-chain molecule, tagged molecules are refolded into functionally active conformation, whereby the cysteine residue in C4-tag can be conjugated to various entities yielding conjugates with functional activities comparable to that of unmodified dimeric VEGF.

With reference to the above targeting moiety, a linker sequence may be positioned between the C4 peptide and the sequence of the targeting protein. Linker sequences, such as $Gly_4Ser$ or $(Gly_4Ser)_3$ linkers, are engineered in the commercially available vectors for bacterial expression of recombinant proteins and can be readily engineered into vectors for expression of recombinant proteins in other hosts, including, but not limited to mammalian cells, insect cells, yeast cells, and transgenic organisms. Linkers serve to provide some useful distance between the C4 peptide and the targeting protein. Although in the presented embodiments C4-tag is positioned at the N-terminus of targeting protein, one skilled in the art would appreciate that the tag may be placed at the C-terminus of the targeting protein, or inside the functionally dispensable area of targeting protein, for example between two functional domains of single-chain antibody, using commonly known methods of genetic engineering.

Figure 1B:
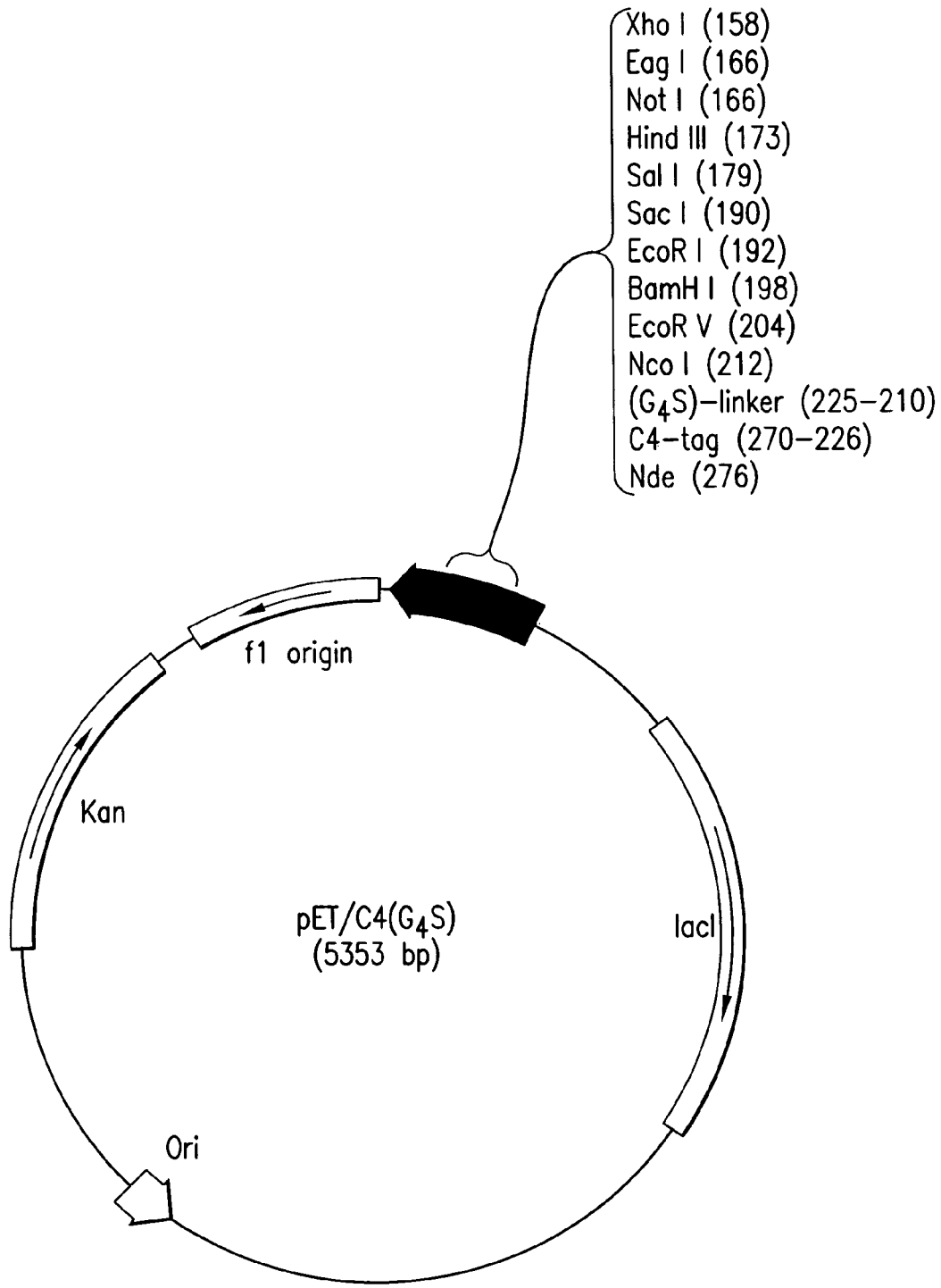

FIG. 1, Panel A, shows amino acid and nucleic acid sequences of C4-tag genetically fused to a multiple cloning site region found in the typical expression plasmid via a $G_4S$ linker. As shown in Panel A of FIG. 1, the full nucleic acid sequence includes control and transcription elements (T7 promotor, lac operatior, ribosome binding site, and the like) as well as the nucleic acid sequence of the C4 tag. A linker sequence separates the C4 sequence from a multiple cloning site, which may be used to introduce nucleic acids of interest that will function as the targeting protein. A T7 termination site completes the full length nucleic acid. FIG. 1, Panel B, shows a schematic representation of a plasmid for bacterial expression of fusion recombinant proteins fused to C4-tag via a G4S linker.

The targeting moiety of biological conjugate may be cytokines, chemokines, growth factors, antibodies and their fragments, enzymes, and combinations of thereof that may be useful in various biomedical or industrial applications. The binding moiety portion of the biological conjugate may be any substance or surface that can be covalently bound to the C4-thiol group of targeting moiety or to functional group of adapter protein in the adapter/targeting moiety conjugate.

Examples of useful binding moieties include, but are not limited to, drugs, radionuclide chelators, polyethylene glycol, dyes, lipids, liposomes, and selected surfaces.

Useful radionuclide chelators include compounds such as 5-maleimido-2-hydraziniumpyridine hydrochloride (HYNIC) for loading with imaging or therapeutic radionuclide. Polyethylene glycol is useful for slowing blood clearance of protein, and may be used in a derivatized (e.g., modified with maleimide or vinylsulfone) or underivatized forms. Useful dyes include, for example, cyanine dye Cy5.5 for near-infrared fluorescent imaging. Surfaces that may bind to the C4-thiol group of targeting moiety or to functional group of adapter protein in the adapter/targeting moiety conjugate include surfaces of a nano- or microparticle, the surface of a dendrimer, surfaces of tissue culture scaffolds, biomedical devices, and biosensors. It is understood that when a binding entity include surface, it may be used as such, or may have other chemical groups deposited on the surface by methods known in art. These chemical groups might be further used for modification with bifunctional reagents that allow conjugation to C4-tag or to adapter protein via methods known in art.

In one embodiment of the present invention, the biological conjugate has a covalent bond between the thiol group of the C4 peptide (SEQ ID NO:2), and a naturally occurring functional group in the binding moiety. Thus, it is contemplated that the thiol group of the C4 peptide reacts chemically directly with a reactive group in the binding moiety such that a stable covalent bond is formed. In alternative embodiments, the reactive group that reacts with the thiol group of the C4 peptide may be introduced artificially, for example by using bifunctional crosslinking agents known in art. For example, a maleimide group can be introduced into polyethylene glycol or a lipid and used for reaction with the thiol group of the C4 peptide.

In an alternative embodiment, the biological conjugate of the present invention includes a binding moiety that comprises adapter protein bound covalently to the targeting moiety. In general, the adapter protein is a mutant human RNase I, or a fragment thereof, that includes cysteine at position 118 ($Cys_{118}$). Examples of adapter proteins useful in the present invention include proteins having polypeptide sequences shown in SEQ ID NO:16, SEQ ID NO:18, SEQ ID NO:20, and SEQ ID NO:22, which are described in more detail below.

Four particularly preferred embodiments of adapter protein capable of forming a disulfide bond with C4 residue in C4-tag are shown in FIG. 2 where Panel A provides a schematic representation of site-specific conjugation between C4-tagged fusion recombinant protein and a complimentary adapter protein. FIG. 2, Panel B shows a schematic representation of a family of adapter proteins based on T24N, V118C mutant human RNase I. The first embodiment is a fragment of T24N, V118C mutant human RNase I, named HuS(C118) (SEQ ID NOS:15 and 16). Amino groups of HuS(C118) can be used for conjugation to various entities using methods known in art prior to site-specific conjugation of HuS(C118) to C4-tagged proteins. The second embodiment is a fragment of T24N, V118C mutant human RNase I containing the N88C substitution, named HuS(C88,C118) (SEQ ID NOS:17 and 18). C88 thiol group in HuS(C88,C118) can be used for conjugation to various entities using methods known in art after site-specific conjugation of HuS(C88,C118) to C4-tagged proteins. The third and fourth embodiments are based on a chimeric BH-RNase that contains a 1-29-aa fragment of bovine RNase A that differs from a corresponding fragment of human Rnase I in several positions and a 30-127 aa fragment of human RNase I (Gaynutdinov et al., 2003).

The third embodiment is the V18C mutant of BH-RNase containing the F8A and Q11P, substitutions, named BHR(A8, P11,C118) (SEQ ID NOS:19 and 20) which does not require removal of 20 N-terminal amino acid residues prior to site-specific conjugation to C4-tagged proteins. Amino groups of BHR(A8,P11,C118) can be derivatized with various entities using methods known in art prior to site-specific conjugation of HuR(A8,P11,C118) to C4-tagged proteins. The fourth embodiment is the V118C mutant BH-RNase containing A8,P11, and C88, named BHR(A8,P11,C88,C118) (SEQ ID NOS:21 and 22) which does not require removal of 20 N-terminal amino acid residues prior to site-specific conjugation to C4-tagged proteins. The C88 thiol group in BHR(A8,P11, C88,C118) can be used for conjugation with various entities using methods known in art after site-specific conjugation of BHR(A8,P11,C88,C118) to C4-tagged proteins. Using methods known in art it will be easy to construct other adapter proteins based on human RNase I capable of site-specific conjugation to C4-tagged proteins and providing convenient platforms for derivatization with various entities. One of skill in the art would appreciate that other adapter proteins based on human RNase I may be used in addition to those explicitly described herein. For example, one of skill in the art would appreciate that adapter proteins based on other ribonucleases, for example bovine RNase A, may be constructed as long as these adapter proteins retain the ability to form conjugates with C4-tag, or similar tags based on N-terminal fragments of other ribonucleases.

Panel C in FIG. 2 provides evidence of C4-VEGF and HUS(C118) conjugation via a disulfide bond leading to the appearance of DTT-sensitive new protein bands in samples named HuS-C4-VEGF on the SDS-PAGE gel corresponding to conjugation of one or two adapter HuS(C118) to C4-tags in a dimeric molecule of C4-VEGF. Panel D provides evidence that ribonuclease activity is reconstituted upon chemical conjugate formation, but not upon physical mixing of HuS(C118) adapter protein with C4-tagged recombinant fusion protein (Panel D).

The adapter protein may be derivatized with a host of functional materials to achieve a desired result. For example, in one embodiment, the adapter protein may be derivatized with a dye, such as Cy5.5 dye for optical imaging, or with a lipid for associating the adapter protein with a liposome that acts as a carrier for therapeutic, diagnostic, or research compounds. In one embodiment, the liposomes may carry or be loaded with doxorubicin ("DOXIL").

The biological conjugates may be combined with pharmaceutically acceptable carriers to produce pharmaceutical compositions for selectively delivering therapeutic, research, or diagnostic compounds to a target in a patient. Such a pharmaceutical composition may be administered to a patient, and the biological conjugate is permitted to contact the target to deliver the compound to the target in the patient. In these embodiments, useful pharmaceutically acceptable carriers include materials such as water, gelatin, lactose, starch, magnesium stearate, talc, plant oils, gums, alcohol, Vaseline, or the like. The pharmaceutical preparation of the invention should include an amount of the biological conjugate effective for the desired activity. The effective dosage will depend on the activity of the particular biological conjugate employed and is thus within the ordinary skill of the art to determine for any particular host mammal or other host organism.

In general, a pharmaceutically effective amount of the biological conjugate is combined in a conventional fashion with the pharmaceutically acceptable carrier to produce the pharmaceutical composition. The pharmaceutical composition of the invention is preferably administered internally, e.g., intravenously, in the form of conventional pharmaceutical preparations, for example in conventional enteral or parenteral pharmaceutically acceptable excipients containing organic and/or inorganic inert carriers as described above. The pharmaceutical preparations can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

EXAMPLES

The following Examples are intended to illustrate, but in no way limit the scope of the present invention. All parts and percentages are by weight and all temperatures are in degrees Celsius unless explicitly stated otherwise.

Example 1

Construction and Use of Expression Vectors Containing C4- and a Linker Peptide 1. Bacterial Strains and Plasmids

*E. coli* strain DH5α-T1 is commercially available from Invitrogen (USA). *E. coli* strains B121(DE3) and NovaBlue are commercially available from Novagen (USA). The pET29a(+) bacterial expression vector was obtained from Novagen (USA). The pLen-121 plasmid containing the DNA sequence encoding the 121-amino acid residue isoform of human VEGF has been described in U.S. Pat. No. 5,219,739, herein incorporated by reference in its entirety, and was obtained from Dr. J. Abraham (Scios Nova, Inc., USA). The pPAP1-1.6 plasmid containing the DNA sequence encoding human annexin V was obtained from Dr. J. Tait (University of Washington School of Medicine, Seattle, Wash.). The pGEX-KG LF254 plasmid containing the DNA sequence encoding non-toxic N-terminal fragment of anthrax lethal factor (LFn) was obtained from Dr. S. Leppla (National Institute of Allergy and Infectious Diseases, NIH, Bethesda, Md.).

2. DNA Manipulations

The restriction and modification enzymes employed herein are commercially available in the U.S. and were used according to the manufacturer's instructions. Preparation of competent cells, transformation, and bacterial medium were according to Sambrook et al. (J. Sambrook, E. F. Fritsch and T. Maniatis. (1989) Molecular Cloning: A Laboratory Manual, Cold Spring Harbor Laboratory Press, Cold Spring Harbor, N.Y.) or according to the manufacturer's instructions. Purification of plasmids was done using Wizard Plus SV Minipreps or Maxipreps DNA Purification Systems (Promega, USA) according to the manufacturer's instructions. The purification of DNA fragments from agarose gels was done using the Geneclean Spin kit (Bio 101, USA) according to the manufacturer's instructions.

3. Construction of Vectors for Expression of Proteins Fused to C4-tag.

The pET/Hu$(G_4S)_3$ vector for expression of recombinant proteins with an N-terminal Hu-tag fused to protein ORF via a $(G_4S)_3$ linker was constructed as described (Backer et al., 2004). The R4c amino acid substitution was introduced in Hu-tag of the pET/Hu$(G_4S)_3$ vector by site-directed mutagenesis using Gene-Tailor Site Directed mutagenesis kit (Invitrogen). Primers (SEQ ID NO:23 and SEQ ID NO:24) were used for introducing the R4c mutation. The resulted vector was confirmed by sequencing and designated pET/Hu-C4 $(G_4S)_3$.

SEQ ID NO: 23
5'-ATATACATATGAAAGAATCTTGCGCTAAAAAATTTC

SEQ ID NO: 24
5'-AGATTCTTTCATATGTATATCTCCTTCTTAAAGTT

DNA encoding C4-$G_4$S was amplified by PCR using pET/Hu-C4($G_4$S)$_3$ vector DNA as a template, a sense primer SEQ ID NO:25 introducing XbaI site, and antisense primer SEQ ID NO:26 introducing NcoI site. The insert was cloned into the pET29a(+) vector cut with XbaI and NcoI. The resulting vector was confirmed by sequencing and designated pET/Hu-C4-$G_4$S.

SEQ ID NO: 25
5'-GGATAACAATTCCCCTCTAGAAATAATTTTGTTTAAC

SEQ ID NO: 26
5'-ACTACCCATGGAACCGCCGCCACCAGAGTCCATG

4. Sub-Cloning of cDNA Fragments Encoding Proteins of Interest into the pET/Hu-C4($G_4$S)$_3$ and pET/Hu-C4-$G_4$S Vectors.

The pET/Hu-C4($G_4$S)$_3$ and pET/Hu-C4-$G_4$S vector DNAs were cut separately with NcoI and dephosphorylated. All DNA fragments to be cloned in the above vectors were amplified by PCR using primers introducing NcoI sites to the both ends of the amplified DNA fragments. DNA encoding the 121-aa isoform of human VEGF was amplified from the pLen-121 plasmid DNA using primers (SEQ ID NO:27 and SEQ ID NO:28). DNA encoding a 1-254-aa long N-terminal fragment of anthrax lethal factor (LFn) was amplified from the pGEX-KG LF254 plasmid DNA using primers (SEQ ID NO:29 and SEQ ID NO:30). DNA encoding human annexin V was amplified from the pPAP1-1.6 plasmid using primers (SEQ ID NO:31 and SEQ ID NO:32). Each amplified DNA fragment was cut with NcoI, purified, and cloned into NcoI sites of the vectors pET/Hu-C4$(G_4S)_3$ and pET/Hu-C4-$G_4S$. Clones with correct orientations of cloned ORF were selected by PCR using a T7-promoter based sense primer, and confirmed by sequencing.

SEQ ID NO: 27
5'-CACAAGCCATGGCACCCATGGCAGAAGGAGGA

SEQ ID NO: 28
5'-ACTACCCATGGTCACCGCCTCGGCTTGTCAC

SEQ ID NO: 29
5'-CTGCTCCATGGGAGCGGGCGGTCATGGTGATG

SEQ ID NO: 30
5'-ACTACCCATGGCTATAGATTTATTTCTTGTTCGTTAAATTTATC

SEQ ID NO: 31
5'-CACAAGCCATGGCACAGGTTCTCAGAG

SEQ ID NO: 32
5'-ACTACCCATGGTTAGTCATCTTCTCCACAGAGC

5. Expression and Purification of Recombinant Fusion Proteins with C4-tag.

All proteins were expressed in BL21(DE3) *E. coli* grown in LB medium (Q-Biogen, Carlsbad, Calif.). The expression was induced by 1 mM IPTG at the optical density of 0.5-0.7 unit at 600 nm. After induction, cultures were grown for 2.5-3 hrs at 37° C. with shaking at 300 rpm; then harvested by centrifugation and ruptured using EmulsiFlex-C5 (Avestin, Ottawa, Canada).

C4-VEGF was expressed in insoluble form and purified as follows: inclusion bodies were solubilized in 8 M urea, 20 mM Tris-HCl pH 8.0, 150 mM NaCl, 80 mM $Na_2SO_3$, 10 mM $Na_2S_4O_6$, 10 mM DTT, incubated for 6-8 hrs at 4° C. with agitation; then supplemented with 2.5 mM Tris[2-carboxyethyl]phosphine (Pierce), and incubated for 16-18 hrs at 4° C. Solubilized protein was refolded via a tree-step dialysis: first, 10-12 hrs at 4° C. in 10 volumes of 20 mM Tris-HCl pH 8.0, 2 M urea, 0.5 M arginine, 1 mM reduced glutathione, 0.4 mM oxidized glutathione; second, 24 hrs at 4° C. in 50 volumes of 20 mM Tris-HCl pH 8.0; and third, 24 hrs at 4° C. in 50 volumes of 20 mM NaOAc (pH 5.5). After dialysis, solution was clarified by centrifugation (15,000×g for 20 min), and C4-VEGF was purified by chromatography on Heparin HP Sepharose (1-ml pre-packed columns, Amersham). For conjugation, C4 thiol group in C4-VEGF was deprotected by mild DTT treatment using 1.2 molar excess DTT at 34° C. for 45 min.

To minimize potential involvement of cysteine residue present in position 116 in native VEGF121, the inventors prepared a version of C4-VEGF truncated at position 112 using methods known in art. Truncated protein contains 110 amino acids (a 3-112aa fragment of VEGF121), and therefore it was named C4-$VEGF_{110}$. The C4-$VEGF_{110}$ was expressed and purified as described above and displayed activities similar to that of C4-VEGF in tissue culture assays.

To further optimize C4-tagged VEGF the inventors constructed a single chain VEGF fused to a single C4 peptide tag via a $G_4S$ linker peptide (C4-scVEGF). In general, engineering, expression, refolding, and purification of monomeric proteins is simplier than oligomeric, or even dimeric, such as native isoforms of VEGF. In addition, scVEGF was designed to avoid formation of inactive monomers of VEGF that are usually present in preparations of dimeric VEGF, to simplify any protein re-engineering of VEGF, to simplify expression, refolding and purification and to simplify conjugation of binding moieties to a single C4-tag. First, the pET/Hu-C4-$G_4S$ vector DNA was cut with BamHI and dephosphorylated. DNA encoding a 3-112-aa long fragment of human VEGF was amplified from the pLen-121 plasmid using a sense primer (SEQ ID NO:33) introducing BamHI site immediately upstream of VEGF codon 3, and an antisense primer (SEQ ID NO:34) introducing a stop codon immediately downstream of codon 112 of VEGF and BamHI site immediately after the stop codon. The amplified DNA fragment was purified, cut with BamHI, and cloned into BamHI site of the pET/Hu-C4-G4S vector. Correct orientation of cloned ORF was selected by PCR using a T7-promoter based sense primer. Plasmid DNA purified from the selected clones was confirmed by sequencing and designated pET/C4(G4S)$VEGF_{110}$.

SEQ ID NO: 33
5'-CACGGATCCGGTGGCGGCGGTAGTGGT

SEQ ID NO: 34
5'-CACGGATCCTCATCTTGCTCTATCTTTCTTTGGTCTGC

The pET/C4(G4S)$VEGF_{110}$ vector DNA was cut with NcoI and dephosphorylated. DNA encoding a 3-112-aa fragment of human VEGF was amplified from the pLen-121 plasmid by PCR using a sense primer (SEQ ID NO:35) introducing NcoI site immediately upstream of VEGF codon 3, and antisense primer (SEQ ID NO:36) introducing a cytosine immediately downstream of VEGF codon 112 (for compensation of ORF shift) and NcoI site immediately after the introduced cytosine. The amplified DNA fragment was purified, cut with NcoI, and cloned into NcoI site of the pET/C4 (G4S)VEGF$_{110}$ vector. Clones with two VEGF$_{110}$ copies were selected by PCR using a T7-promoter based sense primer and a T7-terminator based antisense primer. DNA isolated from four random selected clones was sequenced, and a clone containing a VEGF$_{110}$ tandem with a head-to-tail VEGF$_{110}$ orientation was selected for propagation. The selected plasmid designated pET/C4(G$_4$S)scVEGF was transformed into competent E. coli cells strain BL21 (DE3) for protein expression.

```
                                          SEQ ID NO: 35
         5'-CACAAGCCATGGCACCCATGGCAGAAGGAGGA

SEQ ID NO: 36
         5'-ACTACCCATGGCTCTTGCTCTATCTTTCTTTGGTCTGC
```

The C4-scVEGF was expressed and purified as described above and displayed activities similar to that of C4-VEGF in tissue culture assays. C4-scVEGF was recovered with ~50% of C4 thiol group available for conjugation. For conjugation, C4 thiol group in C4-VEGF was deprotected by mild DTT treatment with 0.5 molar equivalent of DTT.

C4-LFn was expressed in a soluble cytoplasmic form and purified as follows: soluble part of bacterial lysate was dialyzed against 200 volumes of 20 mM Tris-HCl pH 8.0 for 20 hrs at 4° C., clarified by centrifugation (15,000 g for 20 min); and passed through Sepharose Q FF column. C4-LFn containing fractions were pooled together, dialyzed against 100 volumes of 20 mM NaOAc pH 6.5 for 20 hrs at 4° C., and purified on Heparin HP Sepharose followed by hydrophobic interaction chromatography on Butyl FF Sepharose (1-ml pre-packed columns, Amersham). The yield of C4-LFn was 8-10 mg/L, purity >98% by SDS-PAGE followed by SimplyBlue Safe Stain (Invitrogen).

C4-annexin was purified as described for Hu-annexin (Backer et al., 2004). Depending on the nature of a linker, and a protein, a cysteine residue in C4-tag is involved to a various degree in mixed disulfide with red-ox components of the refolding buffer. When necessary, cysteine residues can be deprotected with DTT under conditions that are optimized for every C4-protein.

6. Construction and Expression of Adapter Proteins.

6.1. Chimeric 1-29B/30-127H-RNase (BH-RNase) comprising of a 1-29 aa fragment of bovine RNase A and a 30-127 aa fragment of human RNase I has been constructed, expressed and purified as described (Gaynutdinov et al., 2003). The V118C mutation was introduced in the pET29/1-29B/30-127H-RNase plasmid DNA by site-directed mutagenesis using Gene-Tailor Site Directed mutagenesis kit (Invitrogen) and primers (SEQ ID NO:37 and SEQ ID NO:38). The VC118 substitution was confirmed by sequencing, the protein was designated BH-RNase(C118). BH-RNase(C118) was expressed and purified as described for wild type BH-RNase (Gaynutdinov et al, 2003). The presence of a reactive thiol group was tested by reaction with a thiol reagent N-(1-pyrene)-maleimide (Molecular Probes, Eugene, Oreg.) followed by RP HPLC analysis as described (Backer et al., 2002). HuS(C118) adapter protein was obtained by limited digestion of BH-RNase(C118) with subtilisin (Sigma) as described for BH-RNase (Gaynutdinov et al., 2003).

```
                                          SEQ ID NO: 37
         5'-AAGGCTCTCCGTACGTTCCGTGTCATTTCGACGCG

SEQ ID NO: 38
         5'-CGGAACGTACGGAGAGCCTTCGCATGCAAC
```

6.2. HuS(C88,C118)

The N88C mutation was introduced in the pET29/1-29B/30-127H-RNase(V118C) plasmid DNA by site-directed mutagenesis using primers (SEQ ID NO:39 and SEQ ID NO:40). The N88C substitution was confirmed by sequencing, and the protein was designated BH-RNase(C88,C118). BH-RNase(C88,C118) was expressed, purified and digested by subtilisin to yield HuS(C88,C118) adapter protein as described above for BH-RNase(C118).

SEQ ID NO: 39 5'-TCACTGACTGCCGTCTTACTTGCGGATCCCGTT

SEQ ID NO: 40 8 5'-AGTAAGACGGCAGTCAGTGATATGCATAGAA 6.3 HuR(A8,P11,C118)

The Q11P and F8A mutations were introduced consequently in the pET29/1-29B/30-127H-RNase(V118C) plasmid DNA by site-directed mutagenesis using primers SEQ ID NO:41-44, respectively. Both substitutions were confirmed by sequencing, and the protein was designated BH-RNase (A8,P1,C118). BH-RNase(A8,P11, C118) was expressed and purified as described above for BH-RNase(C118).

SEQ ID NO: 41 5'-GCAGCCAAGTTTGAGCGGCCGCACATGGACTC

SEQ ID NO: 42 5'-GCCGCTCAAACTTGGCTGCTGCAGTTTCCTT

SEQ ID NO: 43 5'-GGAAACTGCAGCAGCCAAGGCTGAGCGGCCGC

SEQ ID NO: 44 5'-CTTGGCTGCTGCAGTTTCCTTCATATGTATAT

7. Construction and Expression of Proteins Used in the Assays.

7.1. SLT-VEGF.

The pET/VEGF121-SLT/L plasmid encoding SLT-VEGF fusion protein carrying N-terminal S-tag and His-tag was described previously (Backer & Backer, 2001). The SLT-VEGF DNA coding sequence was amplified by PCR from the pET/VEGF121-SLT/L plasmid DNA using primers (SEQ ID NO:45) introducing NdeI site and (SEQ ID NO:46) introducing Xho I site. Purified PCR product was cut with Nde I and Xho I restrictases, purified, and cloned into Nde I-Xho I sites of the pET29a(+) vector (Novagen). The resulting plasmid was confirmed by sequencing and designated pET29/SLT-VEGF. SLT-VEGF was expressed in BL21(DE3) as described above for C4-carrying proteins, and purified as follows: inclusion bodies were solubilized in 8 M urea, 20 mM Tris-HCl pH 8.0, 150 mM NaCl, 80 mM Na$_2$SO$_3$, 10 mM Na$_2$S$_4$O$_6$, 10 mM DTT and incubated for 6-8 hrs at 4° C. with agitation; then supplemented with 5 mM Tris[2-carboxyethil]phosphine (Pierce) and incubated for 16-18 hrs at 4° C. Solubilized protein was refolded via a tree-step dialysis: first, for 8-10 hrs at 4° C. in 10 volumes of 20 mM Tris-HCl pH 8.0, 2 M urea, 0.5 M arginine, 1 mM reduced glutathione, 0.4 mM oxidized glutathione; second, 24 hrs at 4° C. in 100 volumes of 20 mM Tris-HCl pH 8.0, 150 mM NaCl, 0.01% NP-40; and third, 24 hrs at 4° C. in 100 volumes of 20 mM Tris-HCl pH 8.0, 20 mM NaCl. After dialysis, solution was clarified by centrifugation (15,000×g for 20 min), and SLT- VEGF was purified by chromatography on HiTrap Q Sepharose (1-ml pre-packed columns, Amersham).

SEQ ID NO: 45
5'-AAAAACATATGAAGGAATTTACCTTAGACTTCTCG

SEQ ID NO: 46
5'-TACTCGAGTCACCGCCTCGGCTTGTCAC 7.2. Hu-VEGF.

Hu-VEGF 121 fusion protein carrying N-terminal wild type Hu-tag was constructed as described in Backer et al., 2003. Hu-VEGF121 was expressed and refolded from inclusion bodies as described above for C4-VEGF with the following modifications: refolding from inclusion bodies was done via a two-step dialysis: first, for 8-10 hrs at 4° C. in 10 volumes of 20 mM Tris-HCl pH 8.0, 2 M urea, 0.5 M arginine, 1 mM reduced glutathione, 0.4 mM oxidized glutathione; second, 24 hrs at 4° C. in 50 volumes of 20 mM Tris-HCl pH 8.0. Also, for final Hu-VEGF121 purification, HiTrap SP Sepharose FF followed by Heparin HP Sepharose chromatography (1-ml pre-packed columns, Amersham) was performed.

8. Functional Activities of Recombinant Fusion Proteins with C4-tag.

A. VEGF activity. Functional activities of VEGF and VEGF-based conjugates were tested in two assays. First assay, stimulation of VEGFR-2 autophosphorylation was performed as follows: near-confluent 293/KDR cells after overnight starvation (DMEM/0.5% FBS) were shifted to serum-free DMEM with 0.5 mM sodium vanadate for 20 min at 37° C., then stimulated with VEGF for 10 min at 37° C., lysed and analyzed by Western blotting using anti-phosphotyrosine RC20:HRPO conjugate (BD Transduction Labs, USA). Second assay, protection of 293/KDR cells from cytotoxic effect of SLT-VEGF, was performed as follows. 293/KDR cells were plated on 96-well plates 20 hrs before the experiment, 1000 cells/well. Varying amounts of VEGF or VEGF-based conjugates were mixed with SLT-VEGF in complete culture medium, and added to cells in triplicate wells to a final SLT-VEGF concentration of 1 nM. Viable cells were quantitated 96 hrs later by CellTiter 96® AQueous One Solution Cell Proliferation Assay kit (Promega, USA).

B. Annexin V activity. Functional activities of C4-annexin and HuS-C4-annexin were tested by their ability to compete with FITC-annexin (Sigma) for binding to phosphatidylserine-displaying erythrocytes of stabilized human blood (4C Plus Cell Control, Beckman Coulter, USA) as described (Tait et al., 1995). Briefly, ten million erythrocytes were incubated with varying amounts of annexin in the presence of 5 nM FITC-annexin V (Sigma, St. Louis, Md.) in binding buffer (10 mM HEPES, pH 7.4, 136 mM NaCl, 2.5 mM CaCl2) for 15 min at RT. Cells were spun down, resuspended in a binding buffer supplemented with 5 mM EDTA, and spun down again. FITC-annexin fluorescence in the supernatants was measured at $\lambda_{ex}$ 485 nm/$\lambda_{em}$ 520 nm.

C. LFn activity. C4-LFn and Hus-C4-LFn were tested for their ability to protect RAW cells from cytotoxic effects of full-length LF in the presence of PA. RAW264.7 cells were plated on 96-well plates 15×10³ cells/well 20 hrs before the experiment. Varying amounts of LFn, C4-LFn, or Hus-C4-LFn were mixed with LF and PA (List Biological, USA) in DMEM complete culture medium, and added to cells in triplicate wells to final concentrations of 2 nM PA and 0.2 nM LF. After 2.5 hrs of incubation at 37° C. in 5% $CO_2$, viable cell numbers were determined by CellTiter 96® AQueous One Solution Cell Proliferation Assay kit (Promega).

9. Cell Lines.

HEK293 human transformed embryonic kidney cells (CRL-1573) and RAW 264.7 mouse monocytes (TIB-71) were from American Type Culture Collection (ATCC, Rockville, Md.). 293/KDR cells expressing 2.5×10⁶ VEGFR-2/cell have been developed in SibTech, Inc. (Newington, Conn.; Backer and Backer, 2001a). All cells were maintained in DMEM (Life Technologies, USA) supplemented with 10% fetal calf serum (Gemini, USA), 2 mM glutamine (Life Technologies, USA), and penicillin-streptomycin (Life Technologies, USA) at 37° C., 5% CO2.

Example 2

Site-Specific Conjugation of C4-Tagged Proteins to Adapter Protein HuS(C118)

The protocol included site-specific conjugation of C4-tagged proteins to adapter protein HuS(C118) and testing the functional activities of conjugates in tissue culture.

Figure 2A:
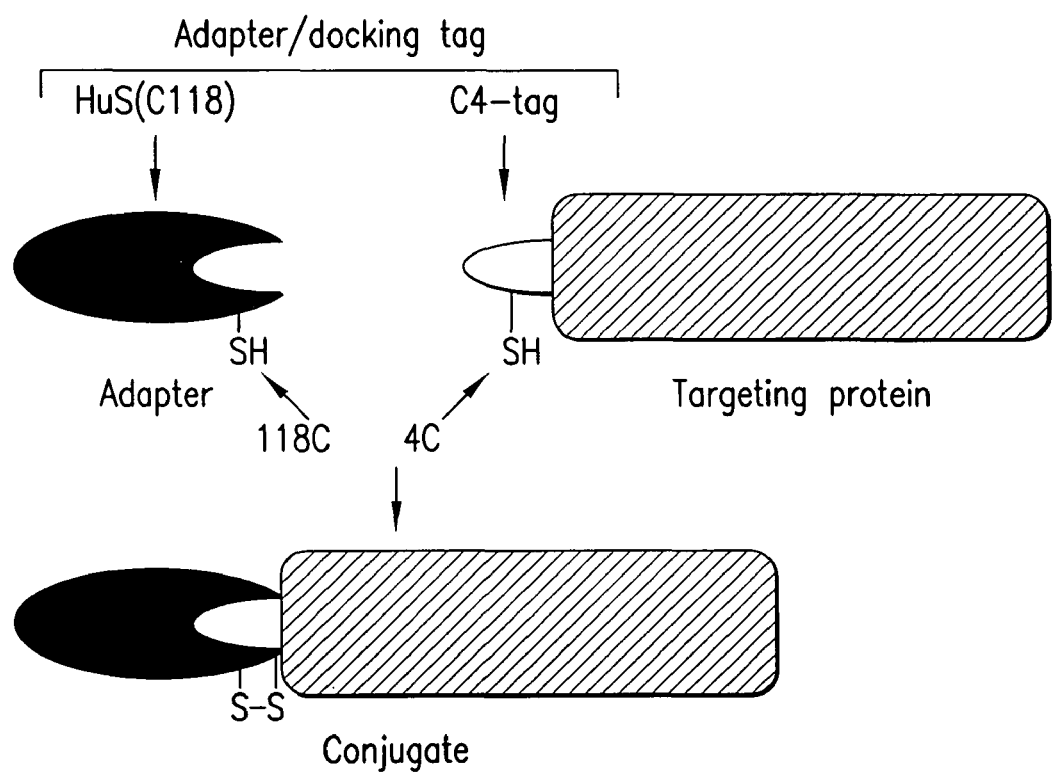
FIG. 2 is a schematic representation of site-specific conjugation between C4-tagged fusion recombinant protein and a complimentary adapter protein, named HuS(C118) (Panel A), a schematic representation of a family of adapter proteins based on human RNase I capable of site-specific conjugation to cysteine residue in C4-tag genetically fused to recombinant protein (Panel B), a demonstration of spontaneous conjugation via a disulfide bond between C4-VEGF and HuS(C118) leading to appearance of DTT-sensitive new protein bands in samples named HuS-C4-VEGF on the SDS-PAGE gel (Panel C), and a demonstration that ribonuclease activity is reconstituted upon chemical conjugate formation, but not upon physical mixing of adapter protein with C4-tagged recombinant fusion protein (Panel D).
Figure 2B:
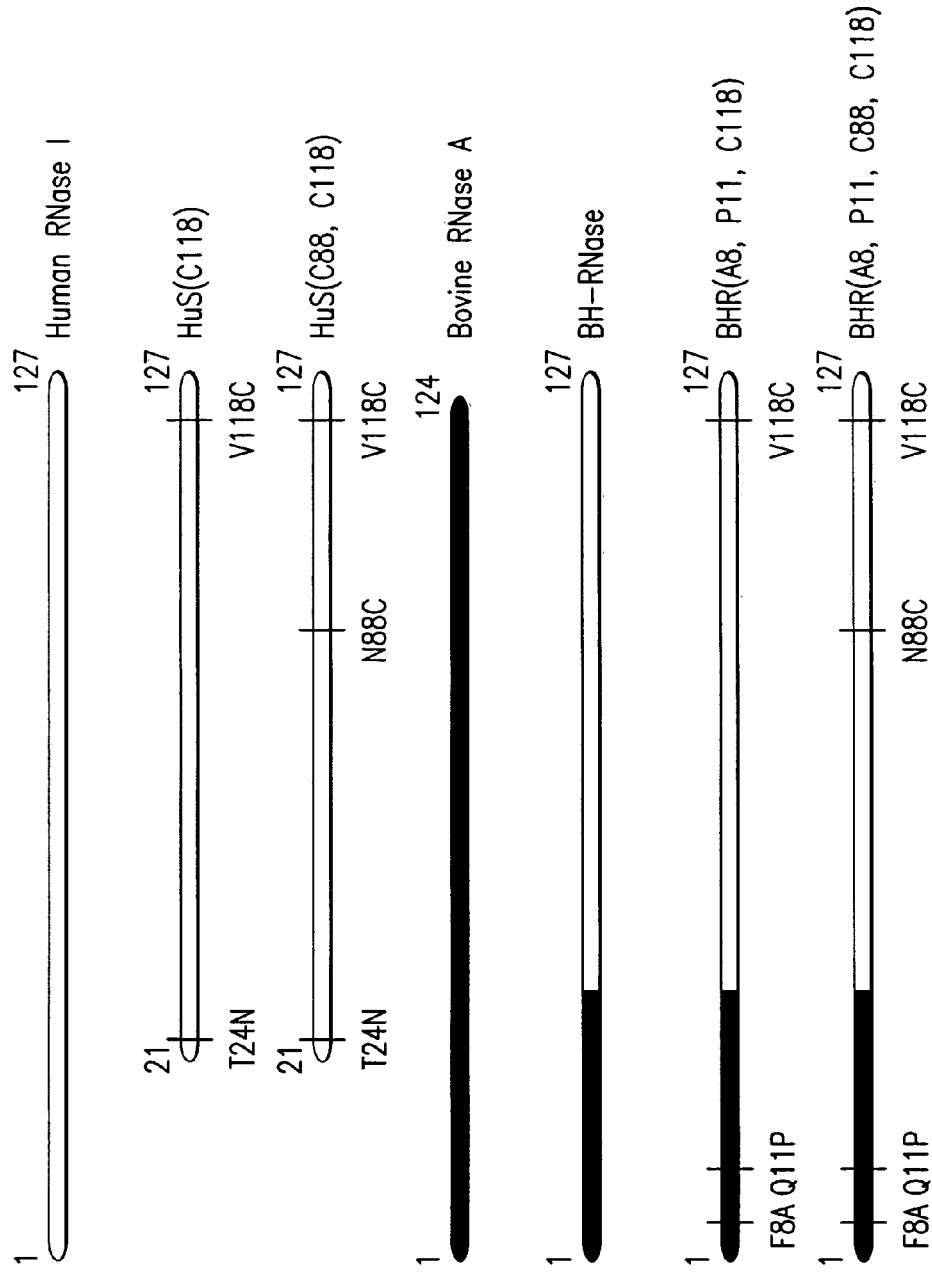
Figure 2C:
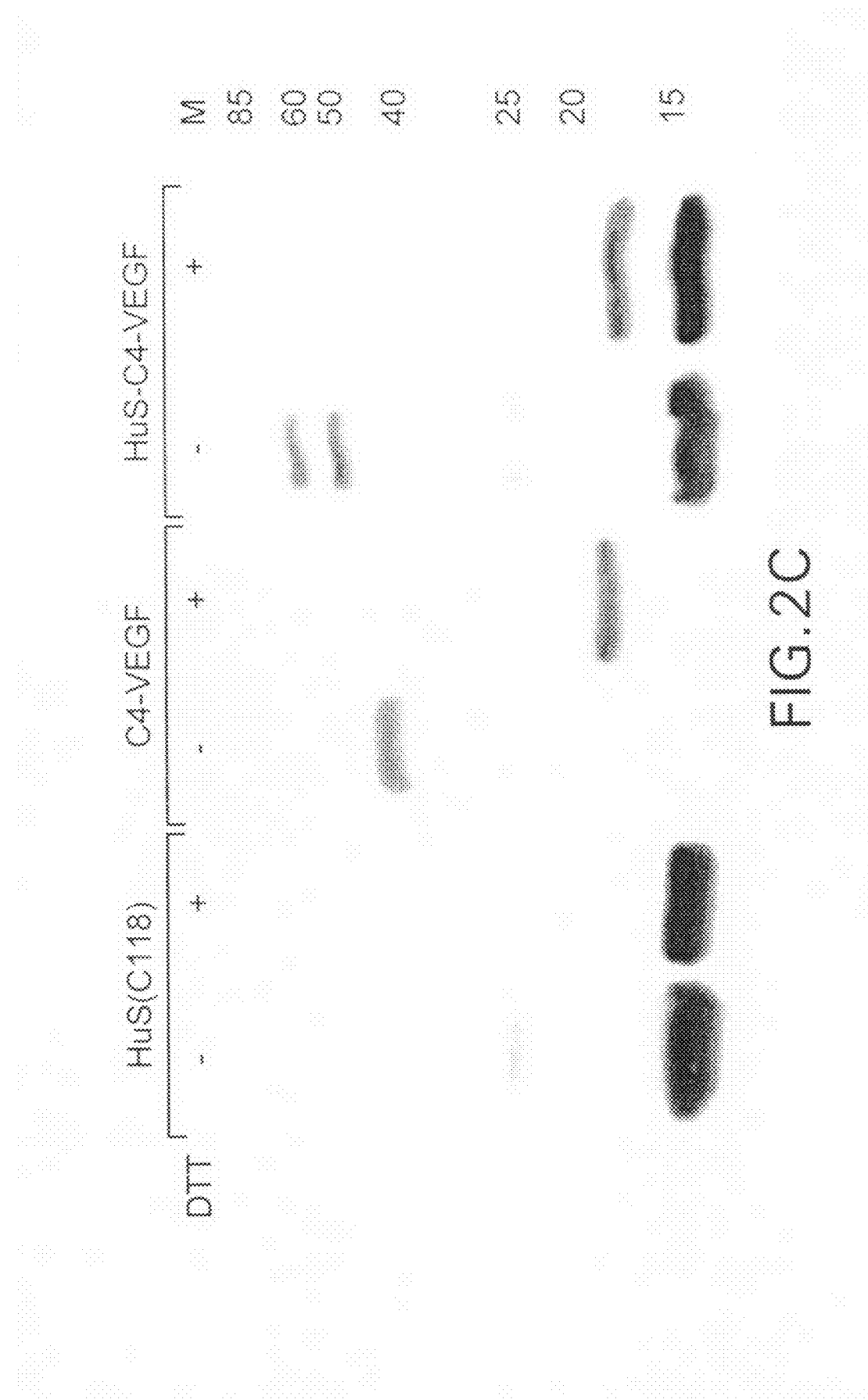
Figure 2D:
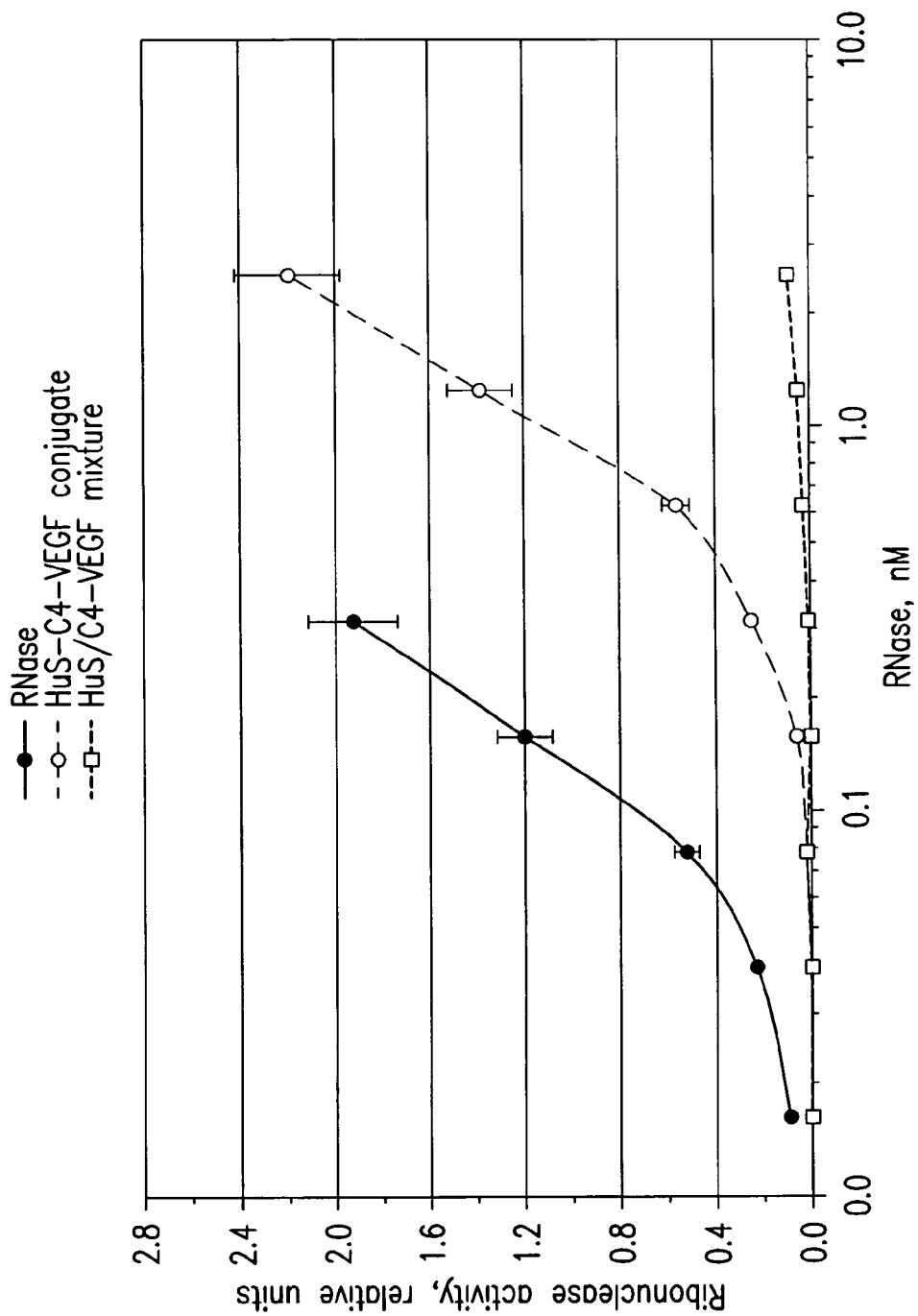

HuS(C118) prepared as described above, and C4-tagged proteins, such as C4-VEGF, or C4-annexin, or C4-LFn, were mixed in a buffer containing 20 mM Tris HCl pH 8.0, incubated at 4° C. for 16 hrs, and then analyzed by SDS-PAGE under reducing and non-reducing conditions. SDS-PAGE analysis under non-reducing conditions revealed new protein products formed in the mixtures during incubation (FIG. 2C, no DTT lanes). The molecular weights of the proteins in these bands corresponded to the molecular weight of conjugates carrying one or two HuS molecules per parental protein, respectively. Under reducing conditions these bands disappeared, and only bands corresponding to parental proteins and 12-kDa HuS(C118) were detectable (FIG. 2C, plus DTT lanes). Conjugates were purified first on Hu-peptide column to remove free HuS(C118) and, when necessary, by ion-exchange chromatography to remove free parental proteins.

Figure 3A:
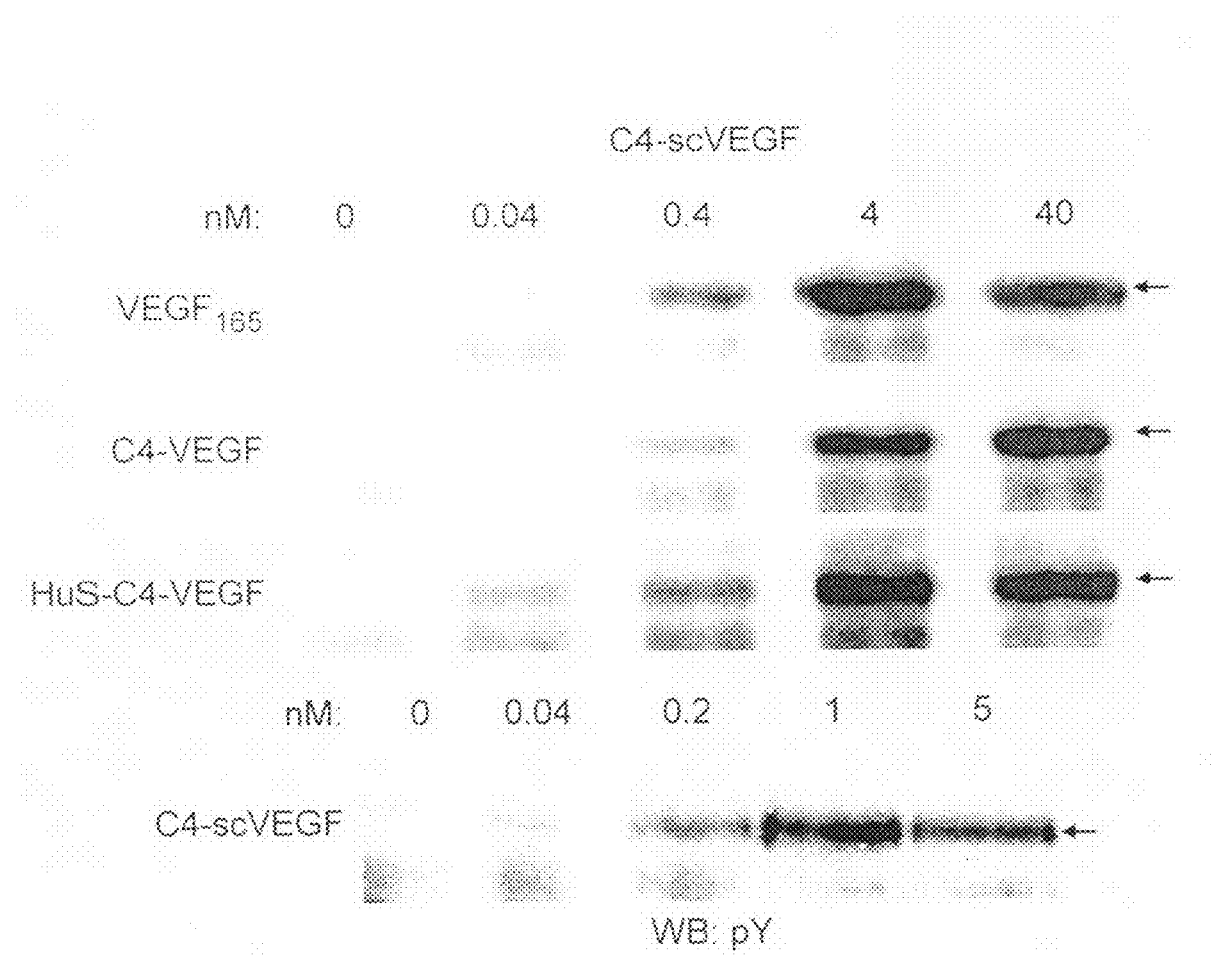
FIG. 3 illustrates that functional activities of several C4-tagged recombinant fusion proteins and C4-tagged recombinant fusion proteins conjugated to complimentary adapter protein are comparable to that of parental proteins. Panel A illustrates that in VEGFR-2 tyrosine phosphorylation assay in 293/KDR cells functional activities of C4-tagged vascular endothelial growth factor, (C4-VEGF), C4-tagged single-chain vascular endothelial growth factor (C4-scVEGF), and HuS(C118)-C4-VEGF conjugate (HuS-C4-VEGF) are comparable with that of VEGF that does not contain C4-tag. Panel B illustrates that functional activities of C4-tagged annexin V (C4-annexin) and HuS(C118)-C4-annexin V conjugates (HuS-C4-annexin) are comparable with that of annexin V in an erythrocyte binding assay. Panel C illustrates that ability of a C4-tagged catalytically inactive fragment of anthrax lethal factor, C4-LFn, and the corresponding HuS(C118)-C4-LFn conjugate (HuS-C4-LFn) are comparable to that of LFn in protection of RAW cells from cytotoxic activity of anthrax toxin LF/PA.
Figure 3B:
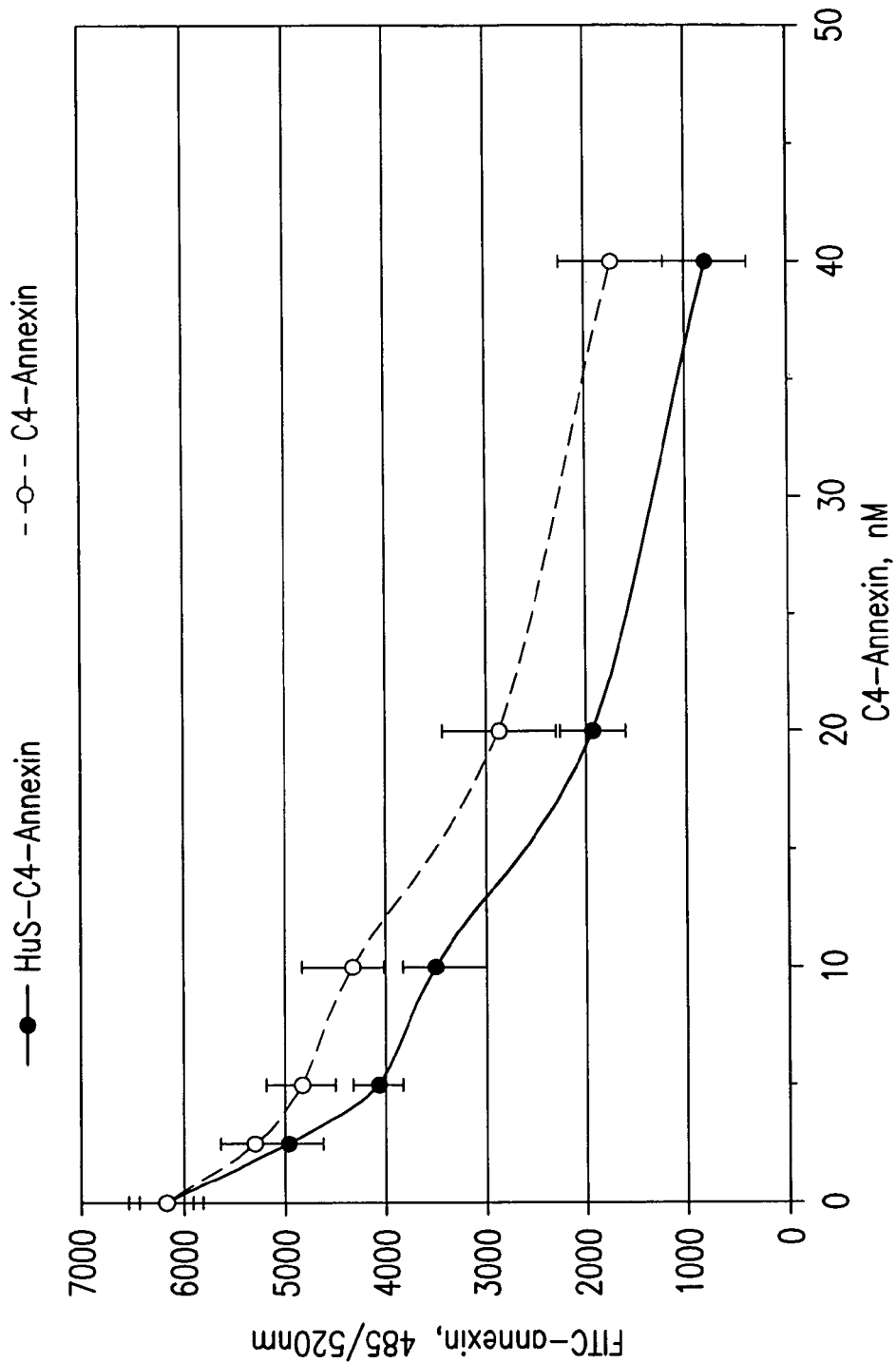
Figure 3C:
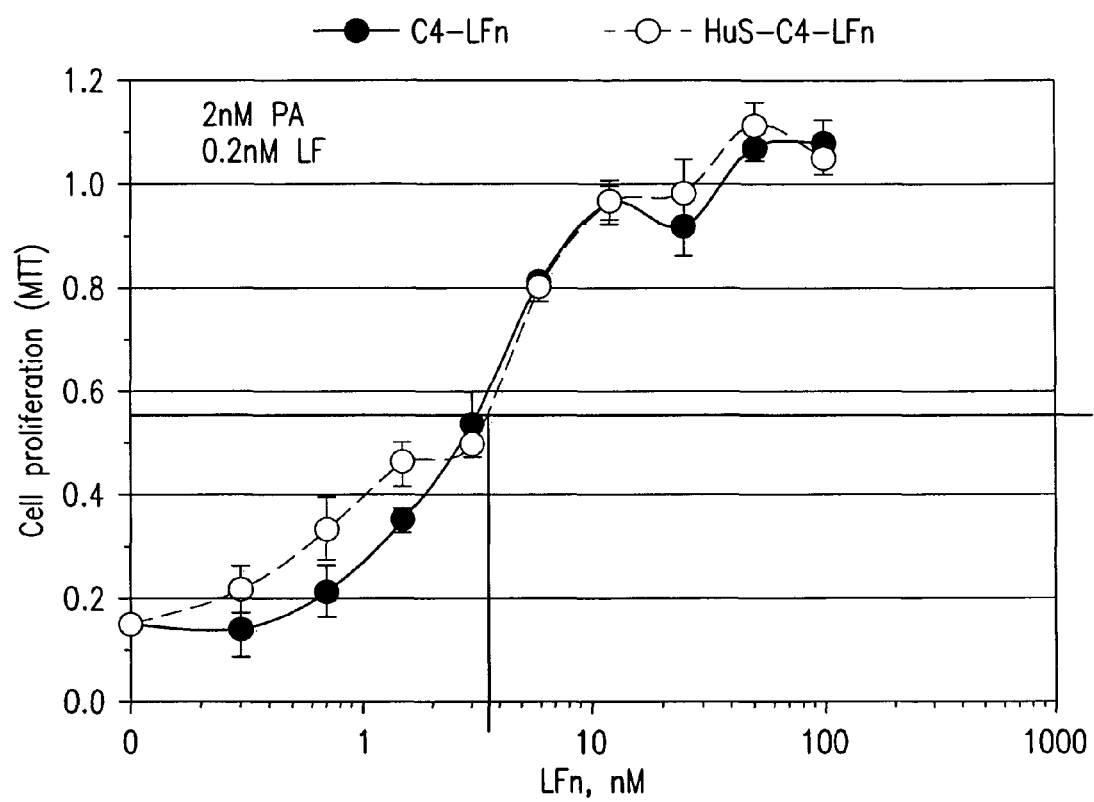

The functional activities of conjugates were tested in tissue culture assays described above. Activity of HuS-C4-VEGF conjugate was similar to that of C4-VEGF in the induction of VEGFR-2 tyrosine autophosphorylation in 293/KDR cells (FIG. 3, Panel A) HuS-C4-annexin conjugate was active in competition with FITC-annexin for binding to phosphatidylserine-displaying erythrocytes of stabilized human blood with IC50 of 11+3 nM for conjugate vs. IC50 of 9+4 nM for recombinant annexin V as reported by Tait et al., (1995) (FIG. 3, Panel B). HuS-C4-LFn was as active as C4-LFn in protection of RAW 264.7 cells from LF in the presence of PA (FIG. 3, Panel C). Together, these data indicate that conjugation of adapter protein to different C4-tagged protein does not destroy their activity.

Example 3

Site-Specific Conjugation of C4-VEGF and C4-scVEGF to Radionuclide Chelator, 5-Maleimido-2-hydraziniumpyridine Hydrochloride The protocol included site-specific conjugation of C4-VEGF and C4-scVEGF to chemically active radionuclide chelator 5-maleimido-2-hydraziniumpyridine hydrochloride (Solulink, San Diego, Calif.), and testing the conjugate in tissue culture.

C4-VEGF, prepared as described above, was mixed with dimethylformamide dissolved 5-maleimido-2-hydraziniumpyridine hydrochloride hereinafter designated as HYNIC at the molar ratio HYNIC/protein 3:1 in a buffer containing 20 mM Tris HCl pH 8.0 and incubated for one hour at room temperature. The product, designated HYNIC-C4-VEGF, was purified on PD-10 column (Amersham, USA) equilibrated with 0.114 M Tricine, pH 6.9. Analytical RP HPLC (FIG. 4, Panel A) was used to determine the concentration of protein by detection of optical density at 216 nm and the concentration of HYNIC by detection of optical density at 310 nm. Under selected conditions the ratio of HYNIC to C4-VEGF in purified HYNIC-C4-VEGF was ~1.

C4-scVEGF, prepared as described above, was conjugated to HYNIC and purified as described above and the ratio of HYNIC to C4-scVEGF in purified product designated HYNIC-C4-VEGF, was ~1.

Figure 4A:
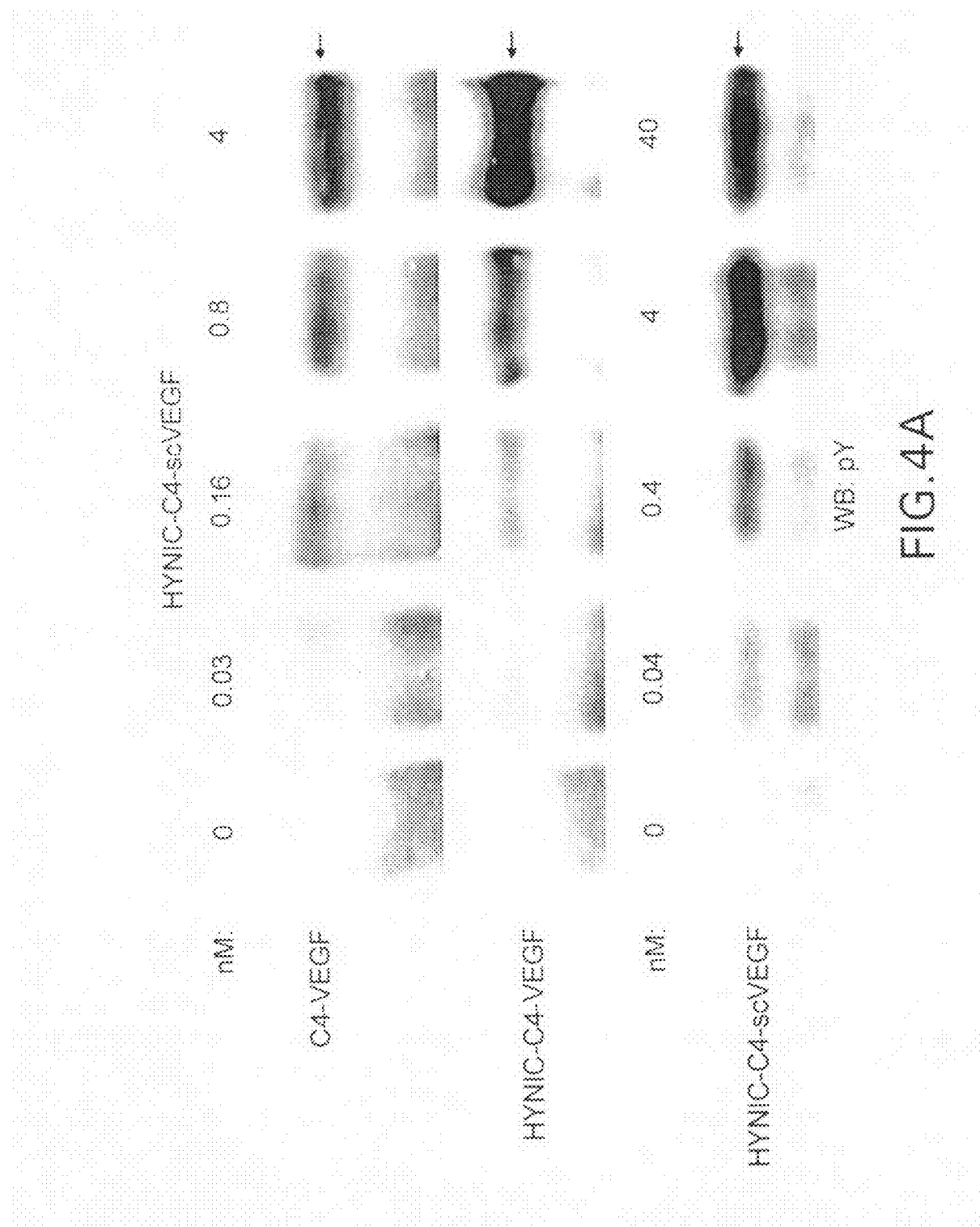
FIG. 4 illustrates site-specific conjugation of HYNIC-maleimide (5-maleimido-2-hydraziniumpyridine hydrochloride), a chelator for $^{99m}$Tc, to C4-VEGF and C4-scVEGF fusion proteins and functional activity of such conjugates. Panel A illustrates that functional activities of HYNIC-C4-VEGF and HYNIC-C4-scVEGF conjugates are comparable to that of parental C4-VEGF in VEGFR-2 tyrosine autophosphorylation assay in 293/KDR cells. Panel B illustrates that HYNIC-C4-VEGF and HYNIC-C4-scVEGF conjugates are comparable with parental C4-VEGF in their abilities to protect 293/KDR cells from cytotoxicicity of toxin-VEGF fusion protein.
Figure 4B:
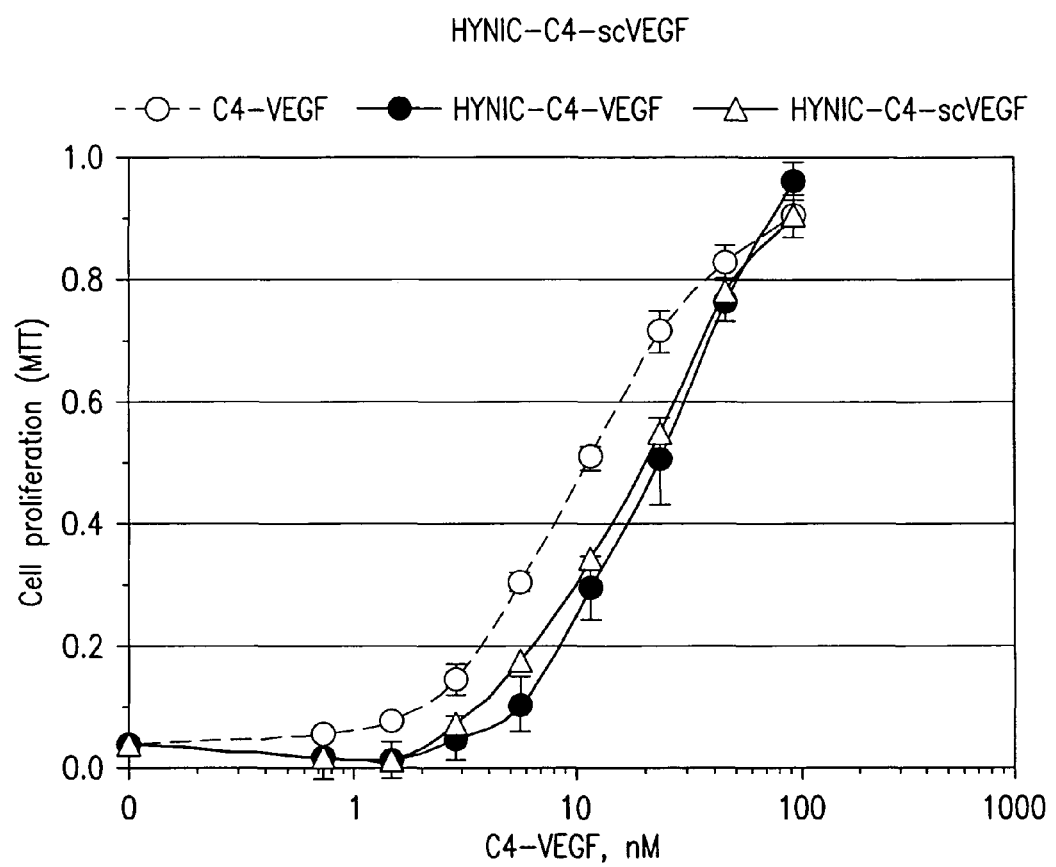

The functional activity of VEGF moiety in HYNIC-C4-VEGF and HYNIC-C4-scVEGF was tested in two tissue culture assays described above, induction of VEGFR-2 tyrosine autophosphorylation in 293/KDR cells (FIG. 4, Panel B) and protection of 293/KDR cells from cytotoxic activity of SLT-VEGF (FIG. 4, Panel C). In both assays activities of HYNIC-C4-VEGF and HYNIC-C4-scVEGF were comparable to that of unmodified C4-VEGF, indicating that conjugation of C4-VEGF or C4-scVEGF to HYNIC does not destroy activity of the protein.

Example 4

Site-Specific Conjugation of C4-VEGF to Polyethyleneglycol

The protocol included site-specific conjugation of C4-VEGF$_{10}$ to polyethyleneglycol functionalized with chemically active maleimide group (Nektar Therapeutics) and testing the conjugate in tissue culture.

Figure 5A:
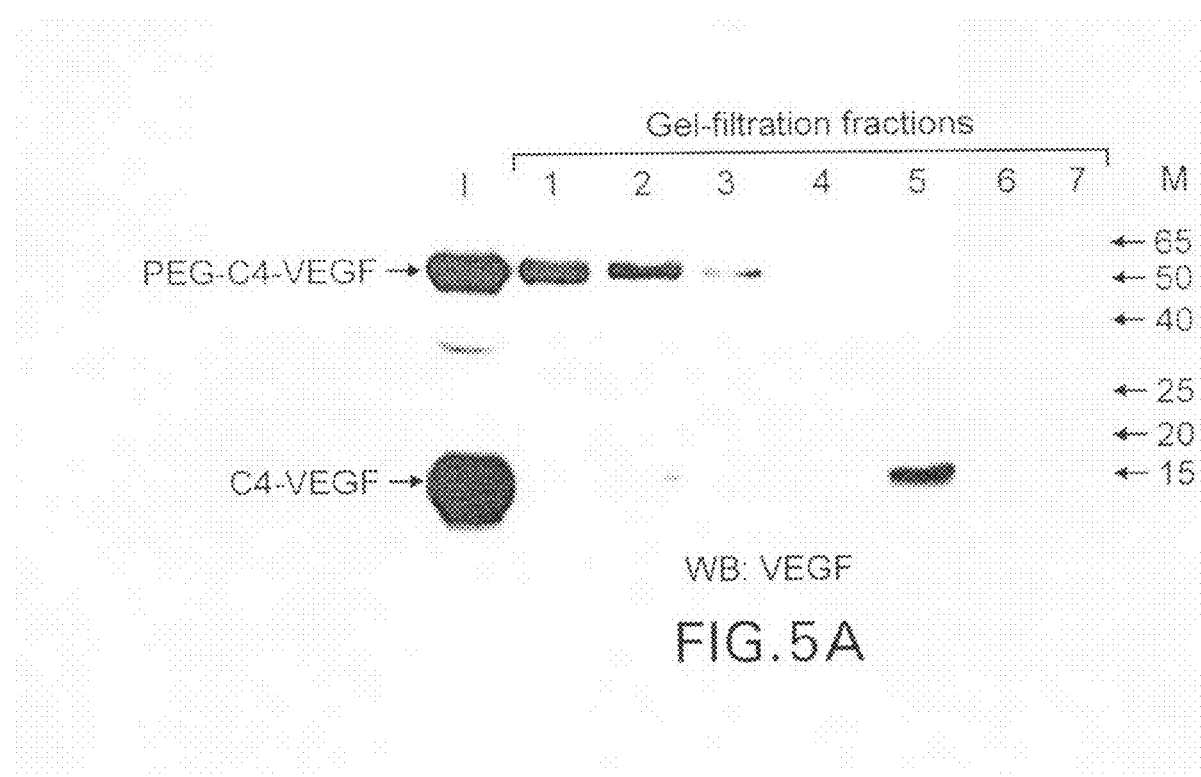
FIG. 5 illustrates site-specific conjugation of 20 kDa or 40 kDa maleimide-polyethyleneglycol (PEG20, and PEG40, correspondingly) to C4-VEGF and functional activity of the PEG-C4-VEGF conjugate. Panel A illustrates SDS-PAGE analysis of PEG-C4-VEGF conjugate. Panel B illustrates that functional activity of PEG-C4-VEGF conjugate is comparable to that of parental C4-VEGF in VEGFR-2 tyrosine autophosphorylation assay in 293/KDR cells.
Figure 5B:
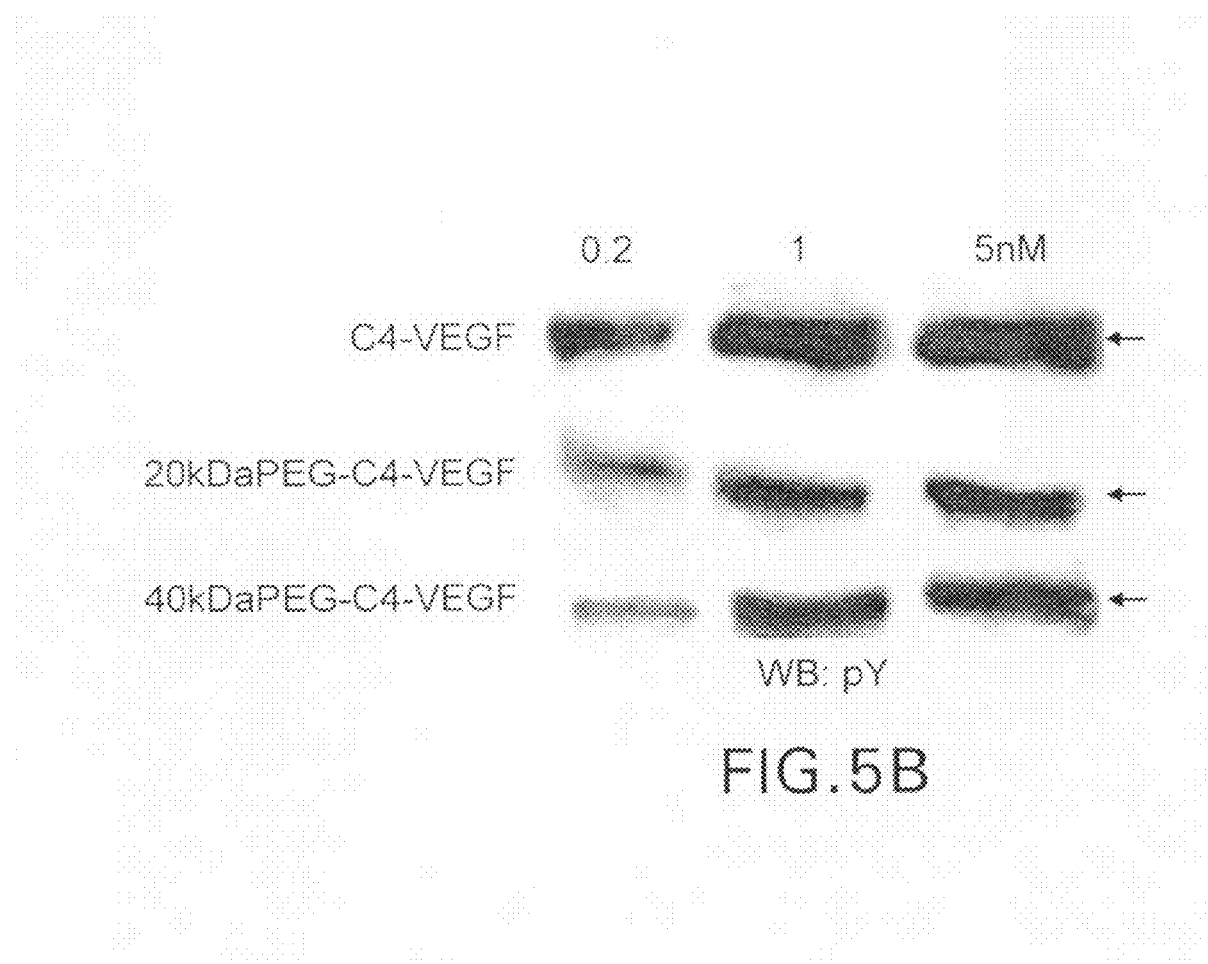

C4-VEGF$_{110}$, prepared as described above, was mixed with either 20 kDa or 40 kDa polyethyleneglycol maleimide (PEG) at PEG to protein ratio of 3:1 and incubated for one hour at room temperature in a buffer containing 20 mM Tris HCl pH 8.0. The products, designated PEG20-C4-VEGF and PEG40-C4-VEGF, were purified from unreacted C4-VEGF and PEG by HPLC gel-filtration on a column equilibrated with 20 mM Tris HCl pH 8.0. Analytical RP HPLC was used to determine the concentration of protein by detection of optical density at 216 nm. Western blot analysis of reduced PEGylated VEGF products with antibody against VEGF revealed a band corresponding to apparent molecular mass of 55 kDa and a band of approximately equal intensity corresponding to unmodified VEGF monomer (FIG. 5, Panel A), indicating that in the majority of the VEGF dimers only one C4-tag was conjugated to PEG.

The functional activity of PEG-C4-VEGF was tested in tissue culture assay of induction of VEGFR-2 tyrosine autophosphorylation in 293/KDR cells (FIG. 5, Panel B for PEG40-C4-VEGF) In this assay activities of PEG-C4-VEGF were comparable to that of unmodified C4-VEGF, indicating that site-specific conjugation of C4-VEGF to polyethyleneglycol does not destroy activity of the protein.

Example 5

Site-Specific Conjugation of Cyanine Dye Cy5.5 to HuS-C4-VEGF Conjugate

Figure 6B:
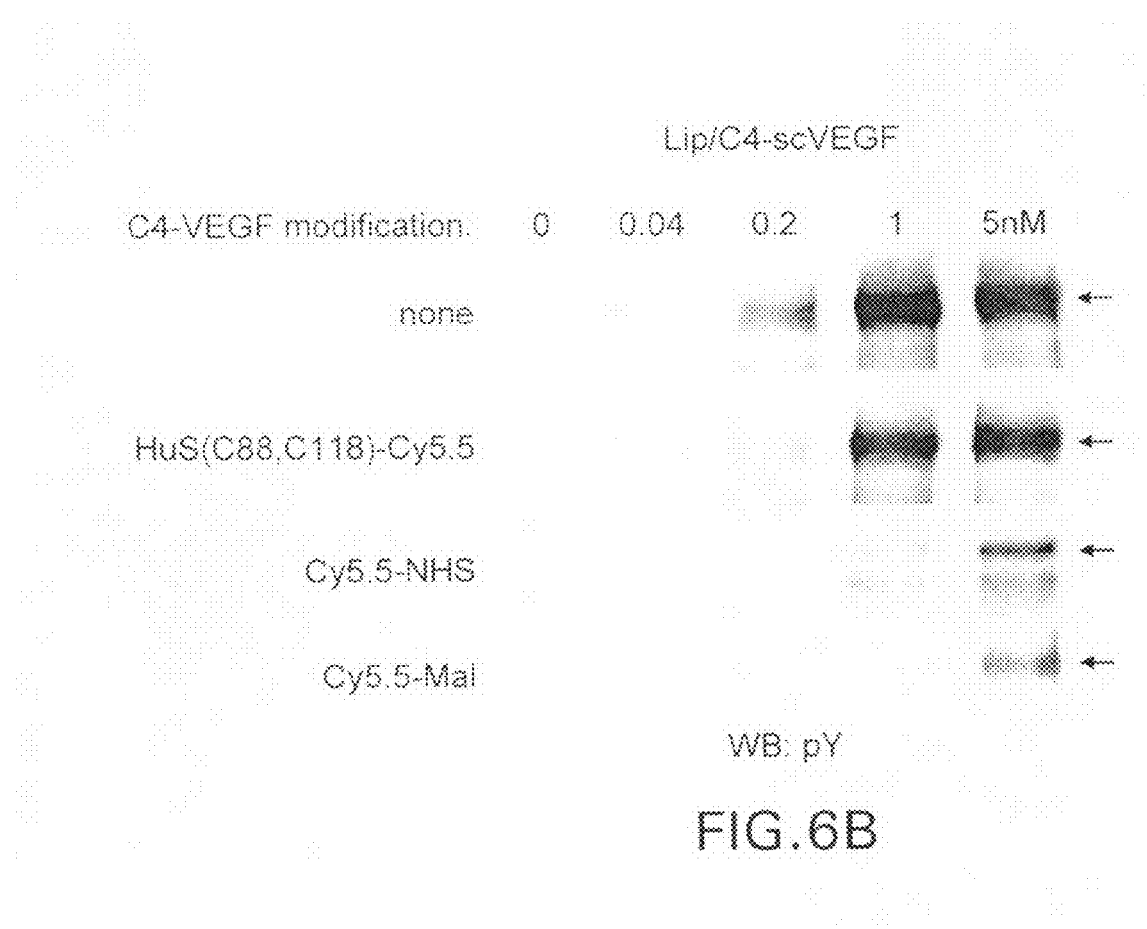
FIG. 6 illustrates the use of C4-tag and a complimentary adapter protein HuS(C88, C118) for construction of VEGF-driven conjugates (Cy5.5-Hus-C4-VEGF) containing cyanine dye Cy5.5 for targeted near-infrared fluorescent imaging in vivo. Panel A is a flow-chart for construction and characterization of Cy5.5-Hus-C4-VEGF conjugate. Panel B illustrates that functional activity of Cy5.5-Hus-C4-VEGF conjugate is comparable to that of parental C4-VEGF in VEGFR-2 tyrosine autophosphorylation assay, while site-specific (Cy5.5-C4-VEGF) or random conjugation (Cy5.5-VEGF) of a similar amount of Cy5.5 per C4-tagged VEGF decreases activity of VEGF. Panel C illustrates that Cy5.5-Hus-C4-VEGF conjugate is comparable to that of parental C4-VEGF in their ability to protect 293/KDR cells from cytotoxicity of toxin-VEGF fusion protein, while site-specific (Cy5.5-C4-VEGF) or random conjugation (Cy5.5-VEGF) of a similar amount of Cy5.5 per C4-tagged VEGF decreases VEGF activity. Panel D illustrates the use of Cy5.5-Hus-C4-VEGF conjugate for in vivo imaging of tumor vasculature.
Figure 6C:
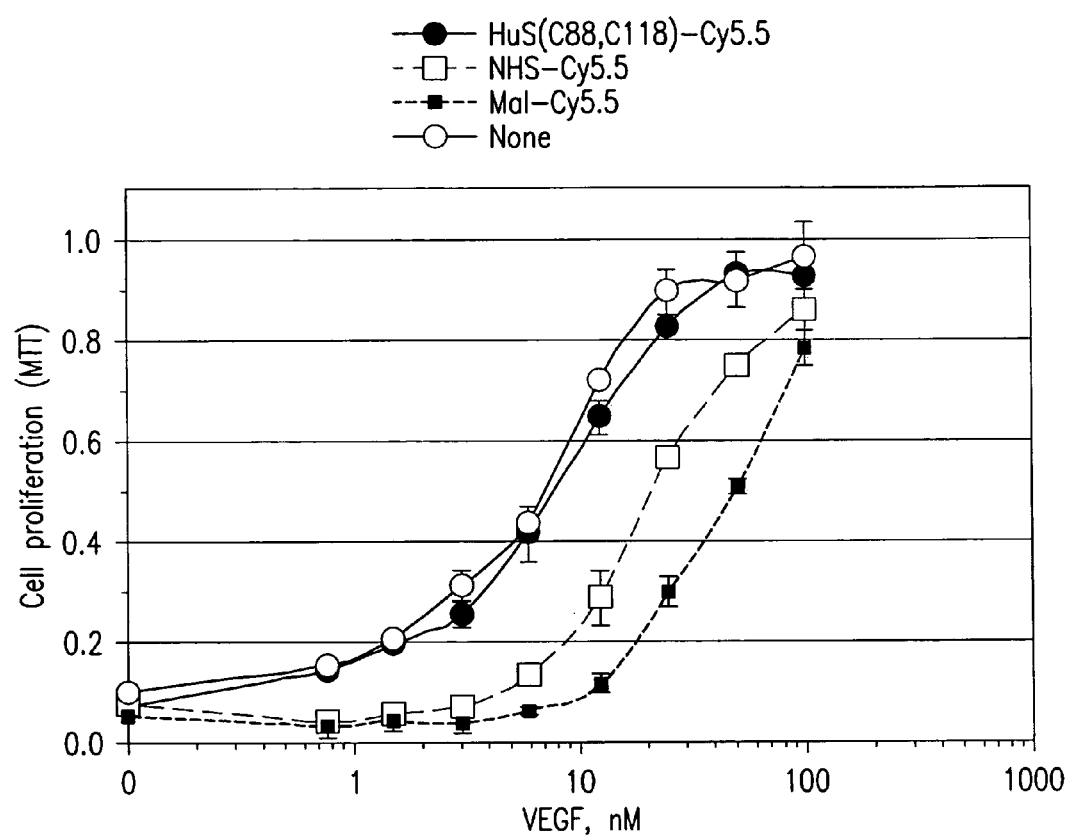

The protocol included preparation of HuS(C88,C118), its conjugation to C4-VEGF, purification of the resulting Hus-C4-VEGF conjugate, and conjugation of said conjugate to a cyanine dye Cy5.5 yielding conjugate named Cy5.5-Hus-C4-VEGF (FIG. 6, Panel A). For comparative purposes, C4-VEGF was either randomly modified with NHS-Cy5.5 on amino groups to the ratio of 1:1, or modified with maleimide-Cy5.5 on C4 residue in the C4-tag. The functional activities of VEGF moiety in all Cy5.5-containing conjugates were tested in two tissue culture assays described above, induction of VEGFR-2 tyrosine autophosphorylation (FIG. 6, Panel B) and protection of 293/KDR cells from cytotoxic activity of SLT-VEGF (FIG. 6, Panel C). In both assays only activities of Cy5.5-Hus-C4-VEGF conjugate were comparable to that of unmodified C4-VEGF, underlying efficacy of using an adapter protein capable of binding to C4-tag for derivatization of proteins.

The utility of Cy5.5-Hus-C4-VEGF for imaging was tested in Balb/c female mice bearing subcutaneous 4T1 mouse mammary adenocarcinoma tumors. Images obtained with KODAK Image Station 2000MM equipped with a band-pass filter at 630 nm and a long-pass filter at 700 nm indicated that Cy5.5-HuS-C4-VEGF conjugate preferentially localized to the periphery of primary tumor (FIG. 6, Panel D). This preferential localization was inhibited in mice pretreated with SLT-VEGF protein that destroys VEGFR-2 positive cells in tumors (Backer et al., submitted), indicating that accumulation of Cy5.5-HuS-C4-VEGF conjugate in tumor is VEGF-receptor mediated and can be used for specific imaging of tumor vasculature.

Example 6

The Use of C4-Tag and an Adapter Protein Covalently Bound to this Tag for Construction of VEGF-Driven Conjugates Containing Drug-Loaded Liposomes for Targeted Drug Delivery The protocol included preparation of HuS(C118), its conjugation to PEG-lipid-maleimide, insertion of lipidated HuS (C118) into doxorubicin-loaded liposomes, that leads to a standardized construct named Lip/HuS(C118), and conjugation of this construct to C4-VEGF, that yielded Lip/Hus-C4-VEGF (FIG. 7, Panel A). The functional activity of VEGF moiety in Lip/Hus-C4-VEGF conjugate were tested in a tissue culture assay described above, induction of VEGFR-2 tyrosine phosphorylation in 293/KDR cells (FIG. 7, Panel B). In this assay VEGF activity of Lip/Hus-C4-VEGF liposomes was comparable to that of unmodified C4-VEGF, underlying efficacy of using an adapter protein capable of binding to C4-tag for derivatization of proteins.

Figure 7A:
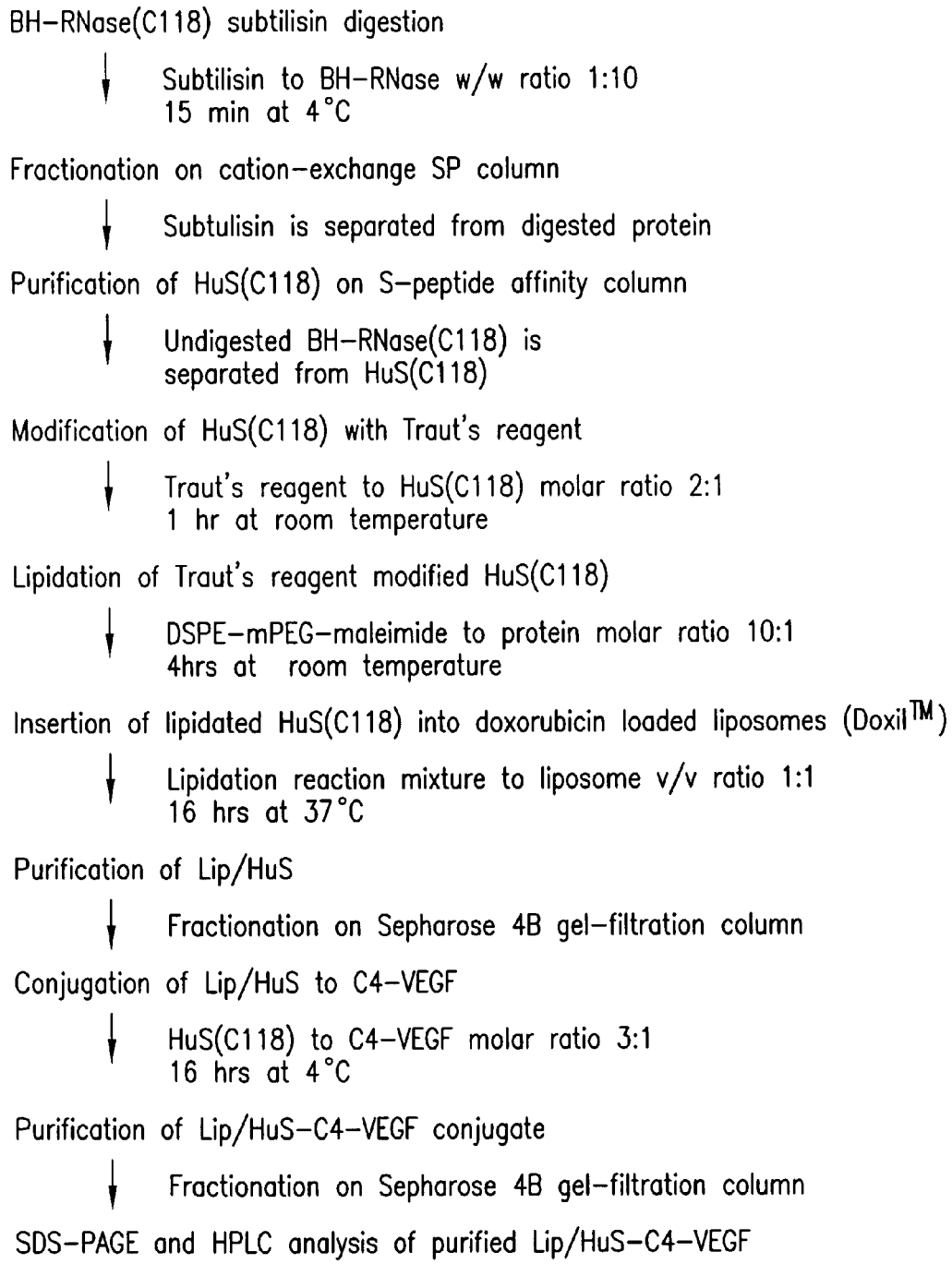
FIG. 7 illustrates the use of C4-tag and a complimentary adapter protein HUS(C118) for construction of VEGF-driven conjugates (Lip/Hus-C4-VEGF) containing doxorubicin-loaded liposomes ("DOXIL") for targeted drug delivery. Panel A is flow-chart for construction and characterization of Lip/Hus-C4-VEGF conjugate. Panel B illustrates that functional activity of Lip/Hus-C4-VEGF conjugate is comparable with that of parental C4-VEGF in VEGFR-2 tyrosine autophosphorylation assay. Panel C illustrates that VEGF-targeted doxorubicin-loaded liposomes (Lip/HuS-C4-VEGF) are toxic to VEGFR-2 expressing cells in a concentration range where untargeted doxorubicin-loaded liposomes are ineffective underlying receptor-mediated mechanism of toxicity of Lip/Hus-C4-VEGF conjugate. Panel D illustrates that VEGF protects 293/KDR cells from cytotoxic activity of Lip/Hus-C4-VEGF conjugate.
Figure 7B:
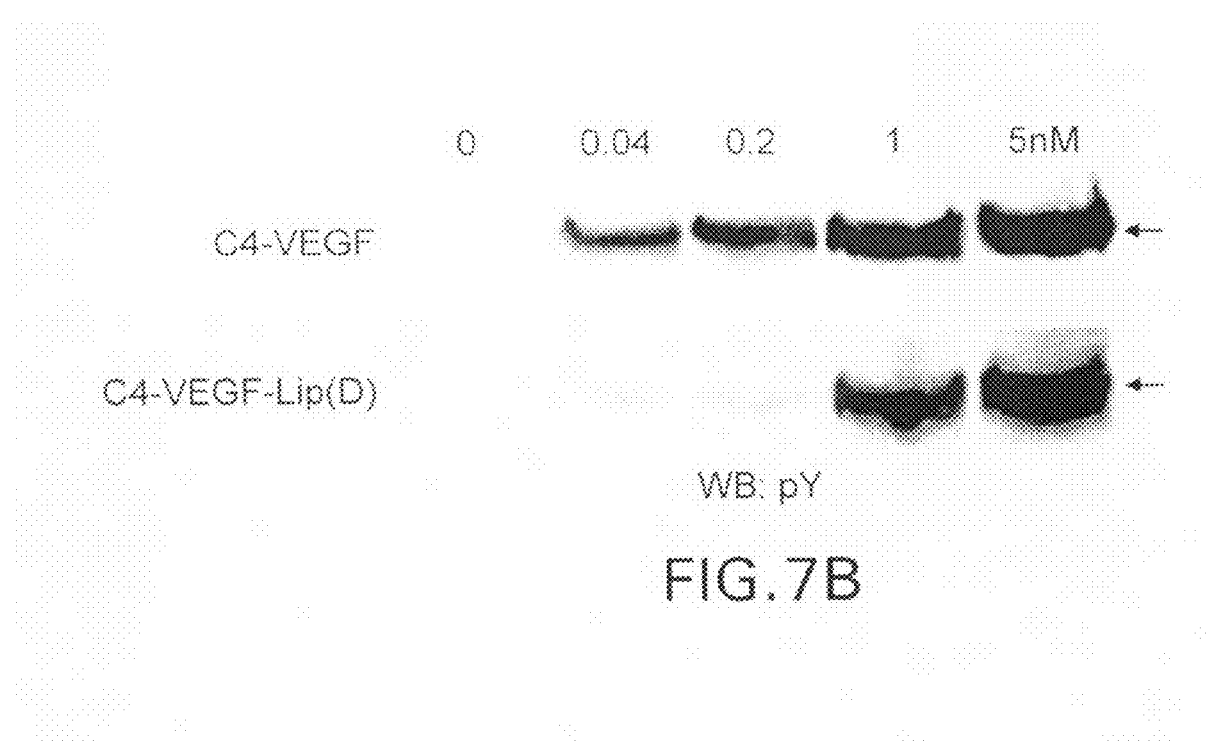
Figure 7C:
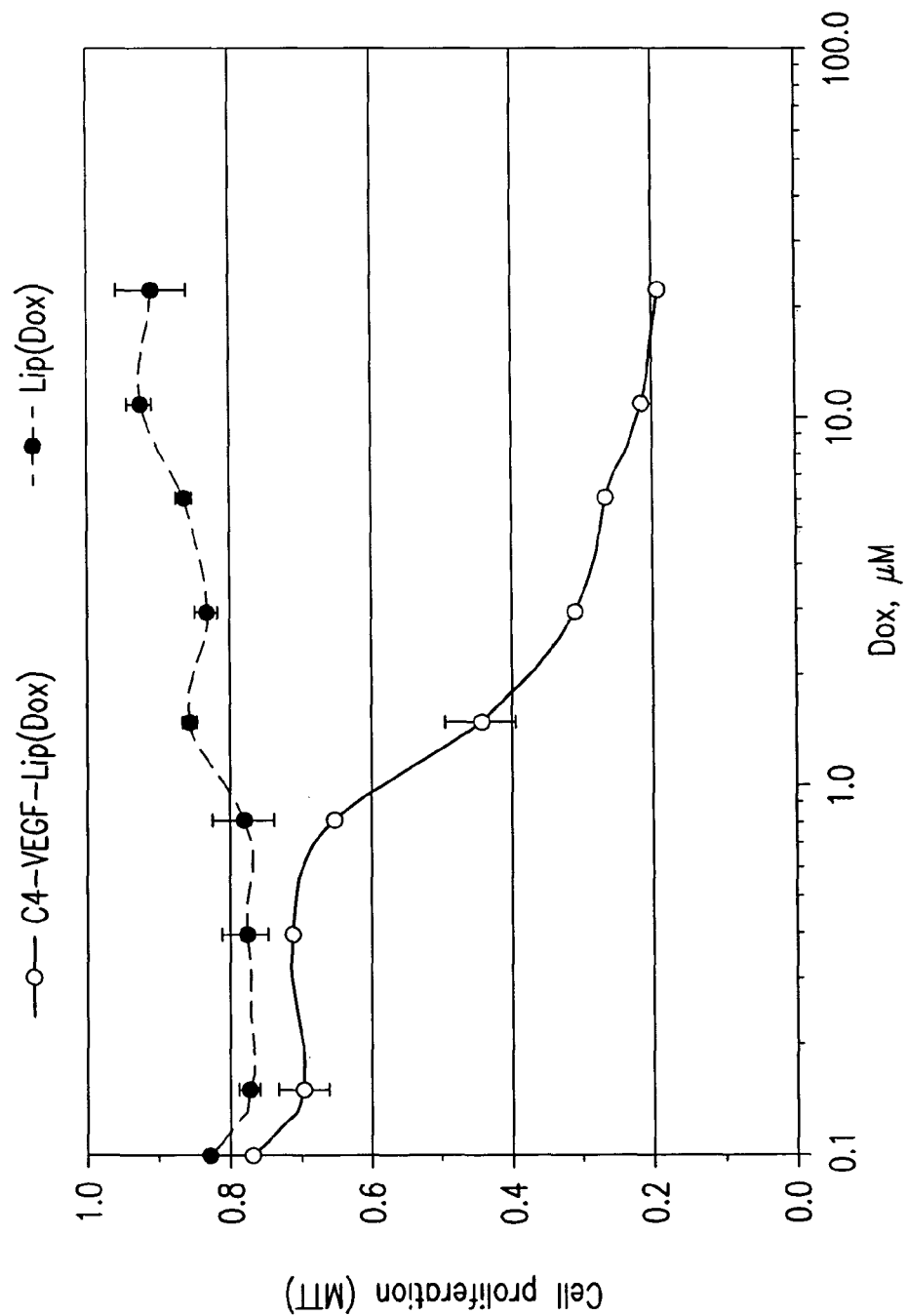
Figure 7D:
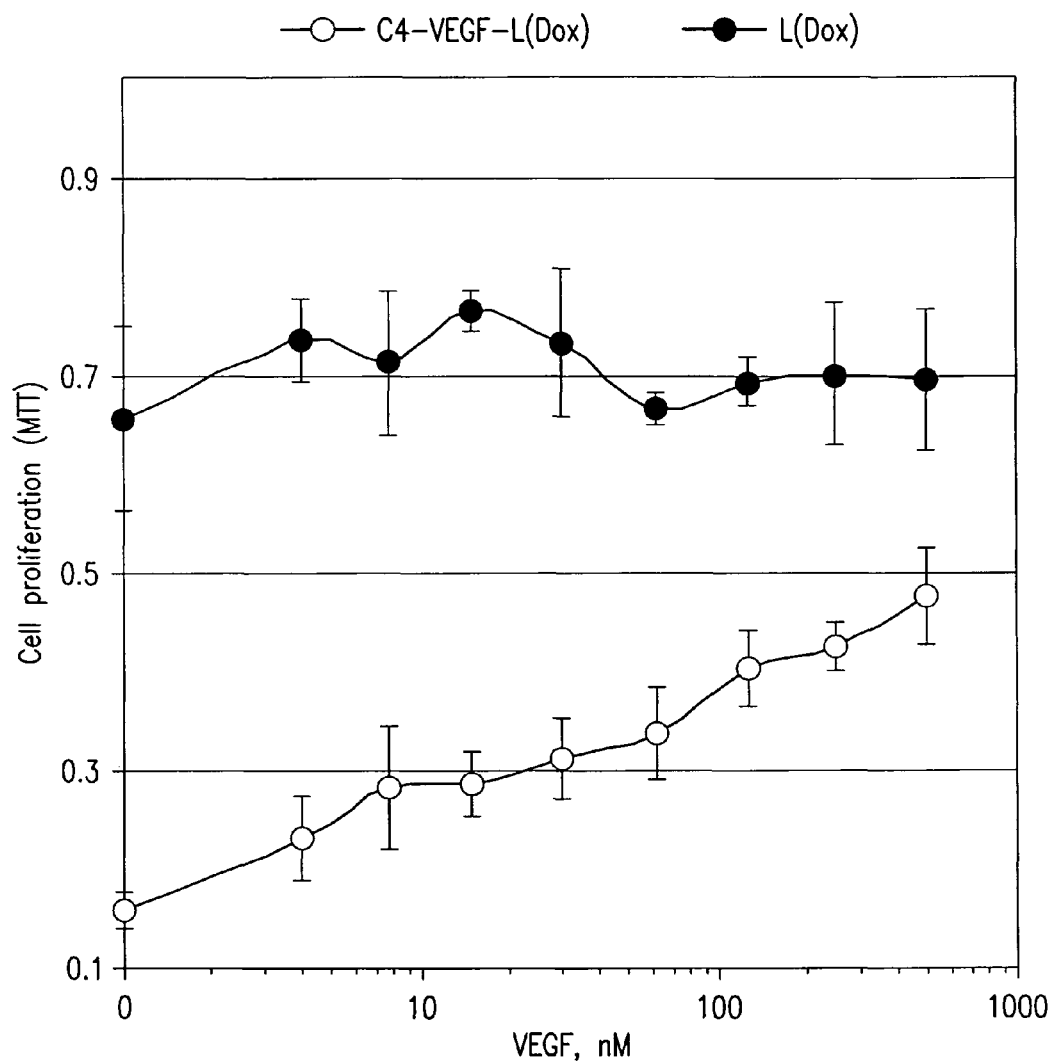

A 15-min exposure of 293/KDR cells to Lip/HuS-C4-VEGF resulted in a dose-dependent inhibition of cell growth (FIG. 7, Panel C), while equivalent amounts of untargeted doxorubicin-loaded liposomes (commercially available under the trade name "DOXIL") derivatized with HuS(C118) alone were not toxic for these cells indicating a VEGF receptor-mediated mechanism of cytotoxicity of Lip/Hus-C4-VEGF targeted liposomes. This mechanism was further confirmed by ability of VEGF to inhibit of cytotoxicity of Lip/Hus-C4-VEGF in a dose-dependent manner (FIG. 7D).

Example 7

Figure 8A:
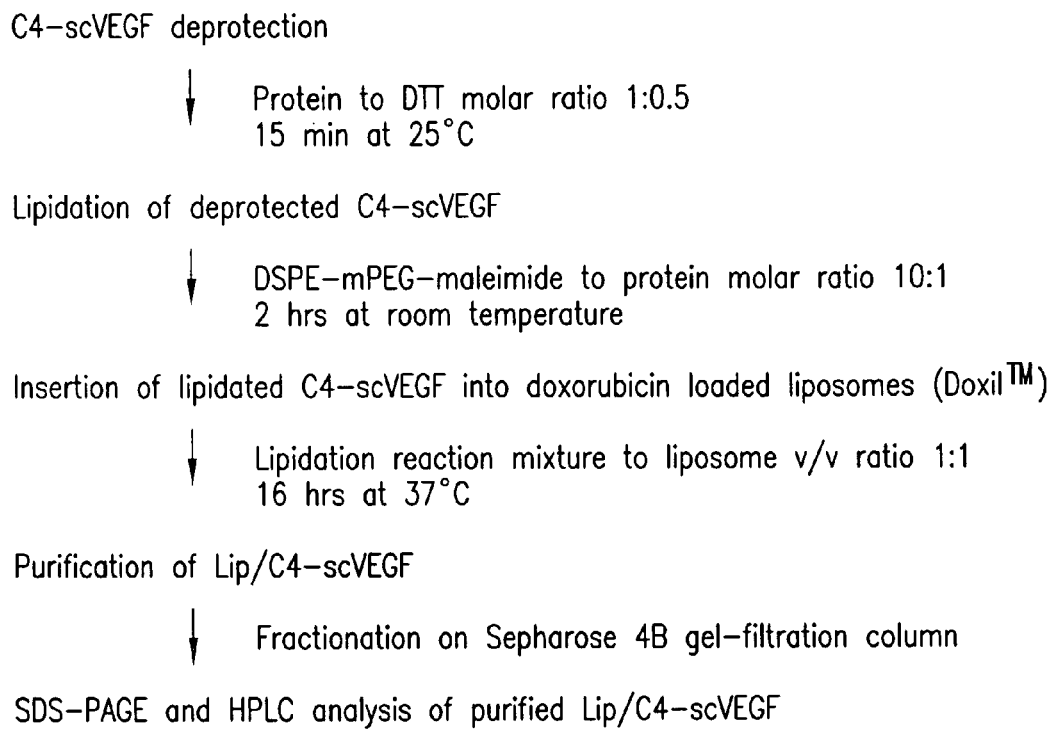
FIG. 8 illustrates the use of C4-scVEGF for construction of VEGF-driven conjugates (Lip/C4-scVEGF) containing doxorubicin-loaded liposomes ("DOXIL") for targeted drug delivery. Panel A is a flow-chart for construction and characterization of Lip/C4-scVEGF conjugate. Panel B illustrates that in VEGFR-2 tyrosine autophosphorylation assay functional activity of Lip/C4-scVEGF conjugate is comparable with that of parental C4-VEGF. Panel C illustrates that Lip/C4-scVEGF are toxic to VEGFR-2 expressing cells in a concentration range where untargeted doxorubicin-loaded liposomes are ineffective underlying receptor-mediated mechanism of toxicity of Lip/C4-scVEGF conjugate. Panel D illustrates that VEGF protects 293/KDR cells from cytotoxic activity of Lip/C4-scVEGF conjugate.
Figure 8B:
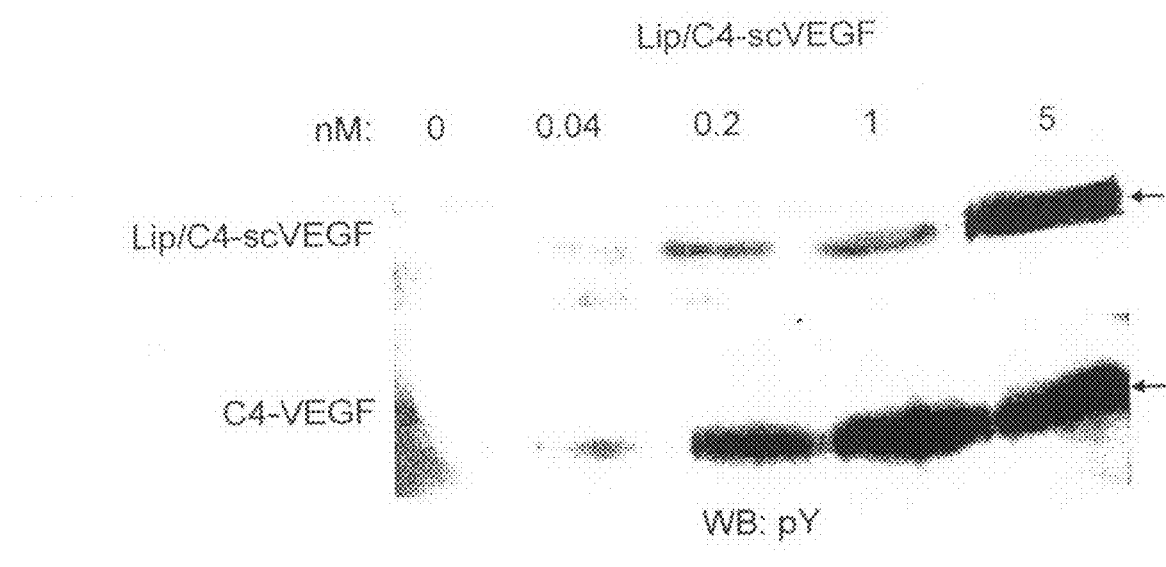

The Use of C4-Tag for Construction of Scvegf-Driven Conjugates Containing Drug-Loaded Liposomes for Targeted Drug Delivery The protocol included preparation of C4-scVEGF its conjugation to PEG-lipid-maleimide, and insertion of lipidated C4-scVEGF into doxorubicin-loaded liposomes ("DOXIL") (FIG. 8, Panel A). The functional activity of VEGF moiety in Lip/C4-scVEGF conjugate were tested in a tissue culture assay described above, induction of VEGFR-2 tyrosine phosphorylation in 293/KDR cells (FIG. 8, Panel B). In this assay VEGF activity of Lip/C4-scVEGF liposomes was comparable to that of unmodified C4-VEGF, underlying efficacy of using C4-scVEGF.

Figure 8D:
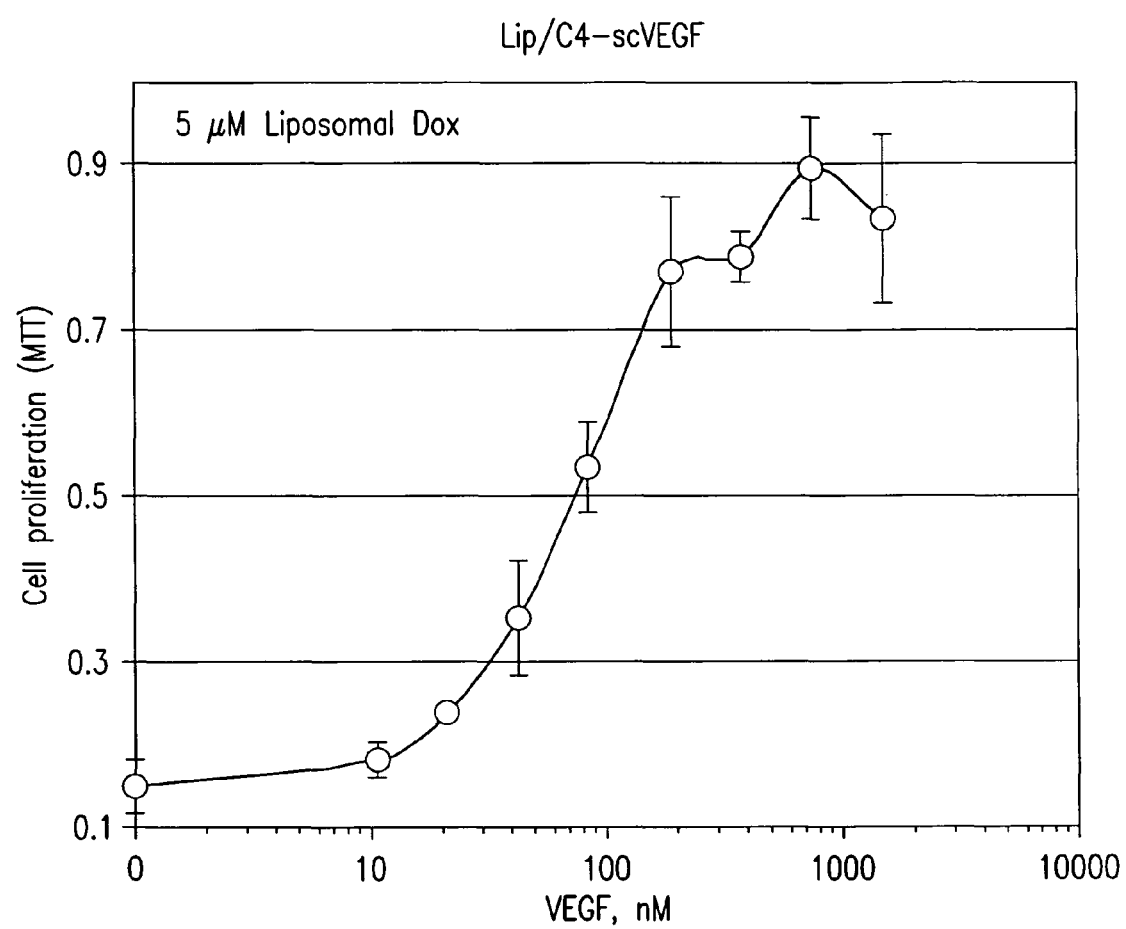

A 15-min exposure of 293/KDR cells to Lip/C4-scVEGF resulted in a dose-dependent inhibition of cell growth (FIG. 8, Panel C), while equivalent amounts of untargeted doxorubicin-loaded liposomes ("DOXIL") were not toxic for these cells indicating a VEGF receptor-mediated mechanism of cytotoxicity of Lip/C4-scVEGF targeted liposomes. This mechanism was further confirmed by ability of VEGF to inhibit cytotoxicity of Lip/Hus-C4-VEGF in a dose-dependent manner (FIG. 8D).

REFERENCES

Adams, G. P., McCartney, J. E., Tai, M. S., Oppermann, H., Huston, J. S., Stafford, W. F., Bookman, M. A., Fand, I., Houston, L. L., Weiner, L. M. (1993) Highly specific in vivo tumour targeting by monovalent and divalent forms of 741F8 anti-c-erbB-2 single-chain Fv. Cancer Res. 53, 4026-4034.

Albrecht, H., Burke, P. A., Natarajan, A., Xiong, C. Y., Kalicinsky, M., DeNardo, G. L., and DeNardo, S. J. (2004) Production of soluble ScFvs with C-terminal-free thiol for site-specific conjugation or stable dimeric ScFvs on demand. Bioconjugate Chemistry. 15, 16-26.

Backer, M. V., and Backer, J. M. (2001) Targeting endothelial cells overexpressing VEGFR-2: selective toxicity of Shiga-like toxin-VEGF fusion proteins. Bioconj. Chem. 12, 1066-1073.

Backer, M. V., and Backer, J. M. (2001a) Functionally active VEGF fusion proteins. Protein. Exp. Purif. 23, 1-7.

Backer, M. V., Gaynutdinov, T., Aloise, R., Przekop, K., and Backer, J. M. (2002a) Engineering the bovine S-protein for targeted modification. Prot. Express. Purif. 26, 455-461.

Backer, M. V., Gaynutdinov, T. I., Gorshkova, I. I., Crouch, R. J., Hu, T., Aloise, R., Arab, M., Przekop, K., and Backer, J. B. (2003) Humanized docking system for assembly of targeting drug delivery complexes. J. Contr. Release, 89, 499-511.

Backer, M. V., Gaynutdinov, T., Patel, V., Jehning, B., Myshkin, E., and Backer, J. M. (2004) Adapter protein for site-specific conjugation of payloads for targeted drug delivery. Bioconj. Chem. 15, 1021-1029.

Bentz, H., Schroeder, J. A., and Estridge, T. D. (1998) Improved local delivery of TGF-β2 by binding to injectable fibrillar collagen via difunctional polyethylene glycol. J. Biomed. Mater. Res. 39, 67-123.

Dubowchik, G. M, and Walker, M. A. (1999) Receptor-mediated and enzyme-dependent targeting of cytotoxic anticancer drugs. Pharmacol Ther. 83, 67-123

Evans, T. C., Benner, J., and Xu, M. Q. (1999) The in vitro ligation of bacterially expressed proteins using an intein from *Methanobacterium thermoautotrophicum*. J Biol Chem. 274, 3923-3926

Futami, J., Tada, H., Seno, M., Ishikami, S., Yamada, H. (2000) Stabilization of human RNase 1 by introduction of a disulfide bond between residues 4 and 118. J. Biochem. 128, 245-250.

Gaynutdinov, T., Myshkin, E., Backer, J. M., and Backer, M. V. (2003) Chimeric ribonuclease as a source of human adapter protein for targeted drug delivery. Prot. Eng. 16, 771-775.

Gupta, S., Eastman, J., Silski, C., Ferkol, T., and Davis, P. B. (2001) Single chain Fv: a ligand in receptor-mediated gene delivery. Gene Ther. 8, 586-592.

Hofmann, R. M. and Muir, T. W. (2002) Recent advances in the application of expressed protein ligation to protein engineering. Current Opin. Biotech. 13, 297-303.

Kipriyanov, S. M., Dubel, S., Breitling, F., Konterman, R. D., Little, M. (1994) Recombinant single-chain Fv fragments carrying C-terminal cysteine residues: production of bivalent and biotinylated miniantibodies. Mol. Immunol. 31, 1047-1058.

Kuhl, P. R. and Griffith-Cima, L. G. (1996) Tethered epidermal growth factor as a paradigm for growth factor-induced stimulation from the solid phase. Nature Medicine. 2, 1022-1027.

Li, L., Olafsen, T., Anderson, A. L., Wu, A., Raubitschek, A. A., Shively, J. E. (2002) Reduction of kidney uptake in radiometal labeled peptide linkers conjugated to recombinant antibody fragments. Site-specific conjugation of DOTA-peptides to a Cys-diabody. Bioconjugate Chem. 13, 985-995.

Lovrinovic, M., Seidel, R., Wacker, R., Schroeder, H., Seitz, O., Engelhard, M., Goody, R. S., and Niemeyer, C. M. (2003) Synthesis of protein-nucleic acid conjugates by expressed protein ligation. Chem. Commun. 822-823.

Macmillan, D., and Bertozzi, C. R. (2000) New directions in glycoprotein engineering. Tetrahedron 56, 9515-9525.

Mann, B. M., Schmedlen, R. H., West, J. L. (2001) Tethered-TGF-□ increases extracellular matrix production of vascular smooth muscle cells. Biomaterials, 22, 439-444.

Marty, C., Scheidegger, P., Ballmer-Hofer, K., Klemenz, R., and Schwendener, R. A. (2001) Production of functionalized single-chain Fv antibody fragments binding to the ED-B domain of the B-isoform of fibronectin in *Pichia pastoris*. Prot. Expres. & Purif. 21, 156-164.

Mukhopadhyay, J., Kapanidis, A. N., Mekler, V., Kortkhonjia, E., Ebright, Y. W., Ebright, and R. H. (2001) Translocation of sigma(70) with RNA polymerase during transcription: Fluorescence resonance energy transfer assay for movement relative to DNA. Cell 106, 453-463.

Renard, M., Belkadi, L., Hugo, N., England, P., Altschuh, D., and Bedouelle, H. (2002) Knowledge-based design of reagentless fluorescent biosensors from recombinant antibodies. J. Mol. Biol. 318, 429-442.

Schmiedl, A., Breitling, F., Winter, C. H., Queitsch, I., and Dubel, S. (2000) Effects of unpaired cysteines on yield, solubility and activity of different recombinant antibody constructs expressed in *E. coli*. J. Immunol. Meth. 242, 101-114.

Tait, J. F., Engelhardt, S., Smith, C., and Fujikawa, K. (1995) Pourokinase-annexin V chimeras. Construction, expression, and characterization of recombinant proteins. J. Biol. Chem. 270, 21594-21599.

Tolbert, T. J., and Wong, C. H. (2000) Intein-mediated synthesis of proteins containing carbohydrates and other molecular probes. J. Am. Chem. Soc. 122, 5421-5428.

Wang, D., Berven, E., Li, Q., Uckun, F., Kersey, J. H. (1997) Optimization of conditions for formation and analysis of anti-CD19 FVS191 single-chain Fv homodimer (scFv¢)$_2$. Bioconjugate Chem. 8, 64-70.

Wood, R. J., Pascoe, D. D., Brown, Z. K., Medlicott, E. M., Kriek, M., Neylon, C., and Peter L. Roach, P. L. (2004) Optimized Conjugation of a Fluorescent Label to Proteins via Intein-Mediated Activation and Ligation. Bioconjugate Chem. 15, 366-372.

Xu, L., Huang, C. C., Huang, W., Tang, W. H., Rait, A., Yin, Y. Z., Cruz, I., Xiang, L. M., Pirollo, K. F., and Chang, E. H. (2002) Systemic tumor-targeted gene delivery by anti-transferrin receptor scFv-immunoliposomes. Mol. Cancer Therap. 1, 337-346.

What is claimed is:

1. An isolated polypeptide, consisting of the sequence of SEQ ID NO:2.

2. An isolated polypeptide, comprising the sequence of SEQ ID NO:4.

3. An isolated polypeptide having an amino acid sequence comprising the polypeptide sequence of SEQ ID NO: 2 and the polypeptide sequence of a selected targeting protein selected from the group consisting of growth factors, human annexin V, and a catalytically inactive fragment of anthrax lethal factor.

4. The isolated polypeptide of claim 3, further comprising a linker sequence situated between said SEQ ID NO:2 and said polypeptide sequence of a selected targeting protein.

5. The isolated polypeptide of claim 3, wherein said targeting protein comprises human vascular endothelial growth factor (VEGF).

6. The isolated polypeptide of claim 3, comprising the polypeptide sequence of SEQ ID NO:6.

7. The isolated polypeptide of claim 3, comprising the polypeptide sequence of SEQ ID NO:8.

8. The isolated polypeptide of claim 3, wherein said targeting protein comprises human annexin V.

9. The isolated polypeptide of claim 3, comprising the polypeptide sequence of SEQ ID NO:10.

10. The isolated polypeptide of claim 3, wherein said targeting protein comprises a catalytically inactive fragment of anthrax lethal factor.

11. The isolated polypeptide of claim 3, comprising the polypeptide sequence of SEQ ID NO:12.

12. The isolated polypeptide of claim 3, wherein said targeting protein comprises single chain vascular endothelial growth factor (scVEGF) having the protein sequence of SEQ ID NO:4.

13. The isolated polypeptide of claim 3, comprising the polypeptide sequence of SEQ ID NO:14.

* * * * *